United States Patent
McGilligan

(10) Patent No.: US 12,227,579 B2
(45) Date of Patent: *Feb. 18, 2025

(54) BISPECIFIC ANTIBODY TARGETING IL-1R1 AND NLPR3

(71) Applicant: University of Ulster, Coleraine (GB)

(72) Inventor: Victoria McGilligan, Coleraine (GB)

(73) Assignee: UNIVERSITY OF ULSTER, Coleraine (GB)

( * ) Notice: Subject to any disclaimer, the term of this patent is extended or adjusted under 35 U.S.C. 154(b) by 913 days.

This patent is subject to a terminal disclaimer.

(21) Appl. No.: 17/275,995

(22) PCT Filed: Sep. 16, 2019

(86) PCT No.: PCT/EP2019/074744
§ 371 (c)(1),
(2) Date: Mar. 12, 2021

(87) PCT Pub. No.: WO2020/053446
PCT Pub. Date: Mar. 19, 2020

(65) Prior Publication Data
US 2022/0041739 A1 Feb. 10, 2022

(30) Foreign Application Priority Data

Sep. 14, 2018 (GB) .................................... 1815045

(51) Int. Cl.
| | |
|---|---|
| C07K 16/28 | (2006.01) |
| A61P 27/06 | (2006.01) |
| A61P 29/00 | (2006.01) |
| A61K 39/00 | (2006.01) |

(52) U.S. Cl.
CPC .......... *C07K 16/2866* (2013.01); *A61P 27/06* (2018.01); *A61P 29/00* (2018.01); *C07K 16/28* (2013.01); *A61K 2039/505* (2013.01); *C07K 2317/31* (2013.01); *C07K 2317/34* (2013.01); *C07K 2317/622* (2013.01); *C07K 2317/77* (2013.01)

(58) Field of Classification Search
None
See application file for complete search history.

(56) References Cited

FOREIGN PATENT DOCUMENTS

| WO | 2010052505 A1 | 5/2010 |
| WO | 2015123493 A2 | 8/2015 |

OTHER PUBLICATIONS

Chaurasia et al. The NLRP3 Inflammasome May Contribute to Pathologic Neovascularization in the Advanced Stages of Diabetic Retinopathy. Scientific Reports. 8:2847; Published: Feb. 12, 2018 (Year: 2018).*
Chi et al. HMGB1 promotes the activation of NLRP3 and caspase-8 inflammasomes via NF-κB pathway in acute glaucoma. Journal of Neuroinflammation. 12: 137; Published: Jul. 30, 2015 (Year: 2015).*
Puyang et al. Retinal Ganglion Cell Loss is Delayed Following Optic Nerve Crush in NLRP3 Knockout Mice. Scientific Reports. 6: 20998; Published: Feb. 19, 2016 (Year: 2016).*
Brinkmann and Kontermann. The making of bispecific antibodies. MAbs. 9(2): 182-212; Published: Jan. 10, 2017 (Year: 2017).*
Goel et al. Plasticity within the Antigen-Combining Site May Manifest as Molecular Mimicry in the Humoral Immune Response. Journal of Immunology. 173(12): 7358-7367; Published: Dec. 15, 2004 (Year: 2004).*
Lloyd et al. Modelling the human immune response: performance of a 1011 human antibody repertoire against a broad panel of therapeutically relevant antigens. Protein Engineering, Design & Selection. 22(3): 159-168; Published: Oct. 29, 2008 (Year: 2008).*
Edwards et al. The Remarkable Flexibility of the Human Antibody Repertoire; Isolation of Over One Thousand Different Antibodies to a Single Protein, BLyS. Journal of Molecular Biology. 334: 103-118; Nov. 14, 2003 (Year: 2003).*
Kauppinen et al. Inflammation and its role in age-related macular degeneration. Cellular and Molecular Life Sciences. 73: 1765-1786; Published: Feb. 6, 2016 (Year: 2016).*
Copland et al. A Perspective of AMD Through the Eyes of Immunology. Investigative Ophthalmology & Visual Science. 59(4): AMD83-AMD92; Published: Jul. 2018 (Year: 2018).*
Yerramothu et al. Inflammasomes, the eye and anti-inflammasome therapy. Eye. 32: 491-505; Published: Nov. 24, 2018 (Year: 2018).*
Calverley et al., "A Randomised, Placebo-Controlled Trial of Anti-Interleukin-1 Receptor 1 Monoclonal Antibody MEDI8968 in Chronic Obstructive Pulmonary Disease," Respir Res., 18(1):153, Aug. 2017.
Feng, "NLRP3 Inflammasome in Retinal Ganglion Cell Loss in Optic Neuropathy," Neural Regen Res., 11(7):1077-1078, Jul. 2016.
International Search Report and Written Opinion of the ISA/EP in PCT/EP2019/074744, dated Dec. 10, 2019; 16pgs.
Jeru et al., "Inflammasome and Interleukin 1," La Revue de Medecine Interne, 32(4):218-224, Jun. 2010.
McGilligan et al., "InflaMab: A Novel Inhibitor of Inflammation Targeting the NLRP3 Inflammasome," Ulster University Research Output, accessed on the internet at https://pure.ulster.ac.uk/en/publications/inflamab-a-novel-inhibitor-of-inflammation-targeting-the-nlrp3-in, retrieved Nov. 22, 2019, 2pgs., Aug. 2019.

(Continued)

*Primary Examiner* — Juliet C Switzer
*Assistant Examiner* — Katherine Ann Holtzman
(74) *Attorney, Agent, or Firm* — Haukaas Fortius PLLC; Paul K. Judd; Michael Haukaas

(57) ABSTRACT

The present disclosure concerns modulators of the NLRP3 inflammasome pathway, in particular an NLRP3 inflammasome modulator which is capable of binding to both of IL-1R1 and NLRP3, for use in the treatment or prophylaxis of inflammatory eye diseases such as glaucoma.

12 Claims, 27 Drawing Sheets
Specification includes a Sequence Listing.

(56) References Cited

OTHER PUBLICATIONS

Swanson et al., "The NLRP3 Inflammasome: Molecular Activation and Regulation to Therapeutics," Nat Rev Immunol., 19(8):477-489, Aug. 2019.
Yerramothu et al., "Inflammasomes, the eye and anti-inflammasome therapy," Eye., 32, 491-505, Nov. 2017.

* cited by examiner

Figure 11:
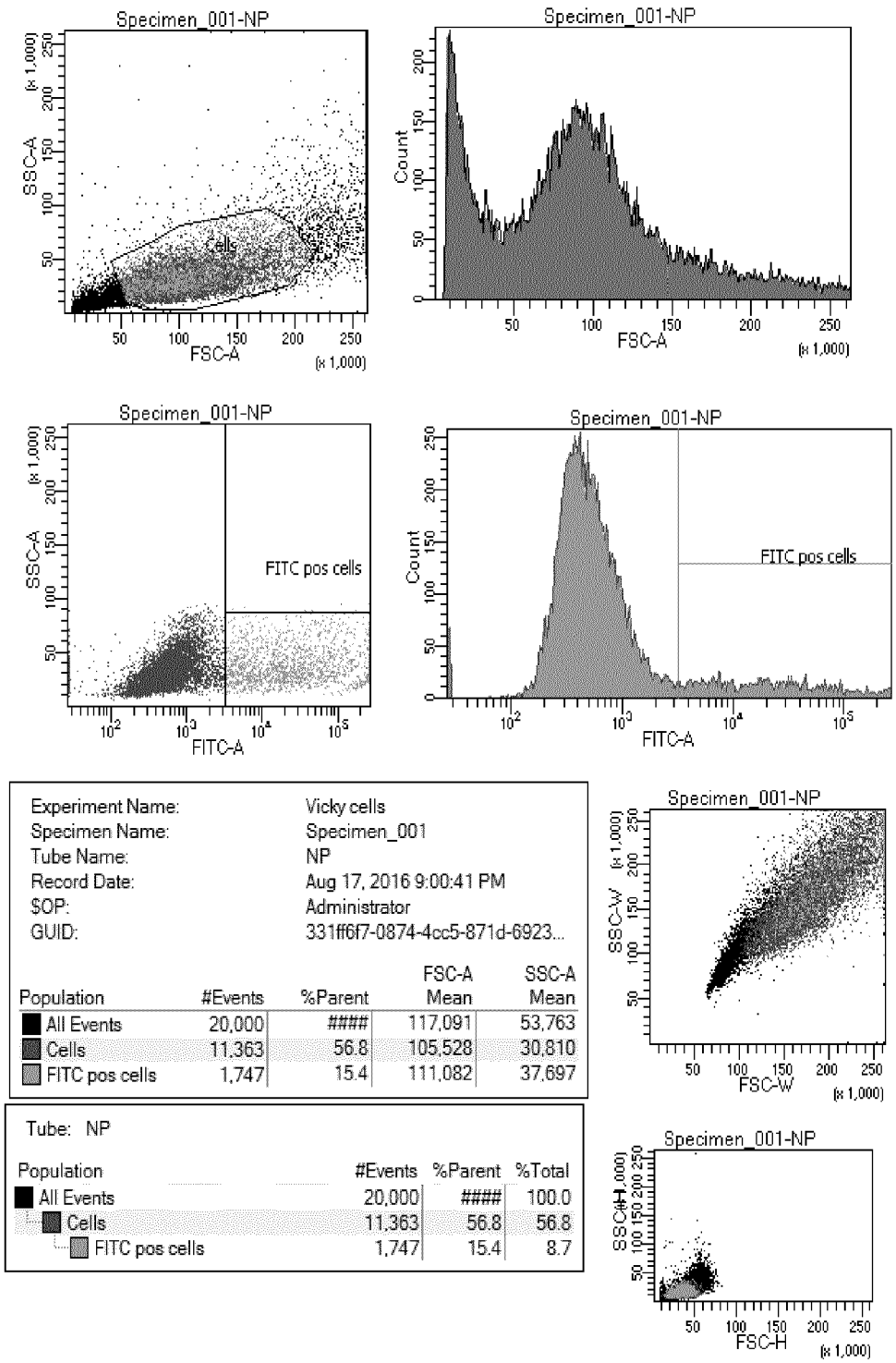

Figure 11 (ii):
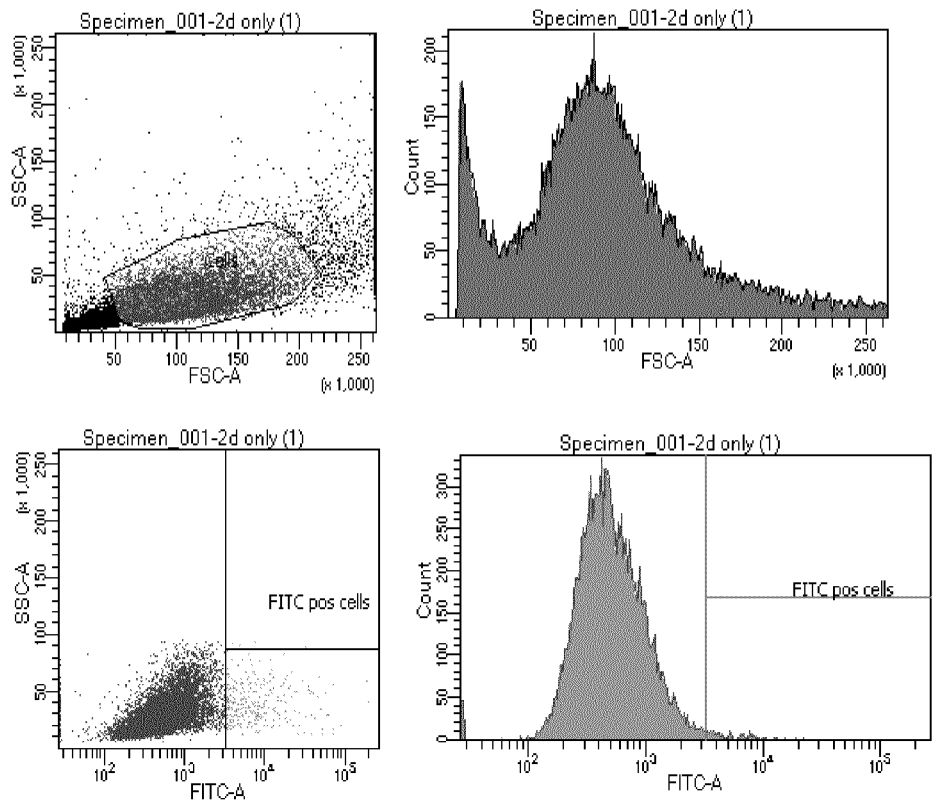
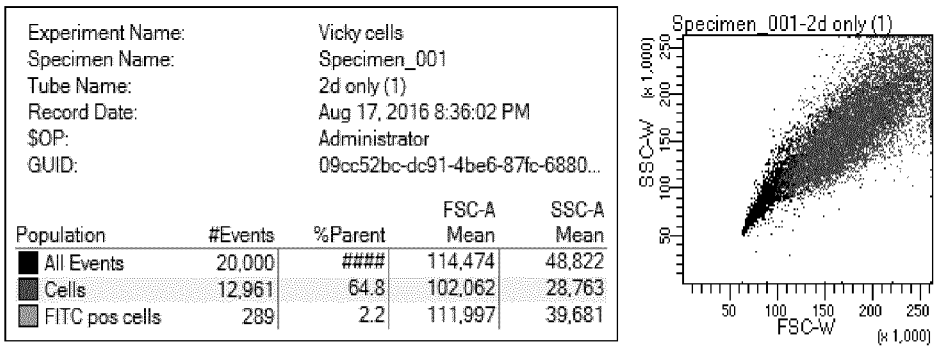
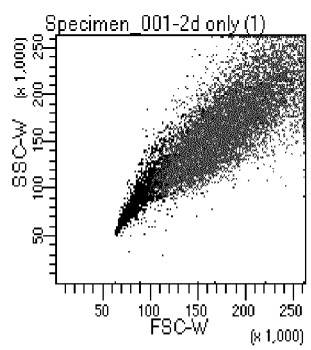
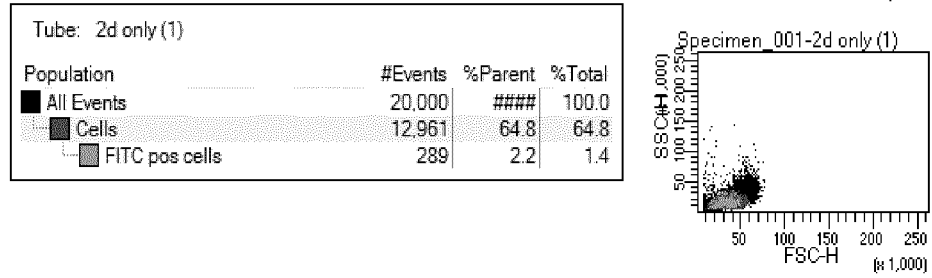
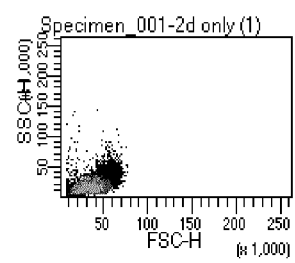

Figure 15:

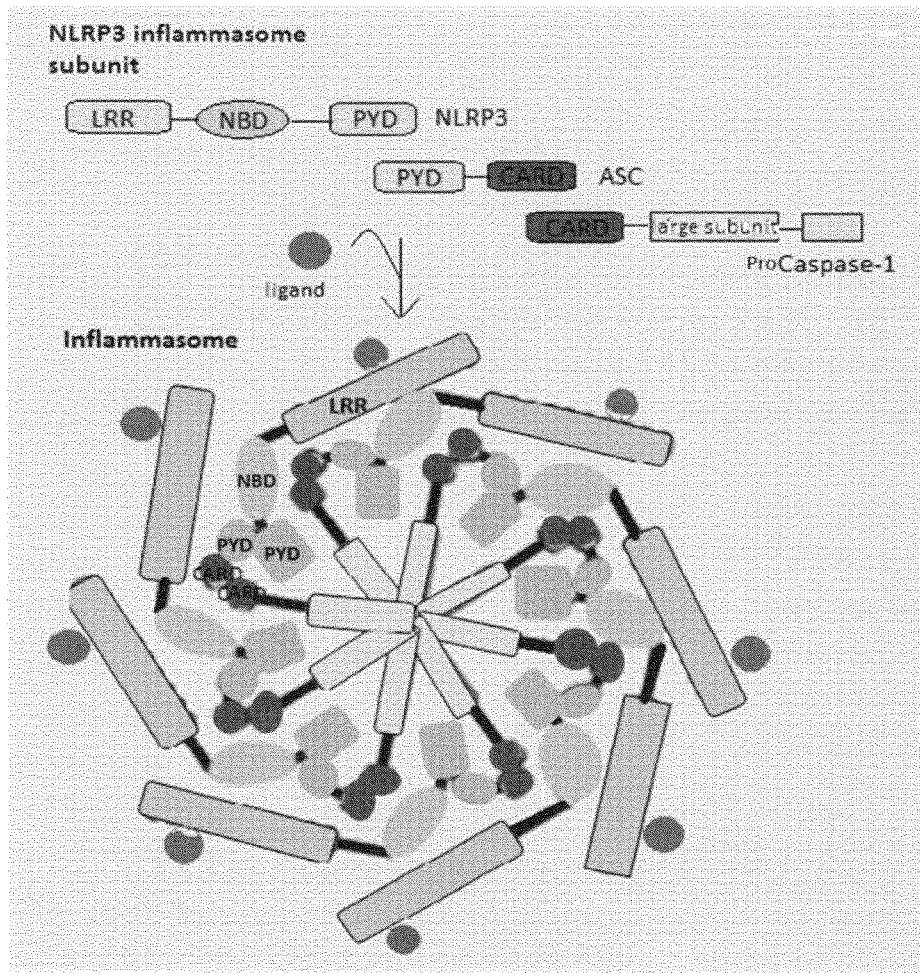

Figure 16:

Sequence Analysis

```
SP|Q96P20|NALP3_HUMAN   KMASTRCKLARYLEDLEDVDLKKFKMHLEDYPPQKGCIPLPRGQTEKADHVDLATLMIDF  61
SP|Q8R4B8|NALP3_MOUSE   -MTSVRCKLAQYLEDLEDVDLKKFKMHLEDYPPEKGCIPVPRGQMEKADHLDLATLMIDF  59
SP|Q9C000|NALP1_HUMAN   MAGGAWGRLACYLEFLKKEELKEFQLLLANKAHSRSSSGETPAQPEKTSGMEVASYLVAQ  60
SP|Q9NX02|NALP2_HUMAN   SSAQMGFNLQALLEQLSQDELSKFKYLITTFSLAHELQKIPHKEVDKADGKQLVEILTTH  62
SP|Q8WX94|NALP7_HUMAN   TSPQLEWTLQTLLEQLNEDELKSFKSLLWAFPLEDVLQKTPWSEVEEADGKKLAEILVNT  61
SP|Q96MN2|NALP4_HUMAN   ASFFSDFGLMWYLEELKKEEFRKFKEHLKQMTLQLELKQIPWTEVKKASREELANLLIKH  62
SP|P59047|NALP5_HUMAN   SLTFSSYGLQWCLYELDKEEFQTFKELLKKKSSESTTCSIPQFEIENANVECLALLLHEY  116
SP|P59046|NAL12_HUMAN   AGRDGLCRLSTYLEELEAVELKKFKLYLGTA-TELGEGKIPWGSMEKAGPLEMAQLLITH  63
SP|Q86W24|NAL14_HUMAN   SSFFPDFGLLLYLEELNKEELNTFKLFLKETM-EPEHGLTPWNEVKKARREDLANLMKKY  65
SP|Q86W28|NALP8_HUMAN   PGSPCENGVMLYMRNVSHEELQRFKQLLLTEL-STGTMPITWDQVETASWAEVVHLLIER  91
SP|Q7RTR0|NALP9_HUMAN   ESFFSDFGLLWYLKELRKEEFWKFKELLKQPLEKFELKPIPWAELKKASKEDVAKLLDKH  62
SP|P59044|NALP6_HUMAN   RLAVARELLLAALEELSQEQLKRFRHKLRDVGPDG--RSIPWGRLERADAVDLAEQLAQF  71
SP|Q86W26|NAL10_HUMAN   KARKPREALLWALSDLEENDFKKLKFYLRDMTLSEGQPPLARGELEGLIPVDLAELLISK  64
SP|P59045|NAL11_HUMAN   ESDSTDFDLLWYLENLSDKEFQSFKKYLARKILDFKL---PQFPLIQMTKEELANVLPIS  59
```

NLRP3 110kDa

βActin 42kDa -

Figure 35:
A.
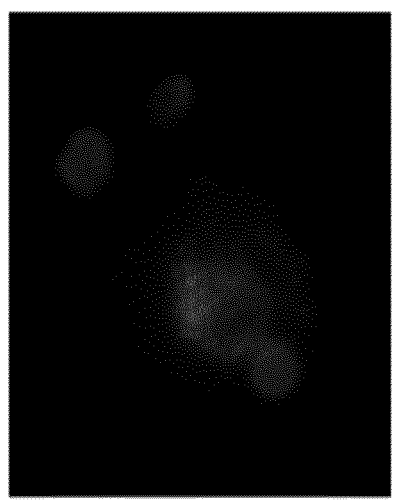
B.
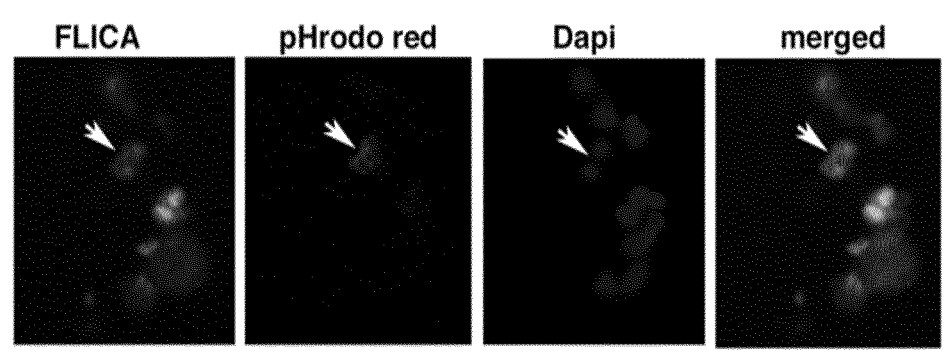

Figure 40:
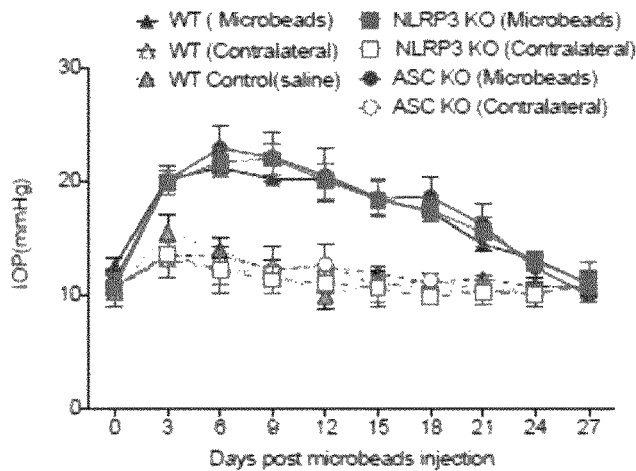
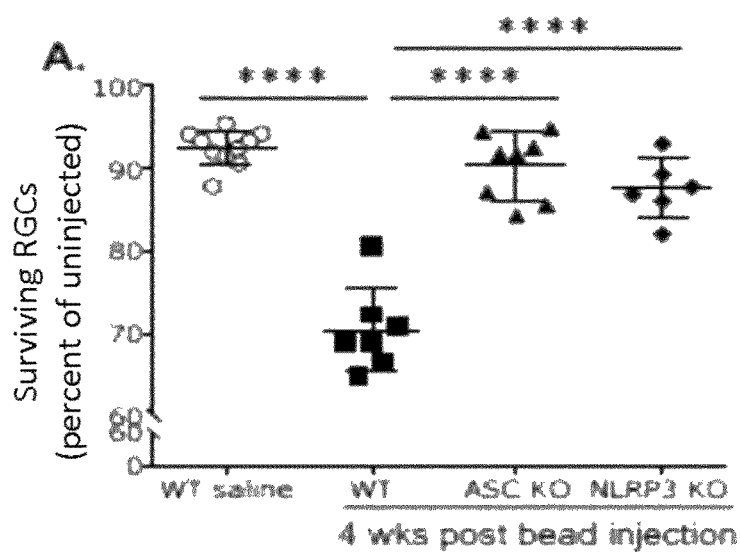
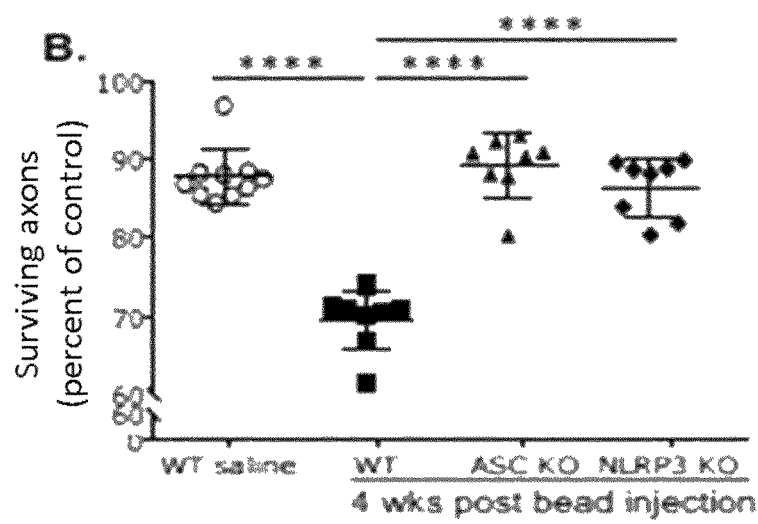

Figure 41:
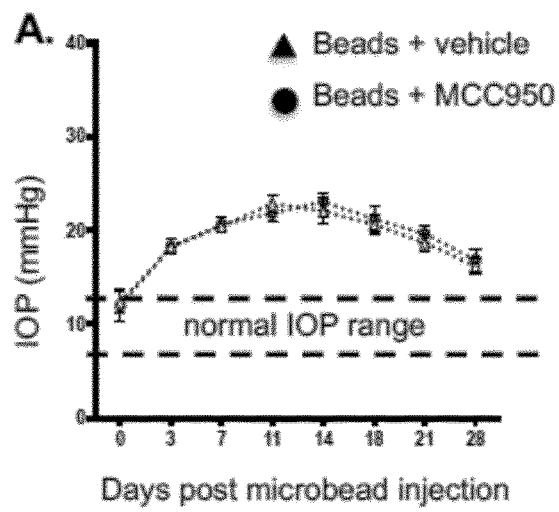
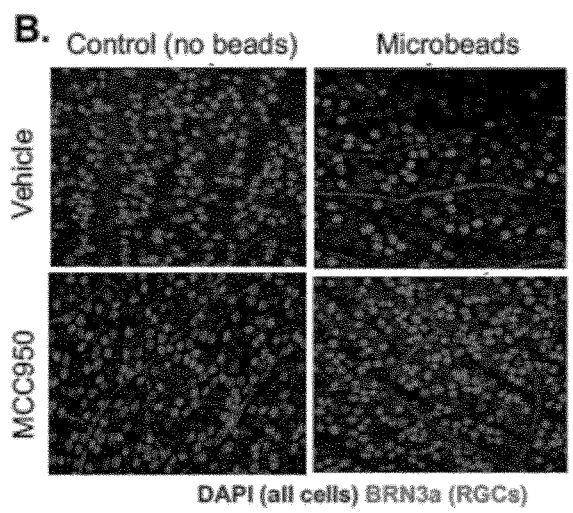
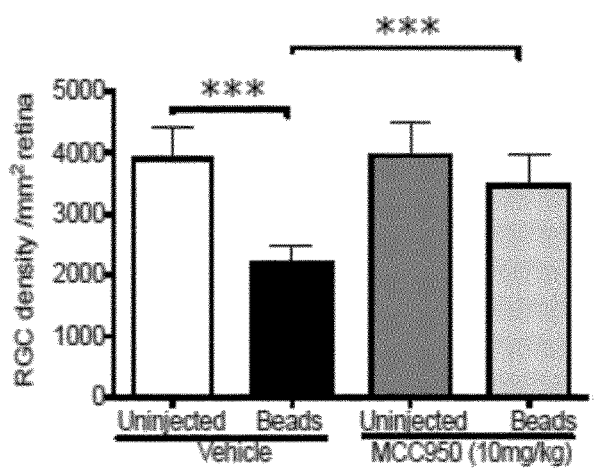

SEQUENCE LISTING

```
<160> NUMBER OF SEQ ID NOS: 69

<210> SEQ ID NO 1
<211> LENGTH: 550
<212> TYPE: PRT
<213> ORGANISM: Artificial Sequence
<220> FEATURE:
<223> OTHER INFORMATION: Synthetic

<400> SEQUENCE: 1

Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
    290                 295                 300
```

```
Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
            325                 330                 335

Leu Glu Gly Gly Pro Ser Val Phe Ile Phe Pro Pro Asn Ile Lys Asp
        340                 345                 350

Val Leu Met Ile Ser Leu Thr Pro Lys Val Thr Cys Val Val Val Asp
    355                 360                 365

Val Ser Glu Asp Asp Pro Asp Val Gln Ile Ser Trp Phe Val Asn Asn
370                 375                 380

Val Glu Val His Thr Ala Gln Thr Gln Thr His Arg Glu Asp Tyr Asn
385                 390                 395                 400

Ser Thr Ile Arg Val Val Ser His Leu Pro Ile Gln His Gln Asp Trp
                405                 410                 415

Met Ser Gly Lys Glu Phe Lys Cys Lys Val Asn Asn Lys Asp Leu Pro
            420                 425                 430

Ser Pro Ile Glu Arg Thr Ile Ser Lys Pro Lys Gly Leu Val Arg Ala
        435                 440                 445

Pro Gln Val Tyr Thr Leu Pro Pro Ala Glu Gln Leu Ser Arg Lys
    450                 455                 460

Asp Val Ser Leu Thr Cys Leu Val Val Gly Phe Asn Pro Gly Asp Ile
465                 470                 475                 480

Ser Val Glu Trp Thr Ser Asn Gly His Thr Glu Glu Asn Tyr Lys Asp
                485                 490                 495

Thr Ala Pro Val Leu Asp Ser Asp Gly Ser Tyr Phe Ile Tyr Ser Lys
            500                 505                 510

Leu Asn Met Lys Thr Ser Lys Trp Glu Lys Thr Asp Ser Phe Ser Cys
        515                 520                 525

Asn Val Arg His Glu Gly Leu Lys Asn Tyr Tyr Leu Lys Lys Thr Ile
    530                 535                 540

Ser Arg Ser Pro Gly Lys
545                 550

<210> SEQ ID NO 2
<211> LENGTH: 151
<212> TYPE: PRT
<213> ORGANISM: Artificial Sequence
<220> FEATURE:
<223> OTHER INFORMATION: Synthetic

<400> SEQUENCE: 2

Met Glu Trp Ser Cys Val Met Leu Phe Leu Met Ala Ala Ala Gln Ser
1               5                   10                  15

Ile Gln Ala Gln Ile Gln Leu Val Gln Ser Gly Pro Glu Leu Arg Lys
            20                  25                  30

Pro Gly Glu Thr Val Arg Ile Ser Cys Lys Ala Ser Gly Tyr Pro Phe
        35                  40                  45

Thr Thr Ala Gly Leu Gln Trp Val Gln Lys Met Ser Gly Lys Gly Leu
    50                  55                  60

Lys Trp Ile Gly Trp Met Asn Thr Gln Ser Gly Val Pro Lys Tyr Ala
65                  70                  75                  80

Glu Glu Phe Lys Gly Arg Ile Ala Phe Ser Leu Glu Thr Ala Ala Ser
                85                  90                  95

Thr Ala Tyr Leu Gln Ile Asn Asn Leu Lys Thr Glu Asp Thr Ala Thr
            100                 105                 110
```

```
Tyr Phe Cys Ala Lys Ser Val Tyr Phe Asn Trp Arg Tyr Phe Asp Val
        115                 120                 125

Trp Gly Ala Gly Thr Thr Val Thr Val Ser Ser Ala Lys Thr Thr Pro
    130                 135                 140

Pro Pro Val Tyr Pro Leu Ala
145                 150

<210> SEQ ID NO 3
<211> LENGTH: 153
<212> TYPE: PRT
<213> ORGANISM: Artificial Sequence
<220> FEATURE:
<223> OTHER INFORMATION: Synthetic

<400> SEQUENCE: 3

Val His Met Glu Cys Ser Cys Val Met Leu Phe Leu Met Ala Ala Ala
1               5                   10                  15

Gln Ser Ile Gln Ala Gln Ile Gln Leu Val Gln Ser Gly Pro Glu Leu
            20                  25                  30

Arg Lys Pro Gly Glu Thr Val Arg Ile Ser Arg Lys Ala Ser Gly Tyr
        35                  40                  45

Pro Phe Thr Thr Ala Gly Leu Gln Trp Val Gln Lys Met Ser Gly Lys
    50                  55                  60

Gly Leu Lys Trp Ile Gly Trp Met Asn Thr Gln Ser Glu Val Pro Lys
65                  70                  75                  80

Tyr Ala Glu Glu Phe Lys Gly Arg Ile Ala Phe Ser Leu Glu Thr Ala
                85                  90                  95

Ala Ser Thr Ala Tyr Leu Gln Ile Asn Asn Leu Lys Thr Glu Asp Thr
            100                 105                 110

Ala Thr Tyr Phe Cys Ala Lys Ser Val Tyr Phe Asn Trp Arg Tyr Phe
        115                 120                 125

Asp Val Trp Gly Ala Gly Thr Thr Val Thr Val Ser Ser Ala Lys Thr
    130                 135                 140

Thr Pro Pro Ser Val Phe Pro Leu Ala
145                 150

<210> SEQ ID NO 4
<211> LENGTH: 153
<212> TYPE: PRT
<213> ORGANISM: Artificial Sequence
<220> FEATURE:
<223> OTHER INFORMATION: Synthetic

<400> SEQUENCE: 4

Val His Met Gly Trp Ser Trp Val Met Leu Phe Leu Met Ala Ala Ala
1               5                   10                  15

Gln Ser Ile Gln Ala Gln Ile Gln Leu Val Gln Ser Gly Pro Glu Leu
            20                  25                  30

Arg Lys Pro Gly Glu Thr Val Arg Ile Ser Cys Lys Ala Ser Gly Tyr
        35                  40                  45

Pro Phe Thr Thr Ala Gly Leu Gln Trp Val Lys Met Ser Gly Lys
    50                  55                  60

Gly Leu Lys Trp Ile Gly Trp Met Asn Thr Gln Ser Glu Val Pro Lys
65                  70                  75                  80

Tyr Ala Glu Glu Phe Lys Gly Arg Ile Ala Phe Ser Leu Glu Thr Ala
                85                  90                  95

Ala Ser Thr Ala Tyr Leu Gln Ile Asn Asn Leu Lys Thr Glu Asp Thr
```

```
                100                 105                 110
Ala Thr Tyr Phe Cys Ala Lys Ser Val Tyr Phe Asn Trp Arg Tyr Phe
            115                 120                 125

Asp Val Trp Gly Ala Gly Thr Thr Val Thr Val Ser Ser Ala Lys Thr
        130                 135                 140

Thr Pro Pro Val Tyr Pro Leu Ala
145                 150

<210> SEQ ID NO 5
<211> LENGTH: 151
<212> TYPE: PRT
<213> ORGANISM: Artificial Sequence
<220> FEATURE:
<223> OTHER INFORMATION: Synthetic

<400> SEQUENCE: 5

Met Gly Trp Val Trp Asn Leu Leu Phe Leu Met Ala Ala Ala Gln Ser
1               5                   10                  15

Ile Gln Ala Gln Ile Gln Leu Val Gln Ser Gly Pro Glu Leu Arg Lys
            20                  25                  30

Pro Gly Glu Thr Val Arg Ile Ser Cys Lys Ala Ser Gly Tyr Pro Phe
        35                  40                  45

Thr Thr Ala Gly Leu Gln Trp Val Gln Lys Met Ser Gly Lys Gly Leu
    50                  55                  60

Lys Trp Ile Gly Trp Met Asn Thr Gln Ser Glu Val Pro Lys Tyr Ala
65                  70                  75                  80

Glu Glu Phe Lys Gly Arg Ile Ala Phe Ser Leu Glu Thr Ala Ala Ser
                85                  90                  95

Thr Ala Tyr Leu Gln Ile Asn Asn Leu Lys Thr Glu Asp Thr Ala Thr
            100                 105                 110

Tyr Phe Cys Ala Lys Ser Val Tyr Phe Asn Trp Arg Tyr Phe Asp Val
        115                 120                 125

Trp Gly Ala Gly Thr Thr Val Thr Val Ser Ser Ala Lys Thr Thr Pro
    130                 135                 140

Pro Pro Val Tyr Pro Leu Val
145                 150

<210> SEQ ID NO 6
<211> LENGTH: 151
<212> TYPE: PRT
<213> ORGANISM: Artificial Sequence
<220> FEATURE:
<223> OTHER INFORMATION: Synthetic

<400> SEQUENCE: 6

Met Gly Trp Val Trp Thr Leu Pro Phe Leu Met Ala Ala Ala Gln Ser
1               5                   10                  15

Ile Gln Ala Gln Ile Gln Leu Val Gln Ser Gly Pro Glu Leu Arg Lys
            20                  25                  30

Pro Gly Glu Thr Val Arg Ile Ser Cys Lys Ala Ser Gly Tyr Pro Phe
        35                  40                  45

Thr Thr Ala Gly Leu Gln Trp Val Gln Lys Met Ser Gly Lys Gly Leu
    50                  55                  60

Lys Trp Ile Gly Trp Met Asn Thr Gln Ser Glu Val Pro Lys Tyr Ala
65                  70                  75                  80

Glu Glu Phe Lys Gly Arg Ile Ala Phe Ser Leu Glu Thr Ala Ala Ser
                85                  90                  95
```

```
Thr Ala Tyr Leu Gln Ile Asn Asn Leu Lys Thr Glu Asp Thr Ala Thr
                100                 105                 110

Tyr Phe Cys Ala Lys Ser Val Tyr Phe Asn Trp Arg Tyr Phe Asp Val
            115                 120                 125

Trp Gly Ala Gly Thr Thr Val Thr Val Ser Ser Ala Lys Thr Thr Pro
        130                 135                 140

Pro Pro Val Tyr Pro Leu Val
145             150

<210> SEQ ID NO 7
<211> LENGTH: 151
<212> TYPE: PRT
<213> ORGANISM: Artificial Sequence
<220> FEATURE:
<223> OTHER INFORMATION: Synthetic

<400> SEQUENCE: 7

Met Gly Trp Val Trp Asn Leu Pro Phe Leu Met Ala Ala Ala Gln Ser
1               5                   10                  15

Ile Gln Ala Gln Ile Gln Leu Val Gln Ser Gly Pro Glu Leu Arg Lys
                20                  25                  30

Pro Gly Glu Thr Val Arg Ile Ser Cys Lys Ala Ser Gly Tyr Pro Phe
            35                  40                  45

Thr Thr Ala Gly Leu Gln Trp Val Gln Lys Met Ser Gly Lys Gly Leu
        50                  55                  60

Lys Trp Ile Gly Trp Met Asn Thr Gln Ser Glu Val Pro Lys Tyr Ala
65                  70                  75                  80

Glu Glu Phe Lys Gly Arg Ile Ala Phe Ser Leu Glu Thr Ala Ala Ser
                85                  90                  95

Thr Ala Tyr Leu Gln Ile Asn Asn Leu Lys Thr Glu Asp Thr Ala Thr
                100                 105                 110

Tyr Phe Cys Ala Lys Ser Val Tyr Phe Asn Trp Arg Tyr Phe Asp Val
            115                 120                 125

Trp Gly Ala Gly Thr Thr Val Thr Val Ser Ser Ala Lys Thr Thr Pro
        130                 135                 140

Pro Pro Val Tyr Pro Leu Ala
145             150

<210> SEQ ID NO 8
<211> LENGTH: 151
<212> TYPE: PRT
<213> ORGANISM: Artificial Sequence
<220> FEATURE:
<223> OTHER INFORMATION: Synthetic

<400> SEQUENCE: 8

Met Asp Trp Val Trp Thr Leu Pro Phe Leu Met Ala Ala Ala Gln Ser
1               5                   10                  15

Ile Gln Ala Gln Ile Gln Leu Val Gln Ser Gly Pro Glu Leu Arg Lys
                20                  25                  30

Pro Gly Glu Thr Val Arg Ile Ser Cys Lys Ala Ser Gly Tyr Pro Phe
            35                  40                  45

Thr Thr Ala Gly Leu Gln Trp Val Gln Lys Met Ser Gly Lys Gly Leu
        50                  55                  60

Lys Trp Ile Gly Trp Met Asn Thr Gln Ser Glu Val Pro Lys Tyr Ala
65                  70                  75                  80

Glu Glu Phe Lys Gly Arg Ile Ala Phe Ser Leu Glu Thr Ala Ala Ser
                85                  90                  95
```

```
Thr Ala Tyr Leu Gln Ile Asn Asn Leu Lys Thr Glu Asp Thr Ala Thr
                100                 105                 110

Tyr Phe Cys Ala Lys Ser Val Tyr Phe Asn Trp Arg Tyr Phe Asp Val
            115                 120                 125

Trp Gly Ala Gly Thr Thr Val Thr Val Ser Ser Ala Lys Thr Thr Pro
        130                 135                 140

Pro Ser Val Tyr Pro Leu Ala
145                 150

<210> SEQ ID NO 9
<211> LENGTH: 151
<212> TYPE: PRT
<213> ORGANISM: Artificial Sequence
<220> FEATURE:
<223> OTHER INFORMATION: Synthetic

<400> SEQUENCE: 9

Met Asp Trp Leu Trp Asn Leu Pro Phe Leu Met Ala Ala Ala Gln Ser
1               5                   10                  15

Ile Gln Ala Gln Ile Gln Leu Val Gln Ser Gly Pro Glu Leu Arg Lys
            20                  25                  30

Pro Gly Glu Thr Val Arg Ile Ser Cys Lys Ala Ser Gly Tyr Pro Phe
        35                  40                  45

Thr Thr Ala Gly Leu Gln Trp Val Gln Lys Met Ser Gly Lys Gly Leu
    50                  55                  60

Lys Trp Ile Gly Trp Met Asn Thr Gln Ser Glu Val Pro Lys Tyr Ala
65                  70                  75                  80

Glu Glu Phe Lys Gly Arg Ile Ala Phe Ser Leu Glu Thr Ala Ala Ser
                85                  90                  95

Thr Ala Tyr Leu Gln Ile Asn Asn Leu Lys Thr Glu Asp Thr Ala Thr
                100                 105                 110

Tyr Phe Cys Ala Lys Ser Val Tyr Phe Asn Trp Arg Tyr Phe Asp Val
            115                 120                 125

Trp Gly Ala Gly Thr Thr Val Thr Val Ser Ser Ala Lys Thr Thr Pro
        130                 135                 140

Pro Pro Val Tyr Pro Leu Ala
145                 150

<210> SEQ ID NO 10
<211> LENGTH: 162
<212> TYPE: PRT
<213> ORGANISM: Artificial Sequence
<220> FEATURE:
<223> OTHER INFORMATION: Synthetic

<400> SEQUENCE: 10

Met Arg Ala Pro Ala Gln Phe Leu Gly Leu Leu Leu Leu Trp Thr Ser
1               5                   10                  15

Ala Ser Arg Cys Asp Ile Val Met Thr Gln Ser Pro Ala Thr Leu Ser
            20                  25                  30

Val Thr Pro Gly Asp Arg Val Ser Leu Ser Cys Arg Ala Ser Gln Ser
        35                  40                  45

Ile Ser Asp Tyr Leu Ser Trp Tyr Gln Gln Arg Ser His Glu Ser Pro
    50                  55                  60

Arg Leu Ile Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Ser Ile Asn
```

```
                    85                  90                  95
Ser Val Glu Pro Glu Asp Val Gly Val Tyr Tyr Cys Gln His Gly His
                100                 105                 110

Ser Phe Pro Leu Thr Phe Gly Ser Gly Thr Lys Leu Glu Leu Lys Arg
                115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys

<210> SEQ ID NO 11
<211> LENGTH: 162
<212> TYPE: PRT
<213> ORGANISM: Artificial Sequence
<220> FEATURE:
<223> OTHER INFORMATION: Synthetic

<400> SEQUENCE: 11

Met Arg Ala Pro Ala Gln Leu Leu Gly Leu Leu Leu Phe Trp Thr Ser
1               5                   10                  15

Ala Ser Arg Cys Asp Ile Val Met Thr Gln Ser Pro Ala Thr Leu Ser
                20                  25                  30

Val Thr Pro Gly Asp Arg Val Ser Leu Ser Cys Arg Ala Ser Gln Ser
            35                  40                  45

Ile Ser Asp Tyr Leu Ser Trp Tyr Gln Gln Arg Ser His Glu Ser Pro
        50                  55                  60

Arg Leu Ile Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Asn Ile Asn
                85                  90                  95

Ser Val Glu Pro Glu Asp Val Gly Val Tyr Tyr Cys Gln His Gly His
                100                 105                 110

Ser Phe Pro Leu Thr Phe Gly Ser Gly Thr Lys Leu Glu Leu Lys Arg
                115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys

<210> SEQ ID NO 12
<211> LENGTH: 162
<212> TYPE: PRT
<213> ORGANISM: Artificial Sequence
<220> FEATURE:
<223> OTHER INFORMATION: Synthetic

<400> SEQUENCE: 12

Met Arg Ser Pro Ala Gln Phe Leu Gly Leu Leu Leu Phe Trp Thr Ser
1               5                   10                  15

Ala Ser Arg Cys Asp Ile Val Met Thr Gln Ser Pro Ala Thr Leu Ser
                20                  25                  30

Val Thr Pro Gly Asp Arg Val Ser Leu Ser Cys Arg Ala Ser Gln Ser
            35                  40                  45

Ile Ser Asp Tyr Leu Ser Trp Tyr Gln Gln Arg Ser His Glu Ser Pro
        50                  55                  60
```

```
Arg Leu Ile Ile Lys Tyr Ala Ser Gln Ser Ile Ser Gly Ile Pro Ser
 65                  70                  75                  80

Arg Phe Ser Gly Ser Gly Ser Gly Ser Asp Phe Thr Leu Ser Ile Asn
                 85                  90                  95

Ser Val Glu Pro Glu Asp Val Gly Val Tyr Tyr Cys Gln His Gly His
            100                 105                 110

Ser Phe Pro Leu Thr Phe Gly Ser Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys
```

<210> SEQ ID NO 13
<211> LENGTH: 162
<212> TYPE: PRT
<213> ORGANISM: Artificial Sequence
<220> FEATURE:
<223> OTHER INFORMATION: Synthetic

<400> SEQUENCE: 13

```
Met Arg Ser Pro Ala Gln Phe Leu Gly Leu Leu Leu Phe Trp Thr Ser
1               5                  10                  15

Ala Ser Arg Cys Asp Ile Val Met Thr Gln Ser Pro Ala Thr Leu Ser
                20                  25                  30

Val Thr Pro Gly Asp Arg Val Ser Leu Ser Cys Arg Ala Ser Gln Ser
            35                  40                  45

Ile Ser Asp Tyr Leu Ser Trp Tyr Gln Gln Arg Ser His Glu Ser Pro
        50                  55                  60

Arg Leu Ile Ile Lys Tyr Ala Ser Gln Ser Ile Ser Gly Ile Pro Ser
 65                  70                  75                  80

Arg Phe Ser Gly Ser Gly Ser Gly Ser Asp Phe Thr Leu Ser Ile Asn
                 85                  90                  95

Ser Val Glu Pro Glu Asp Val Gly Val Tyr Tyr Cys Gln His Gly His
            100                 105                 110

Ser Phe Pro Leu Thr Phe Gly Ser Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Arg
```

<210> SEQ ID NO 14
<211> LENGTH: 162
<212> TYPE: PRT
<213> ORGANISM: Artificial Sequence
<220> FEATURE:
<223> OTHER INFORMATION: Synthetic

<400> SEQUENCE: 14

```
Met Val Ser Ser Ala Gln Phe Leu Gly Leu Leu Leu Phe Trp Thr Ser
1               5                  10                  15

Ala Ser Arg Cys Asp Ile Val Met Thr Gln Ser Pro Ala Thr Leu Ser
                20                  25                  30
```

Val Thr Pro Gly Asp Arg Val Ser Leu Ser Cys Arg Ala Ser Gln Ser
        35                  40                  45

Ile Ser Asp Tyr Leu Ser Trp Tyr Gln Gln Arg Ser His Glu Ser Pro
 50                  55                  60

Arg Leu Ile Ile Lys Tyr Ala Ser Gln Ser Ile Ser Gly Ile Pro Ser
 65                  70                  75                  80

Arg Phe Ser Gly Ser Gly Ser Gly Ser Asp Phe Thr Leu Ser Ile Asn
                 85                  90                  95

Ser Val Glu Pro Glu Asp Val Gly Val Tyr Tyr Cys Gln His Gly His
            100                 105                 110

Ser Phe Pro Leu Thr Phe Gly Ser Gly Thr Lys Leu Glu Leu Lys Arg
            115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys

<210> SEQ ID NO 15
<211> LENGTH: 162
<212> TYPE: PRT
<213> ORGANISM: Artificial Sequence
<220> FEATURE:
<223> OTHER INFORMATION: Synthetic

<400> SEQUENCE: 15

Met Val Ser Thr Ala Gln Phe Leu Gly Leu Leu Leu Phe Trp Thr Ser
 1               5                  10                  15

Ala Ser Arg Cys Asp Ile Val Met Thr Gln Ser Pro Ala Thr Leu Ser
                20                  25                  30

Val Thr Pro Gly Asp Arg Val Ser Leu Ser Cys Arg Ala Ser Gln Ser
        35                  40                  45

Ile Ser Asp Tyr Leu Ser Trp Tyr Gln Gln Arg Ser His Glu Ser Pro
 50                  55                  60

Arg Leu Ile Ile Lys Tyr Ala Ser Gln Ser Ile Ser Gly Ile Pro Ser
 65                  70                  75                  80

Arg Phe Ser Gly Ser Gly Ser Gly Ser Asp Phe Thr Leu Ser Ile Asn
                 85                  90                  95

Ser Val Glu Pro Glu Asp Val Gly Val Tyr Tyr Cys Gln His Gly His
            100                 105                 110

Ser Phe Pro Leu Thr Phe Gly Ser Gly Thr Lys Leu Glu Leu Lys Arg
            115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Arg

<210> SEQ ID NO 16
<211> LENGTH: 453
<212> TYPE: DNA
<213> ORGANISM: Artificial Sequence
<220> FEATURE:
<223> OTHER INFORMATION: Synthetic

<400> SEQUENCE: 16
atggaatgga gctgtgtcat gctctttctc atggcagcag ctcaaagtat ccaagcacag      60

```
atccagttgg tgcagtctgg acctgagctg aggaagcctg gagagacagt caggatctcc   120
tgcaaggcct ctgggtatcc cttcacaact gctggattgc agtgggtaca gaagatgtca   180
ggaaagggtt tgaaatggat tggctggatg aacacccagt ctgaagtgcc aaaatatgca   240
gaagagttca agggacggat tgccttctct ttggaaaccg ctgccagtac tgcatattta   300
cagataaaca acctcaaaac tgaggacacg gcaacgtatt tctgtgcgaa atcggtctat   360
tttaactgga gatatttcga tgtctggggt gcagggacca cggtcaccgt ctcctcagcc   420
aaaacgacac ccccacccgt ttatccactg gcc                                453
```

<210> SEQ ID NO 17
<211> LENGTH: 453
<212> TYPE: DNA
<213> ORGANISM: Artificial Sequence
<220> FEATURE:
<223> OTHER INFORMATION: Synthetic

<400> SEQUENCE: 17

```
atgggatgga gctgggtcat gctctttctc atggcagcag ctcaaagtat ccaagcacag   60
atccagttgg tgcagtctgg acctgagctg aggaagcctg gagagacagt caggatctcc   120
tgcaaggctt ctgggtatcc cttcacaact gctggactgc agtgggtaca gaagatgtca   180
ggaaagggtt tgaaatggat tggctggatg aacacccagt ctgaagtgcc aaaatatgca   240
gaagagttca agggacggat tgccttctct ttggaaaccg ctgccagtac tgcatattta   300
cagataaaca acctcaaaac tgaggacacg gcaacgtatt tctgtgcgaa atcggtctat   360
tttaactgga gatatttcga tgtctggggt gcagggacca cggtcaccgt ctcctcagcc   420
aaaacgacac ccccacccgt ttatcccttg gcc                                453
```

<210> SEQ ID NO 18
<211> LENGTH: 453
<212> TYPE: DNA
<213> ORGANISM: Artificial Sequence
<220> FEATURE:
<223> OTHER INFORMATION: Synthetic

<400> SEQUENCE: 18

```
atggaatgca gctgtgtaat gctctttctc atggcagcag ctcaaagtat ccaagcacag   60
atccagttgg tgcagtctgg acctgagctg aggaagcctg gagagacagt caggatctcc   120
cgcaaggctt ctgggtatcc cttcacaact gctggattgc agtgggtaca gaagatgtca   180
ggaaagggtt tgaaatggat tggctggatg aacacccagt ctgaagtgcc aaaatatgca   240
gaagagttca agggacggat tgccttctct ttggaaaccg ctgccagtac tgcatattta   300
cagataaaca acctcaaaac tgaggacacg gcaacgtatt tctgtgcgaa atcggtctat   360
tttaactgga gatatttcga tgtctggggt gcagggacca cggtcaccgt ctcctcagcc   420
aaaacgacac cccatccgt cttcccccctg gca                                453
```

<210> SEQ ID NO 19
<211> LENGTH: 453
<212> TYPE: DNA
<213> ORGANISM: Artificial Sequence
<220> FEATURE:
<223> OTHER INFORMATION: Synthetic

<400> SEQUENCE: 19

```
atgggttggg tgtggaactt gctattcctc atggcagcag ctcaaagtat ccaagcacag   60
```

| | |
|---|---|
| atccagctgg tgcagtctgg acctgagctg aggaagcctg agagacagt caggatctcc | 120 |
| tgcaaggctt ctgggtatcc cttcacaact gctggattgc agtgggtaca gaagatgtca | 180 |
| ggaaagggtt tgaaatggat tggctggatg aacacccagt ctgaagtgcc aaaatatgca | 240 |
| gaagagttca agggacggat tgccttctct ttggaaaccg ctgccagtac tgcatattta | 300 |
| cagataaaca acctcaaaac tgaggacacg gcaacgtatt tctgtgcgaa atcggtctat | 360 |
| tttaactgga gatatttcga tgtctggggt gcagggacca cggtcaccgt ctcctcagcc | 420 |
| aaaacgacac ccccacccgt ctatccactg gtc | 453 |

<210> SEQ ID NO 20
<211> LENGTH: 453
<212> TYPE: DNA
<213> ORGANISM: Artificial Sequence
<220> FEATURE:
<223> OTHER INFORMATION: Synthetic

<400> SEQUENCE: 20

| | |
|---|---|
| atggattggg tgtggaccttt gccattcctc atggcagcag ctcaaagtat ccaagcacag | 60 |
| atccagttgg tgcagtctgg acctgagctg aggaagcctg agagacagt caggatctcc | 120 |
| tgcaaggctt ctgggtatcc cttcacaact gctggattgc agtgggtaca gaagatgtca | 180 |
| ggaaagggtt tgaaatggat tggctggatg aacacccagt ctgaagtgcc aaaatatgca | 240 |
| gaagagttca agggacggat tgccttctct ttggaaaccg ctgccagtac tgcatattta | 300 |
| cagataaaca acctcaaaac tgaggacacg gcaacgtatt tctgtgcgaa atcggtctat | 360 |
| tttaactgga gatatttcga tgtctggggt gcagggacca cggtcaccgt ctcctcagcc | 420 |
| aaaacgacac ccccatctgt ctatccactg gcc | 453 |

<210> SEQ ID NO 21
<211> LENGTH: 453
<212> TYPE: DNA
<213> ORGANISM: Artificial Sequence
<220> FEATURE:
<223> OTHER INFORMATION: Synthetic

<400> SEQUENCE: 21

| | |
|---|---|
| atgggttggg tgtggaacttt gccattcctc atggcagcag ctcaaagtat ccaagcacag | 60 |
| atccagttgg tgcagtctgg acctgagctg aggaagcctg agagacagt caggatctcc | 120 |
| tgcaaggctt ctgggtatcc cttcacaact gctggattgc agtgggtaca gaagatgtca | 180 |
| ggaaagggtt tgaaatggat tggctggatg aacacccagt ctgaagtacc aaaatatgca | 240 |
| gaagagttca agggacggat tgccttctct ttggaaaccg ctgccagcac tgcatattta | 300 |
| cagataaaca acctcaaaac tgaggacacg gcaacgtatt tctgtgcgaa atcggtctat | 360 |
| tttaactgga gatatttcga tgtctggggt gcagggacca cggtcaccgt ctcctcagcc | 420 |
| aaaacgacac ccccacccgt ctatccattg gcc | 453 |

<210> SEQ ID NO 22
<211> LENGTH: 453
<212> TYPE: DNA
<213> ORGANISM: Artificial Sequence
<220> FEATURE:
<223> OTHER INFORMATION: Synthetic

<400> SEQUENCE: 22

| | |
|---|---|
| atggattggc tgtggaacttt gccattcctc atggcagcag ctcaaagtat ccaagcacag | 60 |
| atccagttgg tgcagtctgg acctgagctg aggaagcctg agagacagt caggatctcc | 120 |

```
tgcaaggctt ctgggtatcc cttcacaact gctggattgc agtgggtaca gaagatgtca        180
ggaaagggtt tgaaatggat tggctggatg aacacccagt ctgaagtgcc aaaatatgca        240
gaagagttca agggacggat tgccttctct ttggaaaccg ctgccagtac tgcatattta        300
cagataaaca acctcaaaac tgaggacacg gcaacgtatt tctgtgcgaa atcggtctat        360
tttaactgga gatatttcga tgtctggggt gcagggacca cggtcaccgt ctcctcagcc        420
aaaacgacac ccccacccgt ctatccactg gcc                                    453

<210> SEQ ID NO 23
<211> LENGTH: 453
<212> TYPE: DNA
<213> ORGANISM: Artificial Sequence
<220> FEATURE:
<223> OTHER INFORMATION: Synthetic

<400> SEQUENCE: 23
atgggttggg tgtggacctt gccattcctc atggcagcag ctcaaagtat ccaagcacag         60
atccagttgg tgcagtctgg acctgagctg aggaagcctg agagacagt caggatctcc        120 tgcaaggctt ctgggtatcc cttcacaact gctggattgc agtgggtaca gaagatgtca        180
ggaaagggtt tgaaatggat tggctggatg aacacccagt ctgaagtgcc aaaatatgca        240
gaagagttca agggacggat tgccttctct ttggaaaccg ctgccagtac tgcatattta        300
cagataaaca acctcaaaac tgaggacacg gcgacgtatt tctgtgcgaa atcggtctat        360
tttaactgga gatatttcga tgtctggggt gcagggacca cggtcaccgt ctcctcagcc        420
aaaacgacac ccccacccgt ctatccctg gtc                                     453

<210> SEQ ID NO 24
<211> LENGTH: 488
<212> TYPE: DNA
<213> ORGANISM: Artificial Sequence
<220> FEATURE:
<223> OTHER INFORMATION: Synthetic

<400> SEQUENCE: 24
atgagggccc ctgctcagtt tcttgggctt ttgcttctct ggacttcagc ctccagatgt         60
gacattgtga tgactcagtc tccagccacc ctgtctgtga ctccaggaga tagagtctct        120 cttcctgca gggccagcca gagtattagc gactacttat cctggtatca acaaagatct        180
catgagtctc caaggcttat catcaaatat gcttcccaat ccatctctgg gatcccctcc        240
aggttcagtg gcagtggatc agggtcagac ttcactctca gtatcaacag tgtggaacct        300
gaagatgttg gagtgtatta ctgtcaacat ggtcacagct ttccgctcac gttcggttct        360
gggaccaagc tggagctgaa acgggctgat gctgcaccaa ctgtatccat cttcccacca        420
tccagtgagc agttaacatc tggaggtgcc tcagtcgtgt gcttcttgaa caacttctac        480
cccaaaga                                                                488

<210> SEQ ID NO 25
<211> LENGTH: 486
<212> TYPE: DNA
<213> ORGANISM: Artificial Sequence
<220> FEATURE:
<223> OTHER INFORMATION: Synthetic

<400> SEQUENCE: 25
atgaggtccc ctgctcagtt ccttgggctt ttgcttttct ggacttcagc ctccagatgt         60
```

```
gacattgtga tgactcagtc tccagccacc ctgtctgtga ctccaggaga tagagtctct    120
ctttcctgca gggccagcca gagtattagc gactacttat cctggtatca acaaagatct    180
catgagtctc caaggcttat catcaaatat gcttcccaat ccatctctgg gatccctcc     240 aggttcagtg gcagtggatc agggtcagac ttcactctca gtatcaacag tgtggaacct    300
gaagatgttg gagtgtatta ctgtcaacat ggtcacagct ttccgctcac gttcggttct    360
gggaccaagc tggagctgaa acgggctgat gctgcaccaa ctgtatccat cttcccacca    420
tccagtgagc agttaacatc tggaggtgcc tcagtcgtgt gcttcttgaa caacttctac    480
cccaaa                                                                486

<210> SEQ ID NO 26
<211> LENGTH: 488
<212> TYPE: DNA
<213> ORGANISM: Artificial Sequence
<220> FEATURE:
<223> OTHER INFORMATION: Synthetic

<400> SEQUENCE: 26
atgaggtccc cagctcagtt tctggggctt ttgcttttct ggacttcagc ctccagatgt     60
gacattgtga tgactcagtc tccagccacc ctgtctgtga ctccaggaga tagagtctct    120
ctttcctgca gggccagcca gagtattagc gactacttat cctggtatca acaaagatct    180
catgagtctc caaggcttat catcaaatat gcttcccaat ccatctctgg gatccctcc     240 aggttcagtg gcagtggatc agggtcagac ttcactctca gtatcaacag tgtggaacct    300
gaagatgttg gagtgtatta ctgtcaacat ggtcacagct ttccgctcac gttcggttct    360
gggaccaagc tggagctgaa acgggctgat gctgcaccaa ctgtatccat cttcccacca    420
tccagtgagc agttaacatc tggaggtgcc tcagtcgtgt gcttcttgaa caacttctac    480
cccagaga                                                              488

<210> SEQ ID NO 27
<211> LENGTH: 488
<212> TYPE: DNA
<213> ORGANISM: Artificial Sequence
<220> FEATURE:
<223> OTHER INFORMATION: Synthetic

<400> SEQUENCE: 27
atgagggccc ctgctcagct cctggggctt ttgcttttct ggacttcagc ctccagatgt     60
gacattgtga tgactcagtc tccagccacc ctgtctgtga ctccaggaga tagagtctct    120
ctttcctgca gggccagcca gagtattagc gactacttat cctggtatca acaaagatct    180
catgagtctc caaggcttat catcaaatat gcttcccaat ccatctctgg gatccctcc     240 aggttcagtg gcagtggatc agggtcagac ttcactctca atatcaacag tgtggaacct    300
gaagatgttg gagtgtatta ctgtcaacat ggtcacagct ttccgctcac gttcggttct    360
gggaccaagc tggagctgaa acgggctgat gctgcaccaa ctgtatccat cttcccacca    420
tccagtgagc agttaacatc tggaggtgcc tcagtcgtgt gcttcttgaa caacttctat    480
cccaaaga                                                              488

<210> SEQ ID NO 28
<211> LENGTH: 486
<212> TYPE: DNA
<213> ORGANISM: Artificial Sequence
<220> FEATURE:
<223> OTHER INFORMATION: Synthetic]
```

<400> SEQUENCE: 28

```
atggtatcct cagctcagtt ccttggactt ttgcttttct ggacttcagc ctccagatgt      60
gacattgtga tgactcagtc tccagccacc ctgtctgtga ctccaggaga tagagtctct     120
ctttcctgca gggccagcca gagtattagc gactacttat cctggtatca acaaagatct     180
catgagtctc caaggcttat catcaaatat gcttcccaat ccatctctgg atcccctcc      240
aggttcagtg gcagtggatc agggtcagac ttcactctca gtatcaacag tgtggaacct     300
gaagatgttg gagtgtatta ctgtcaacat ggtcacagct ttccgctcac gttcggttct     360
gggaccaagc tggagctgaa acgggctgat gctgcaccaa ctgtatccat cttcccacca    420
tccagtgagc agttaacatc tggaggtgcc tcagtcgtgt gcttcttgaa caacttctac    480
cccaaa                                                                486
```

<210> SEQ ID NO 29
<211> LENGTH: 488
<212> TYPE: DNA
<213> ORGANISM: Artificial Sequence
<220> FEATURE:
<223> OTHER INFORMATION: Synthetic

<400> SEQUENCE: 29

```
atggtgtcca cagctcagtt ccttggactt ttgcttttct ggacttcagc ctccagatgt      60
gacattgtga tgactcagtc tccagccacc ctgtctgtga ctccaggaga tagagtctct     120
ctttcctgca gggccagcca gagtattagc gactacttat cctggtatca acaaagatct     180
catgagtctc caaggcttat catcaaatat gcttcccaat ccatctctgg atcccctcc      240
aggttcagtg gcagtggatc agggtcagac ttcactctca gtatcaacag tgtggaacct     300
gaagatgttg gagtgtatta ctgtcaacat ggtcacagct ttccgctcac gttcggttct     360
gggaccaagc tggagctgaa acgggctgat gctgcaccaa ctgtatccat cttcccacca    420
tccagtgagc agttaacatc tggaggtgcc tcagtcgtgt gcttcttgaa caacttctac    480
cccagaga                                                              488
```

<210> SEQ ID NO 30
<211> LENGTH: 24
<212> TYPE: PRT
<213> ORGANISM: Artificial Sequence
<220> FEATURE:
<223> OTHER INFORMATION: Synthetic

<400> SEQUENCE: 30

```
Glu Asp Tyr Pro Pro Gln Lys Gly Cys Ile Pro Leu Pro Arg Gly Gln
1               5                   10                  15

Thr Glu Lys Ala Asp His Val Asp
            20
```

<210> SEQ ID NO 31
<211> LENGTH: 19
<212> TYPE: PRT
<213> ORGANISM: Artificial Sequence
<220> FEATURE:
<223> OTHER INFORMATION: Synthetic

<400> SEQUENCE: 31

```
Gln Lys Gly Cys Ile Pro Leu Pro Arg Gly Gln Thr Glu Lys Ala Asp
1               5                   10                  15

His Val Asp
```

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

Gln Lys Gly Cys Ile Pro Leu Pro Arg Gly Gln Thr Glu Lys Ala
1               5                   10                  15

<210> SEQ ID NO 33
<211> LENGTH: 106
<212> TYPE: PRT
<213> ORGANISM: Artificial Sequence
<220> FEATURE:
<223> OTHER INFORMATION: Synthetic

<400> SEQUENCE: 33

Met Asn Phe Gly Leu Ser Leu Val Phe Leu Val Leu Val Leu Lys Gly
1               5                   10                  15

Ala Gln Cys Glu Val Gln Leu Val Glu Ser Gly Gly Gly Leu Val Lys
                20                  25                  30

Pro Gly Gly Ser Leu Lys Leu Ser Cys Ala Ala Ser Gly Phe Thr Phe
            35                  40                  45

Ser Asp Tyr Tyr Met Tyr Trp Val Arg Gln Thr Pro Glu Lys Arg Leu
        50                  55                  60

Glu Trp Val Ala Thr Ile Ser Asp Gly Gly Thr Tyr Thr Tyr Tyr Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Asn Ser Leu Lys
            100                 105

<210> SEQ ID NO 34
<211> LENGTH: 147
<212> TYPE: PRT
<213> ORGANISM: Artificial Sequence
<220> FEATURE:
<223> OTHER INFORMATION: Synthetic

<400> SEQUENCE: 34

Phe Leu Val Leu Val Leu Lys Gly Val Gln Cys Glu Val Gln Leu Val
1               5                   10                  15

Glu Ser Gly Gly Gly Leu Val Lys Pro Gly Gly Ser Leu Lys Leu Ser
                20                  25                  30

Cys Ala Ala Ser Gly Phe Thr Phe Ser Asp Tyr Tyr Met Tyr Trp Val
            35                  40                  45

Arg Gln Thr Pro Glu Lys Arg Leu Glu Trp Val Ala Thr Ile Ser Asp
        50                  55                  60

Gly Gly Thr Tyr Thr Tyr Tyr Pro Asp Ser Val Lys Gly Arg Phe Thr
65                  70                  75                  80

Ile Ser Arg Asp Asn Ala Lys Asn Asn Leu Tyr Leu Gln Met Asn Ser
                85                  90                  95

Leu Lys Ser Glu Asp Thr Ala Met Tyr Tyr Cys Ala Arg Gly Trp Val
            100                 105                 110

Ser Thr Met Val Lys Leu Leu Ser Ser Phe Pro Tyr Trp Gly Gln Gly
        115                 120                 125

```
Thr Leu Val Thr Val Ser Ala Ala Lys Thr Thr Pro Pro Ser Val Tyr
        130                 135                 140
Pro Leu Ala
145

<210> SEQ ID NO 35
<211> LENGTH: 155
<212> TYPE: PRT
<213> ORGANISM: Artificial Sequence
<220> FEATURE:
<223> OTHER INFORMATION: Synthetic

<400> SEQUENCE: 35

Met Asp Phe Gly Leu Ser Arg Val Phe Leu Val Leu Val Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Thr Ile Ser Asp Gly Gly Thr Tyr Thr Tyr Tyr Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Asn Ser Leu Lys Ser Glu Asp Thr Ala Met
            100                 105                 110

Tyr Tyr Cys Ala Arg Gly Trp Val Ser Thr Met Val Lys Leu Leu Ser
        115                 120                 125

Ser Phe Pro Tyr Trp Gly Gln Gly Thr Leu Val Thr Val Ser Ala Ala
    130                 135                 140

Lys Thr Thr Pro Pro Ser Val Tyr Pro Leu Ala
145                 150                 155

<210> SEQ ID NO 36
<211> LENGTH: 155
<212> TYPE: PRT
<213> ORGANISM: Artificial Sequence
<220> FEATURE:
<223> OTHER INFORMATION: Synthetic

<400> SEQUENCE: 36

Met Asp Phe Gly Leu Ser Trp Val Phe Leu Val Leu Val Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Thr Ile Ser Asp Gly Gly Thr Tyr Thr Tyr Tyr Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Asn Ser Leu Lys Ser Glu Asp Thr Ala Met
            100                 105                 110

Tyr Tyr Cys Ala Arg Gly Trp Val Ser Thr Met Val Lys Leu Leu Ser
        115                 120                 125
```

```
Ser Phe Pro Tyr Trp Gly Gln Gly Thr Leu Val Thr Val Ser Ala Ala
    130                 135                 140

Lys Thr Thr Pro Pro Ser Val Tyr Pro Leu Ala
145                 150                 155

<210> SEQ ID NO 37
<211> LENGTH: 149
<212> TYPE: PRT
<213> ORGANISM: Artificial Sequence
<220> FEATURE:
<223> OTHER INFORMATION: Synthetic

<400> SEQUENCE: 37

Met Ala Trp Ile Ser Leu Ile Phe Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Val Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn Tyr Trp Val Phe Gly Gly Gly Thr Lys Leu Thr Val Leu
        115                 120                 125

Gly Gln Pro Lys Ser Ser Pro Ser Val Thr Leu Phe Pro Pro Ser Thr
    130                 135                 140

Glu Glu Leu Ser Leu
145

<210> SEQ ID NO 38
<211> LENGTH: 149
<212> TYPE: PRT
<213> ORGANISM: Artificial Sequence
<220> FEATURE:
<223> OTHER INFORMATION: Synthetic

<400> SEQUENCE: 38

Met Ala Trp Ile Ser Leu Ile Phe Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Ser Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn Tyr Trp Val Phe Gly Gly Gly Thr Lys Leu Thr Val Leu
```

```
                        115                 120                 125
Gly Gln Pro Lys Ser Ser Pro Ser Val Thr Leu Tyr Pro Pro Ser Thr
        130                 135                 140

Lys Glu Leu Ser Leu
145

<210> SEQ ID NO 39
<211> LENGTH: 149
<212> TYPE: PRT
<213> ORGANISM: Artificial Sequence
<220> FEATURE:
<223> OTHER INFORMATION: Synthetic

<400> SEQUENCE: 39

Met Ala Trp Thr Ser Leu Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn Tyr Trp Val Phe Gly Gly Gly Thr Lys Leu Thr Val Leu
        115                 120                 125

Gly Gln Pro Lys Ser Ser Pro Ser Val Thr Leu Cys Pro Pro Ser Ser
    130                 135                 140

Glu Lys Leu Ser Leu
145

<210> SEQ ID NO 40
<211> LENGTH: 149
<212> TYPE: PRT
<213> ORGANISM: Artificial Sequence
<220> FEATURE:
<223> OTHER INFORMATION: Synthetic

<400> SEQUENCE: 40

Met Ala Trp Thr Ser Leu Leu Phe Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Ala Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110
```

```
Tyr Ser Asn Tyr Trp Val Phe Gly Gly Gly Thr Lys Leu Thr Val Leu
            115                 120                 125

Gly Gln Pro Lys Ser Ser Pro Ser Val Thr Leu Cys Pro Pro Ser Thr
    130                 135                 140

Glu Lys Leu Ser Leu
145

<210> SEQ ID NO 41
<211> LENGTH: 149
<212> TYPE: PRT
<213> ORGANISM: Artificial Sequence
<220> FEATURE:
<223> OTHER INFORMATION: Synthetic

<400> SEQUENCE: 41

Met Ala Trp Ile Pro Leu Leu Phe Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Ile Gly Ala Gln Thr Glu Asp Glu Ala Ile Tyr Phe Cys Ala Leu Trp
            100                 105                 110

Tyr Ser Asn Tyr Trp Val Phe Gly Gly Gly Thr Lys Leu Thr Val Leu
            115                 120                 125

Gly Gln Pro Lys Ser Ser Pro Ser Val Thr Leu Phe Pro Pro Ser Leu
    130                 135                 140

Glu Lys Leu Ser Leu
145

<210> SEQ ID NO 42
<211> LENGTH: 149
<212> TYPE: PRT
<213> ORGANISM: Artificial Sequence
<220> FEATURE:
<223> OTHER INFORMATION: Synthetic

<400> SEQUENCE: 42

Met Ala Trp Ile Ser Leu Leu Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110
```

Tyr Ser Asn Tyr Trp Val Phe Gly Gly Gly Thr Lys Leu Thr Val Leu
        115                 120                 125

Gly Gln Pro Lys Ser Ser Pro Ser Val Thr Leu Phe Pro Pro Ser Thr
    130                 135                 140

Glu Glu Leu Ser Leu
145

<210> SEQ ID NO 43
<211> LENGTH: 149
<212> TYPE: PRT
<213> ORGANISM: Artificial Sequence
<220> FEATURE:
<223> OTHER INFORMATION: Synthetic

<400> SEQUENCE: 43

Met Ala Trp Ile Ser Leu Leu Phe Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn Tyr Trp Val Phe Gly Gly Gly Thr Lys Leu Thr Val Leu
        115                 120                 125

Gly Gln Pro Lys Ser Ser Pro Ser Val Thr Leu Phe Pro Pro Ser Thr
    130                 135                 140

Glu Lys Leu Ser Leu
145

<210> SEQ ID NO 44
<211> LENGTH: 318
<212> TYPE: DNA
<213> ORGANISM: Artificial Sequence
<220> FEATURE:
<223> OTHER INFORMATION: Synthetic

<400> SEQUENCE: 44
atgaacttcg ggttgagctt ggttttcctt gtccttgttt taaaaggtgc ccagtgtgaa       60
gtgcagctgg tggagtctgg gggaggctta gtgaagcctg agggtccct gaaactctcc      120 tgtgcagcct ctggattcac tttcagtgac tattacatgt attgggttcg ccagactccg      180
gaaaagaggc tggagtgggt cgcaaccatt agtgatggtg gtacttacac ctactatcca      240
gacagtgtga agggcgatt caccatctcc agagacaatg ccaagaacaa cctttacctg      300
caaatgaaca gtctgaag                                                    318

<210> SEQ ID NO 45
<211> LENGTH: 465
<212> TYPE: DNA
<213> ORGANISM: Artificial Sequence
<220> FEATURE:
<223> OTHER INFORMATION: Synthetic

<400> SEQUENCE: 45

```
atggacttcg ggttgagctg ggttttcctt gtccttgttt taaaaggtgt ccagtgtgaa    60
gtgcagctgg tggagtctgg gggaggctta gtgaagcctg gagggtccct gaaactctcc   120
tgtgcagcct ctggattcac tttcagtgac tattacatgt attgggttcg ccagactccg   180
gaaaagaggc tggagtgggt cgcaaccatt agtgatggtg gtacttacac ctactatcca   240
gacagtgtga agggccgatt caccatctcc agagacaatg ccaagaacaa cctttacctg   300
caaatgaaca gtctgaagtc tgaggacaca gccatgtatt actgtgcaag aggatgggtt   360
tctactatgg ttaaacttct ttcctccttt ccttactggg gccaagggac tctggtcact   420
gtctctgcag ccaaaacgac accccatct gtctatccac tggcc                    465
```

<210> SEQ ID NO 46
<211> LENGTH: 465
<212> TYPE: DNA
<213> ORGANISM: Artificial Sequence
<220> FEATURE:
<223> OTHER INFORMATION: Synthetic

<400> SEQUENCE: 46

```
atggacttcg ggctgagcag ggttttcctt gtccttgttt taaaaggtgt ccagtgtgaa    60
gtgcagctgg tggagtctgg gggaggctta gtgaagcctg gagggtccct gaaactctcc   120
tgtgcagcct ctggattcac tttcagtgac tattacatgt attgggttcg ccagactccg   180
gaaaagaggc tggagtgggt cgcaaccatt agtgatggtg gtacttacac ctactatcca   240
gacagtgtga agggccgatt caccatctcc agagacaatg ccaagaacaa cctttacctg   300
caaatgaaca gtctgaagtc tgaggacaca gccatgtatt actgtgcaag aggatgggtt   360
tctactatgg ttaaacttct ttcctccttt ccttactggg gccaagggac tctggtcact   420
gtctctgcag ccaaaacgac accccatct gtctatccac tggcc                    465
```

<210> SEQ ID NO 47
<211> LENGTH: 465
<212> TYPE: DNA
<213> ORGANISM: Artificial Sequence
<220> FEATURE:
<223> OTHER INFORMATION: Synthetic

<400> SEQUENCE: 47

```
atggacttcg ggctgagctg ggttttcctt gtccttgttt taaaaggtgt ccagtgtgaa    60
gtgcagctgg tggagtctgg gggaggctta gtgaagcctg gagggtccct gaaactctcc   120
tgtgcagcct ctggattcac tttcagtgac tattacatgt attgggttcg ccagactccg   180
gaaaagaggc tggagtgggt cgcaaccatt agtgatggtg gtacttacac ctactatcca   240
gacagtgtga agggccgatt caccatctcc agagacaatg ccaagaacaa cctttacctg   300
caaatgaaca gtctgaagtc tgaggacaca gccatgtatt actgtgcaag aggatgggtt   360
tctactatgg ttaaacttct ttcctccttt ccttactggg gccaagggac tctggtcact   420
gtctctgcag ccaaaacgac accccatct gtctatccac tggcc                    465
```

<210> SEQ ID NO 48
<211> LENGTH: 443
<212> TYPE: DNA
<213> ORGANISM: Artificial Sequence
<220> FEATURE:
<223> OTHER INFORMATION: Synthetic

<400> SEQUENCE: 48

```
ttttccttgt ccttgtttta aaaggtgtcc agtgtgaagt gcagctggtg gagtctgggg      60
gaggcttagt gaagcctgga gggtccctga aactctcctg tgcagcctct ggattcactt     120
tcagtgacta ttacatgtat tgggttcgcc agactccgga aaagaggctg gagtgggtcg     180
caaccattag tgatggtggt acttacacct actatccaga cagtgtgaag ggcgattca      240
ccatctccag agacaatgcc aagaacaacc tttacctgca aatgaacagt ctgaagtctg     300
aggacacagc catgtattac tgtgcaagag gatgggtttc tactatggtt aaacttcttt    360
cctcctttcc ttactggggc caagggactc tggtcactgt ctctgcagcc aaaacgacac    420
ccccatctgt ctatccactg gcc                                             443
```

<210> SEQ ID NO 49
<211> LENGTH: 465
<212> TYPE: DNA
<213> ORGANISM: Artificial Sequence
<220> FEATURE:
<223> OTHER INFORMATION: Synthetic

<400> SEQUENCE: 49

```
atggacttcg ggctgagctg ggttttcctt gtccttgttt taaaaggtgt ccagtgtgaa      60
gtgcagctgg tggagtctgg gggaggctta gtgaagcctg agggtccct gaaactctcc     120
tgtgcagcct ctggattcac tttcagtgac tattacatgt attgggttcg ccagactccg    180
gaaaagaggc tggagtgggt cgcaaccatt agtgatggtg gtacttacac ctactatcca    240
gacagtgtga ggggcgatt caccatctcc agagacaatg ccaagaacaa cctttacctg    300
caaatgaaca gtctgaagtc tgaggacaca gccatgtatt actgtgcaag aggatgggtt    360
tctactatgg ttaaacttct ttcctccttt ccttactggg gccaagggac tctggtcact    420
gtctctgcag ccaaaacgac accccatct gtctatccac tggcc                     465
```

<210> SEQ ID NO 50
<211> LENGTH: 449
<212> TYPE: DNA
<213> ORGANISM: Artificial Sequence
<220> FEATURE:
<223> OTHER INFORMATION: Synthetic

<400> SEQUENCE: 50

```
atggcctgga tttctcttat attctctctc ctggctctca gctcaggggc catttcccag      60
gctgttgtga ctcaggaatc tgcactcacc acatcacctg gtgaaacagt cacactcact    120
tgtcgctcaa gtactggggc tgttacaact agtaactatg ccaactgggt ccaagaaaaa    180
ccagatcatt tattcactgg tctagtaggt ggtaccaaca accgagctcc aggtgttcct    240
gccagattct caggctccct gattggagac aaggctgccc tcaccatcac aggggcacag    300
actgaggatg aggcaatata tttctgtgct ctatggtaca gcaattattg ggtgttcggt    360
ggaggaacca aactgactgt cctaggccag cccaagtctt cgccatcagt caccctgttc    420
ccaccctcca ctgaagagct aagcttggg                                       449
```

<210> SEQ ID NO 51
<211> LENGTH: 449
<212> TYPE: DNA
<213> ORGANISM: Artificial Sequence
<220> FEATURE:
<223> OTHER INFORMATION: Synthetic

<400> SEQUENCE: 51

```
atggcctgga cttcactctt actctctctc ctggctctca gctcaggggc catttcccag    60
gctgttgtga ctcaggaatc tgcactcacc acatcacctg gtgaaacagt cacactcact   120
tgtcgctcaa gtactggggc tgttacaact agtaactatg ccaactgggt ccaagaaaaa   180
ccagatcatt tattcactgg tctaataggt ggtaccaaca accgagctcc aggtgttcct   240
gccagattct caggctccct gattggagac aaggctgccc tcaccatcac aggggcacag   300
actgaggatg aggcaatata tttctgtgct ctatggtaca gcaattattg ggtgttcggt   360
ggaggaacca aactgactgt cctaggccag cccaagtctt cgccatcagt caccctgtgc   420
ccgccctcct cagagaagct aagcttggg                                    449
```

<210> SEQ ID NO 52
<211> LENGTH: 449
<212> TYPE: DNA
<213> ORGANISM: Artificial Sequence
<220> FEATURE:
<223> OTHER INFORMATION: Synthetic

<400> SEQUENCE: 52

```
atggcctgga ttcctctttt attctctctc ctggctctca gctcaggggc catttcccag    60
gctgttgtga ctcaggaatc tgcactcacc acatcacctg gtgaaacagt cacactcact   120
tgtcgctcaa gtactggggc tgttacaact agtaactatg ccaactgggt ccaagaaaaa   180
ccagatcatt tattcactgg tctaataggt ggtaccaaca accgagctcc aggtgttcct   240
gccagattct caggctccct gattggagac aaggctgccc tcaccatcat aggggcacag   300
actgaggatg aggcaatata tttctgtgct ctatggtaca gcaattattg ggtgttcggt   360
ggaggaacca aactgactgt cctaggccag cccaagtctt cgccatcagt caccctgttc   420
ccgccctcct tagaaaagct tagcttggg                                    449
```

<210> SEQ ID NO 53
<211> LENGTH: 449
<212> TYPE: DNA
<213> ORGANISM: Artificial Sequence
<220> FEATURE:
<223> OTHER INFORMATION: Synthetic

<400> SEQUENCE: 53

```
atggcctgga tttcactttt actctctctc ctggctctca gctcaggggc catttcccag    60
gctgttgtga ctcaggaatc tgcactcacc acatcacctg gtgaaacagt cacactcact   120
tgtcgctcaa gtactggggc tgttacaact agtaactatg ccaactgggt ccaagaaaaa   180
ccagatcatt tattcactgg tctaataggt ggtaccaaca accgagctcc aggtgttcct   240
gccagattct caggctccct gattggagac aaggctgccc tcaccatcac aggggcacag   300
actgaggatg aggcaatata tttctgtgct ctatggtaca gcaattattg ggtgttcggt   360
ggaggaacca aactgactgt cctaggccag cccaagtctt cgccatcagt caccctgttt   420
ccaccctcca cagaagagct aagcttggg                                    449
```

<210> SEQ ID NO 54
<211> LENGTH: 449
<212> TYPE: DNA
<213> ORGANISM: Artificial Sequence
<220> FEATURE:
<223> OTHER INFORMATION: Synthetic

<400> SEQUENCE: 54

```
atggcctgga tttcacttat cttctctctc ctggctctca gtcaggggc catttcccag     60 gctgttgtga ctcaggaatc tgcactcacc acatcacctg gtgaaacagt cacactcact    120
tgtcgctcaa gtactggggc tgttacaact agtaactatg ccaactgggt ccaagaaaaa    180
ccagatcatt tattcactgg tctaataggt ggtaccagca accgagctcc aggtgttcct    240
gccagattct caggctccct gattggagac aaggctgccc tcaccatcac aggggcacag    300
actgaggatg aggcaatata tttctgtgct ctatggtaca gcaattattg ggtgttcggt    360
ggaggaacca aactgactgt cctaggccag cccaagtctt cgccatcagt caccctgtac    420 ccgcccctcta caaaggagct tagcttggg                                     449
```

<210> SEQ ID NO 55
<211> LENGTH: 449
<212> TYPE: DNA
<213> ORGANISM: Artificial Sequence
<220> FEATURE:
<223> OTHER INFORMATION: Synthetic

<400> SEQUENCE: 55

```
atggcctgga cttctctctt attctctctc ctggctctca gtcaggggc catttcccag     60 gctgttgtga ctcaggaatc tgcactcacc acatcacctg gtgaaacagt cacactcact    120
tgtcgctcaa gtactggggc tgttacaact agtaactatg ccaactgggt ccaagaaaaa    180
ccagatcatt tattcactgg tctaataggt ggtaccaaca accgagctcc aggtgctcct    240
gccagattct caggctccct gattggagac aaggctgccc tcaccatcac aggggcacag    300
actgaggatg aggcaatata tttctgtgct ctatggtaca gcaattattg ggtgttcggt    360
ggaggaacca aactgactgt cctaggccag cccaagtctt cgccatcagt caccctgtgc    420 ccgcccctcta cagaaaagct aagcttggg                                     449
```

<210> SEQ ID NO 56
<211> LENGTH: 708
<212> TYPE: DNA
<213> ORGANISM: Artificial Sequence
<220> FEATURE:
<223> OTHER INFORMATION: Synthetic

<400> SEQUENCE: 56

```
atggtcagct ctgctcaatt tctcggactc cttcttctgt gctttcaagg aacacgctgc     60
gatattgtga tgacccagtc ccccgccacc ctgtccgtga ctccgggcga ccgggtgtcc    120
ctgtcgtgcc gggcatcaca gagcatctcc gactacctgt cgtggtacca gcagagatca    180
cacgagagcc ctcgcctgat catcaaatac gccagccagt caatctccgg catcccctcg    240
cggttctccg gtccggttc cggctccgac ttcacactgt ccattaactc cgtggaacct    300
gaggacgtgg gagtgtacta ctgtcaacac ggccattcgt tcccgctgac tttcgggtcg    360
ggaaccaagc tggaattgaa gagggcggac gcggccccta ccgtgtcaat tttcccaccg    420
agctccgaac agctcaccag cggcggtgcc tcggtcgtgt gcttcctcaa caacttctat    480
ccaaaagaca ttaacgtcaa gtggaagatc gatggatcgg agagacagaa cggagtgctg    540
aacagctgga ctgatcagga ctccaaggat tcgacctact ccatgagctc cactctgacc    600
ctgaccaagg acgaatacga gcggcacaat tcctacactt gcgaagccac ccacaagacc    660
tcaacgtccc ccatcgtgaa gtccttcaac cgcaacgagt gttgataa                 708
```

<210> SEQ ID NO 57
<211> LENGTH: 234

```
<212> TYPE: PRT
<213> ORGANISM: Artificial Sequence
<220> FEATURE:
<223> OTHER INFORMATION: Synthetic

<400> SEQUENCE: 57

Met Val Ser Ser Ala Gln Phe Leu Gly Leu Leu Leu Leu Cys Phe Gln
1               5                   10                  15

Gly Thr Arg Cys Asp Ile Val Met Thr Gln Ser Pro Ala Thr Leu Ser
            20                  25                  30

Val Thr Pro Gly Asp Arg Val Ser Leu Ser Cys Arg Ala Ser Gln Ser
        35                  40                  45

Ile Ser Asp Tyr Leu Ser Trp Tyr Gln Gln Arg Ser His Glu Ser Pro
    50                  55                  60

Arg Leu Ile Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Ser Ile Asn
                85                  90                  95

Ser Val Glu Pro Glu Asp Val Gly Val Tyr Tyr Cys Gln His Gly His
            100                 105                 110

Ser Phe Pro Leu Thr Phe Gly Ser Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 58
<211> LENGTH: 2201
<212> TYPE: DNA
<213> ORGANISM: Artificial Sequence
<220> FEATURE:
<223> OTHER INFORMATION: Synthetic

<400> SEQUENCE: 58
atgggctgga ccctcgtgtt cctgttcctg ctgagcgtga cggcgggcgt gcactcccaa      60
atccagcttg tgcagtccgg acccgagctc aggaagccgg cgaaactgt gcgcatcagc     120 tgcaaggctt cagggtaccc tttcaccacc gccgggctgc aatgggtgca aagatgtcc     180 gggaagggtc tgaagtggat cggatggatg aacacccagt ccgaagtgcc taaatacgcc    240
gaagaattca agggccgcat tgcgttcagc ctggagacag ccgcctcgac cgcgtacctt    300
cagatcaaca atctcaagac tgaggacact gccacctact ctgtgccaa gagcgtgtac     360 ttcaactgga gatacttcga cgtgtggggc gccggaacca ccgtgaccgt gtccagcgcc    420
aagactaccg ccccgagcgt gtaccctctg gcgccagtgt gcggcgacac gactggcagc    480
tcggtgacct tgggctgcct cgtgaagggt tacttccccg agcccgtgac tctgacttgg    540
```

```
aactcgggct cactgtcgtc cggagtgcat accttccgg  ctgtgctgca aagcgacctc   600
tataccttgt catcgtccgt gactgtgacc tcctccacct ggccgtccca gagcatcacc   660
tgtaatgtcg cccaccctgc ttcatcgact aaggtcgaca agaagatcga gcccagagga   720
cctaccatca agcccgccc  gccctgcaaa tgcccggccc caaacttgct gggagggcct   780
tccgtgttca tcttccctcc gaaaatcaag gacgtgctga tgatctccct gagcccaatt   840
gtcacttgcg tggtggtgga tgtgtccgaa gatgacccag atgtgcagat tcatggttc   900 gtgaacaacg tcgaagtcca taccgcacag acccagaccc accgcgagga ttacaactcg   960
acgctgcgcg tcgtcagcgc cctgccgatt cagcaccagg attggatgag cggaaaggaa  1020
ttcaagtgca aagtcaacaa caaggacctt ccggcgccga tcgaacggac catctcgaag  1080
cctaagggat cagtgcgggc gcctcaggtc tacgtgctcc cgcctccgga agaggaaatg  1140
accaagaaac aagtcaccct gacttgcatg gtcaccgact tcatgcctga ggacatctat  1200
gtggagtgga ctaacaacgg aaagactgaa ctgaactaca aaacaccga accagtgctg  1260 gactctgacg gctcctactt catgtactcg aagctgcggg tggagaagaa aaactgggtg  1320
gaacgaaact cctactcgtg ttccgtggtg cacgagggtc tgcacaacca ccataccacc  1380
aagtccttct cccggacccc cggaaaggga tccgccgggg gatccggagg ggactccgaa  1440
gtgcaactgg tggagtcggg tggcggactc gtgaagcccg gggggtcatt gaagctttcc  1500
tgtgctgcct ccggtttcac tttctccgac tattacatgt actgggtcag acagaccccg  1560
gagaagcggc tcgaatgggt ggccaccatt tcggacggtg aacctacac  ttactaccct  1620 gactccgtca agggccggtt tactatctcc cgcgacaacg cgaagaacaa tctgtacctc  1680
caaatgaact ccctgaagtc cgaggacacc gccatgtact attgcgcaag gggatgggtc  1740
agcactatgg tcaagctgct gtcatccttc ccttactggg gacagggaac ccttgtgact  1800
gtgtcagccg gtggcggggg gtcggccggc ggcggttccg gtggaggggg atcccaggcc  1860
gtcgtgaccc aagagtcggc tctgactact tcacccggag aaaccgtgac cctgacatgc  1920
cgctcctcca ctggcgcagt gaccacgagc aattacgcca actgggtgca ggaaaagccc  1980
gatcacctgt tcactggact cattggggga accaacaacc gggcgccggg cgtgcccgct  2040
cggtttagcg gctccctgat tggagacaag gccgccctga ctatcaccgg agcccagacc  2100
gaagatgaag ccatctactt tgcgcactc  tggtactcta actactgggt gtttggcggc  2160
ggaaccaagc tgactgtgct cggacagccg aagtgataaa a                      2201
```

<210> SEQ ID NO 59
<211> LENGTH: 731
<212> TYPE: PRT
<213> ORGANISM: Artificial Sequence
<220> FEATURE:
<223> OTHER INFORMATION: Synthetic

<400> SEQUENCE: 59

```
Met Gly Trp Thr Leu Val Phe Leu Phe Leu Leu Ser Val Thr Ala Gly
1               5                   10                  15

Val His Ser Gln Ile Gln Leu Val Gln Ser Gly Pro Glu Leu Arg Lys
            20                  25                  30

Pro Gly Glu Thr Val Arg Ile Ser Cys Lys Ala Ser Gly Tyr Pro Phe
        35                  40                  45

Thr Thr Ala Gly Leu Gln Trp Val Gln Lys Met Ser Gly Lys Gly Leu
    50                  55                  60
```

```
Lys Trp Ile Gly Trp Met Asn Thr Gln Ser Glu Val Pro Lys Tyr Ala
 65                  70                  75                  80

Glu Glu Phe Lys Gly Arg Ile Ala Phe Ser Leu Glu Thr Ala Ala Ser
                 85                  90                  95

Thr Ala Tyr Leu Gln Ile Asn Asn Leu Lys Thr Glu Asp Thr Ala Thr
            100                 105                 110

Tyr Phe Cys Ala Lys Ser Val Tyr Phe Asn Trp Arg Tyr Phe Asp Val
        115                 120                 125

Trp Gly Ala Gly Thr Thr Val Thr Val Ser Ser Ala Lys Thr Thr Ala
    130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
    210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
                245                 250                 255

Leu Gly Gly Pro Ser Val Phe Ile Phe Pro Pro Lys Ile Lys Asp Val
            260                 265                 270

Leu Met Ile Ser Leu Ser Pro Ile Val Thr Cys Val Val Val Asp Val
        275                 280                 285

Ser Glu Asp Asp Pro Asp Val Gln Ile Ser Trp Phe Val Asn Asn Val
    290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Pro Ala
            340                 345                 350

Pro Ile Glu Arg Thr Ile Ser Lys Pro Lys Gly Ser Val Arg Ala Pro
        355                 360                 365

Gln Val Tyr Val Leu Pro Pro Pro Glu Glu Glu Met Thr Lys Lys Gln
    370                 375                 380

Val Thr Leu Thr Cys Met Val Thr Asp Phe Met Pro Glu Asp Ile Tyr
385                 390                 395                 400

Val Glu Trp Thr Asn Asn Gly Lys Thr Glu Leu Asn Tyr Lys Asn Thr
                405                 410                 415

Glu Pro Val Leu Asp Ser Asp Gly Ser Tyr Phe Met Tyr Ser Lys Leu
            420                 425                 430

Arg Val Glu Lys Lys Asn Trp Val Glu Arg Asn Ser Tyr Ser Cys Ser
        435                 440                 445

Val Val His Glu Gly Leu His Asn His His Thr Thr Lys Ser Phe Ser
    450                 455                 460

Arg Thr Pro Gly Lys Gly Ser Ala Gly Gly Ser Gly Gly Asp Ser Glu
465                 470                 475                 480

Val Gln Leu Val Glu Ser Gly Gly Gly Leu Val Lys Pro Gly Gly Ser
```

```
                    485                 490                 495
Leu Lys Leu Ser Cys Ala Ala Ser Gly Phe Thr Phe Ser Asp Tyr Tyr
            500                 505                 510

Met Tyr Trp Val Arg Gln Thr Pro Glu Lys Arg Leu Glu Trp Val Ala
        515                 520                 525

Thr Ile Ser Asp Gly Gly Thr Tyr Thr Tyr Tyr Pro Asp Ser Val Lys
    530                 535                 540

Gly Arg Phe Thr Ile Ser Arg Asp Asn Ala Lys Asn Asn Leu Tyr Leu
545                 550                 555                 560

Gln Met Asn Ser Leu Lys Ser Glu Asp Thr Ala Met Tyr Tyr Cys Ala
            565                 570                 575

Arg Gly Trp Val Ser Thr Met Val Lys Leu Leu Ser Ser Phe Pro Tyr
        580                 585                 590

Trp Gly Gln Gly Thr Leu Val Thr Val Ser Ala Gly Gly Gly Gly Ser
    595                 600                 605

Gly Gly Gly Gly Ser Gly Gly Gly Ser Gln Ala Val Val Thr Gln
610                 615                 620

Glu Ser Ala Leu Thr Thr Ser Pro Gly Glu Thr Val Thr Leu Thr Cys
625                 630                 635                 640

Arg Ser Ser Thr Gly Ala Val Thr Thr Ser Asn Tyr Ala Asn Trp Val
            645                 650                 655

Gln Glu Lys Pro Asp His Leu Phe Thr Gly Leu Ile Gly Gly Thr Asn
        660                 665                 670

Asn Arg Ala Pro Gly Val Pro Ala Arg Phe Ser Gly Ser Leu Ile Gly
    675                 680                 685

Asp Lys Ala Ala Leu Thr Ile Thr Gly Ala Gln Thr Glu Asp Glu Ala
690                 695                 700

Ile Tyr Phe Cys Ala Leu Trp Tyr Ser Asn Tyr Trp Val Phe Gly Gly
705                 710                 715                 720

Gly Thr Lys Leu Thr Val Leu Gly Gln Pro Lys
            725                 730

<210> SEQ ID NO 60
<211> LENGTH: 8
<212> TYPE: PRT
<213> ORGANISM: Artificial Sequence
<220> FEATURE:
<223> OTHER INFORMATION: Synthetic

<400> SEQUENCE: 60

Gly Tyr Pro Phe Thr Thr Ala Gly
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic

<400> SEQUENCE: 61

Met Asn Thr Gln Ser Glu Val Pro
1               5

<210> SEQ ID NO 62
<211> LENGTH: 13
<212> TYPE: PRT
<213> ORGANISM: Artificial Sequence
<220> FEATURE:
```

```
<223> OTHER INFORMATION: Synthetic

<400> SEQUENCE: 62

Ala Lys Ser Val Tyr Phe Asn Trp Arg Tyr Phe Asp Val
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Synthetic

<400> SEQUENCE: 63

Gln Ser Ile Ser Asp Tyr
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln His Gly His Ser Phe Pro Leu Thr
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic

<400> SEQUENCE: 65

Gly Phe Thr Phe Ser Asp Tyr Tyr
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

Ile Ser Asp Gly Gly Thr Tyr Thr
1               5

<210> SEQ ID NO 67
<211> LENGTH: 17
<212> TYPE: PRT
<213> ORGANISM: Artificial Sequence
<220> FEATURE:
<223> OTHER INFORMATION: Synthetic

<400> SEQUENCE: 67

Ala Arg Gly Trp Val Ser Thr Met Val Lys Leu Leu Ser Ser Phe Pro
1               5                   10                  15

Tyr

<210> SEQ ID NO 68
<211> LENGTH: 9
<212> TYPE: PRT
<213> ORGANISM: Artificial Sequence
```

```
<220> FEATURE:
<223> OTHER INFORMATION: Synthetic

<400> SEQUENCE: 68

Thr Gly Ala Val Thr Thr Ser Asn Tyr
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic

<400> SEQUENCE: 69

Ala Leu Trp Tyr Ser Asn Tyr Trp Val
1               5
```

BISPECIFIC ANTIBODY TARGETING IL-1R1 AND NLPR3

CROSS-REFERENCE TO RELATED APPLICATIONS

This application is a National Stage filing under 35 U.S.C. § 371 of International Application No. PCT/EP2019/074744, filed Sep. 16, 2019, which claims the benefit of United Kingdom Patent Application No. 1815045.8 filed Sep. 14, 2018, which applications are incorporated herein by reference.

TECHNICAL FIELD

The present invention relates to modulators of the NLRP3 inflammasome pathway, particularly antibodies and fragments thereof as well as aptamer molecules (small RNA/DNA molecules that can form secondary and tertiary structures capable of specifically binding proteins or other cellular targets), each of which have binding specificity for members of the NLRP3 inflammasome. In particular, the invention extends to use of such antibodies and aptamers, and their fragments, for the treatment and prevention of inflammatory diseases mediated by NLRP3 inflammasome signalling and activation, particularly inflammatory eye diseases such as glaucoma.

BACKGROUND ART

Inflammasomes are a group of protein complexes that recognize a large variety of inflammation inducing stimuli that include pathogen-associated molecular patterns (PAMPs) and danger associated molecular patterns (DAMPs). Different inflammasome complexes are known; among these, NLRP3 is the most studied inflammasome due to the large variety of signals that activate it, including LPS, bacterial toxins, dust, stress signals such as ATP, crystallized and particulate materials, cholesterol crystals, oxidised LDL, amyloid beta, prion protein fibrils and fibrillar alpha synuclein, shear stress, pressure.

The NLRP3 (nucleotide-binding oligomerization domain (NACHT)), leucine rich repeat (LRR) domain, and pyrin domain-containing protein 3 inflammasome is implicated in a number of infectious diseases and a plethora of degenerative inflammatory type diseases including Atherosclerosis, Diabetes, Inflammatory eye disease, other eye diseases such as dry eye syndrome, Glaucoma, Age related macular degeneration, Depression, Alzheimer's Disease, Parkinson's Disease, Inflammatory Bowel Diseases, Arthritic conditions such as Rheumatoid Arthritis, Ageing, Dermatological conditions and Cancer.

The main role of the NLRP3 protein is to sense danger signals or foreign material, and relay the signal to caspase 1 in turn activating the secretion of the pro-inflammatory cytokine IL-1β, which then initiates inflammation in an attempt to protect the body. IL-1β is the most studied of all cytokines because of its central role in the inflammatory process. Although it is useful for the body to activate IL-1β, in many diseases this inflammation can get out of control and be responsible for the pathogenesis of the disease. Most therapeutic strategies to date have concentrated on developing therapies against IL-1β to dampen the inflammation, but as we propose here, there are number of advantages of targeting the upstream controllers of this cytokine, namely the NLRP3 inflammasome.

The mechanism of activation is not yet fully understood, but the processing of IL-1β via the inflammasome has been demonstrated to involve two pathways. First, the NFκB pathway is activated by a DAMP or PAMP via Toll-like receptors (TLRs) and or CD36 receptors. This leads to the transcription and expression of the pro form of IL-1β and NLRP3.

A second signal is also thought to be required whereby purinergic receptor stimulation by a DAMP such as ATP leads to increases in intracellular calcium and cell swelling that results in potassium efflux from the cell, lysosomal destabilisation, membrane permeabillisation, mitochondrial damage and subsequent generation of reactive oxygen species, leading to NLRP3 activation. Other work has demonstrated that oxidized LDL cholesterol can indeed itself act as the two signals required for NLRP3 activation. In all studies, potassium efflux appears to be the sole common denominator for NLRP3 activation.

The NLRP3 protein subsequently interacts with ASC (apoptosis-associated speck-like protein) through homotypic interactions of the pyrin domain. ASC then interacts with pro caspase 1 resulting in cleavage and activation of caspase 1, which in turn cleaves pro IL-1β to its active form. IL-1β is then cleaved to produce the biologically active and secreted form.

The current best treatments for inflammasome-related disorders target the main product of inflammasome activity, IL-1β. In the past 20 years, a number of anti-IL-1β therapies have been developed. However, there are several disadvantages of anti-IL-1β therapies. Host defence against opportunistic organisms as well as routine bacterial infections have become a major concern for all anti-cytokine agents because of the indolent and dangerous nature of these infections. Anti-IL-1β therapies have other side effects such as nausea, neutrophilia and adverse allergic responses.

Some advantages of an anti-NLRP3 therapy over the IL-1β therapies are as follows: NLRP3 is a nod like receptor so dampening the recognition of the root cause of a disease, i.e. recognition of the foreign/danger material may be advantageous over dampening the response. This would mean that no IL-1β would be secreted via the NLRP3 pathway activated by disease specific stimuli, e.g. oxidized LDL, p amyloid or alpha synuclein or a particular pathogen. However, IL-1β could still be activated via other pathways in response to other non-disease-related stimuli as needed in extreme circumstances (such as large scale or opportunistic infections), since there are other pathways responsible for IL-1β activation.

The inflammasome has been associated with specialized forms of cell death, pyronecrosis (caspase1 independent) and pyroptosis, which may occur in cases of exacerbated inflammation. Therefore, an anti-NLRP3 therapy will also decrease such death pathways, which have been evidenced to be involved in the pathogenesis of certain diseases such as atherosclerosis. Pyroptosis is a risk factor for plaque disruption in this disease in response to oxidized LDL.

Several previously characterized small molecule inhibitors have more recently also been shown to affect NLRP3 inflammasome function. Glyburide, a sulfonylurea drug, is an example of such an inhibitor. MCC950 (illustrated below) is another example of a specific small molecule inhibitor of NLRP3 inflammasome:

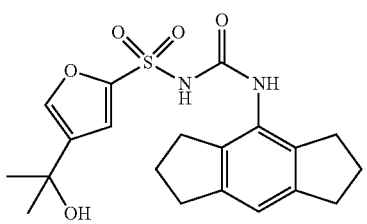 [SMILES: CC(C)(O)c1coc(S(=O)(=O)SC(=O)Nc2c3c(cc4c2CCC4)CCC3)c1]

However, there are several problems with currently available inhibitors. Indeed many of these currently available inhibitors of inflammasome function have either not been clinically successful, are nonspecific and importantly have very short half lives.

The development of humanized antibody type therapy could prove more advantageous than small molecule inhibitors for the NLRP3 inflammasome.

Some advantages of humanized antibodies over small molecule inhibitors are as follows:
- Non-recognition by the human immune system.
- A longer half-life in the circulation than non-human antibodies.
- Higher specificity than small-molecule inhibitors.
- Interact with challenging targets which have thus far eluded small molecule drugs. The best examples of this are protein-protein interactions which are characterised by large and often flat surfaces with few charged pockets.
- Chimeric and humanized mAbs, which have been the predominant mAbs entering clinical studies, have higher approval success rates (18% and 24%, respectively) than new chemical entities (NCEs) including small-molecule agents (5%), especially in the field of oncology.
- The commercial potential of biologics is very promising. The share of biologics in total sales of prescription and over-the-counter medicines grew from 12% in 2004 to 19% in 2011. More interestingly biologic products accounted for 17% of sales of the top 100 pharma products in 2004; 34% in 2011. The global biologics market is estimated to reach nearly $4bn by 2025.
- Biologics appear to be delivering a better overall economic return than small molecule drugs.
- Studies also show that the rate of attrition for biologics is less than that for small molecules. It has been reported that 24.4% of biologics that enter preclinical testing eventually reach the market compared with a success rate of only 7.1% for small molecule drugs.
- Biologics performed better than small molecules at all stages of development with an astonishing 116% rate of success at Phase 2.

NLRP3 (also known as NALP3 and cryopyrin) is a cytosolic protein; therefore, in order to target this protein, any therapy must gain entry to the cell. Humanized antibodies are quite large in size and entry to the cytosol may prove difficult. Small antibody fragment development also present a possibility to overcome such a challenge where an antibody fragment may be a Fab fragment, which is the antigen-binding fragment of an antibody, or a single-chain variable fragment, which is a fusion protein of the variable region of heavy and the light chain of an antibody connected by a peptide linker. As discussed further below, the present inventor has devised additional strategies to ensure the therapeutic antibody or aptamer, and their fragments, can gain entry to the cell.

There are some reports in the field describing the targeting of the NLRP3 inflammasome or related molecules using various agents. For example, WO2013/007763A1 discloses an inhibitor capable of intracellular localisation and cytosolic binding to a member of the inflammasome group including NLRP3, for use in a method for the prevention/treatment of acne.

US20080008652A1 discloses methods and compositions for modulating immune responses and adjuvant activity, and in particular, via modulation of cryopyrin (NPRL3) signalling. Humanized antibodies that target cryopyrin modulating proteins, or cryopyrin signal pathway components, are mentioned, and methods of producing cryopyrin antibodies are disclosed.

WO2002026780A2 discloses antibodies that bind to PAAD-domain containing polypeptides, as well as methods of treating various pathologies, including inflammation, by administering an anti-PAAD antibody. Single chain antibodies, chimeric, bifunctional and humanized antibodies, as well as antigen-binding fragments thereof are also mentioned.

WO2011109459A2 discloses a method of treating an inflammatory disease of skin/hair by providing a composition including at least one antibody that specifically binds to a component(s) of a mammalian inflammasome, such as ASC or NLRP1. Commercially available antibodies to ASC and NPRL1 are mentioned.

EP2350315B1 discloses methods and kits for the early diagnosis of atherosclerosis, involving the measurement of the expression levels of NLRP3, ASC and/or caspase-1. Expression levels may be measured by methods involving antibodies, including human antibodies, humanized antibodies, recombinant antibodies and antibody fragments, which in turn include Fab, Fab', F(ab)2, F(ab')2, Fv and scFv.

WO2013119673A1 discloses a method of evaluating a patient suspected of having a CNS injury comprising measuring the level of at least one inflammasome protein such as NLRP1 (NALP-1), ASC, and caspase-1. Commercially available antibodies to NPRL-1, ASC and caspase-1 are mentioned.

WO2007077042A1 discloses a method for the treatment of gout or pseudogout, comprising administering a NALP3 inflammasome inhibiting agent. The NALP3 inflammasome inhibiting agents are described as acting downstream of the NALP3 inflammasome and selected from among antibodies that inhibit the activity of IL-1.

WO2013138795A1 discloses a fusion protein comprising a Surf+ Penetrating Polypeptide and an antibody or antibody-mimic moiety (AAM moiety) that binds to an intracellular target, wherein the fusion protein penetrates cells and binds to the intracellular target to inhibit binding between the target and another protein inside the cells.

The present invention provides novel and effective modulators of the NLRP3 inflammasome for the treatment and prevention of inflammatory diseases mediated by NLRP3 inflammasome signalling and activation, particularly inflammatory eye diseases such as glaucoma. Such modulators include a bi-antibody or aptamer, and their fragments, targeted to both of IL-1 R1 and NLRP3. The bi-antibody first gains entry into the cell by binding to the IL-1 R1 which triggers rapid internalisation and, once internalised, the bi-antibody then targets the intracellular protein NLRP3 inhibiting the assembly of the NLRP3 inflammasome, in turn preventing IL-1 secretion from the cells, and reducing the initiation/amplification of inflammation.

SUMMARY OF THE INVENTION

Accordingly, in a first aspect of the present invention, there is provided an NLRP3 inflammasome modulator which is capable of binding to both of IL-1 R1 and NLRP3 for use in the treatment or prophylaxis of an inflammatory eye disease.

Optionally, the inflammatory eye disease is glaucoma.

Optionally, the modulator is also capable of binding to the PYD domain of NLRP3.

Optionally, the modulator is selected from the group comprising: a polyclonal antibody, a monoclonal antibody, a humanized antibody, a chimeric antibody, a fusion protein, or an aptamer molecule, a combination thereof, and fragments of each thereof.

The modulator may be a bi-antibody capable of binding to both of: IL-1 R1 and NLRP3. Optionally, the modulator is a recombinant humanized bi-antibody capable of binding to both of: IL-1 R1 and NLRP3.

Optionally, the modulator is a bi-antibody comprising one or more of the binding regions of a first antibody capable of binding IL-1 R1 and one or more of the binding regions of a second antibody capable of binding NLRP3. Optionally, the modulator is a bi-antibody comprising one or more complementary determining regions (CDRs) of a first antibody capable of binding IL-1 R1 and one or more CDRs of a second antibody capable of binding NLRP3. Optionally, the first and/or second antibody is a monoclonal antibody.

Optionally, the modulator is selected from an antibody fragment capable of binding to both: IL-1 R1 and NLRP3. Optionally, the antibody fragment is selected from one or more of Fab, Fv, Fab', (Fab')2, scFv, bis-scFv, minibody, Fab2, and Fab3.

Optionally, the modulator is selected from a recombinant humanized antibody or antibody fragment capable of binding to both of: IL-1 R1 and NLRP3.

Optionally, the modulator is an antibody or antibody fragment raised against one or more antigens selected from both of IL-1 R1 and NLRP3. Optionally, the modulator is raised against one or more antigens selected from all or part of both of IL-1 R1 and NLRP3. Optionally, the modulator is raised against one or more antigens selected from NLRP3, optionally conjugated to a carrier protein such as Keyhole Limpet Haemocyanin (KLH) (hereinafter, the NLRP3 immunogen), and IL-1 R1, optionally recombinant IL-1 R1.

Optionally, the extracellular domain of IL-1 R1 (hereinafter, the IL-1 R1 immunogen) comprises the sequence:

(SEQ ID NO: 1)
MKVLLRLICFIALLISSLEADKCKEREEKIILVSSANEIDVRPCPLNPN

EHKGTITWYKDDSKTPVSTEQASRIHQHKEKLWFVPAKVEDSGHYYCVV

RNSSYCLRIKISAKFVENEPNLCYNAQAIFKQKLPVAGDGGLVCPYMEF

FKNENNELPKLQWYKDCKPLLLDNIHFSGVKDRLIVMNVAEKHRGNYTC

HASYTYLGKQYPITRVIEFITLEENKPTRPVIVSPANETMEVDLGSQIQ

LICNVTGQLSDIAYWKWNGSVIDEDDPVLGEDYYSVENPANKRRSTLIT

VLNISEIESRFYKHPFTCFAKNTHGIDAAYIQLIYPVTNFQKLEGGPSV

FIFPPNIKDVLMISLTPKVTCVVVDVSEDDPDVQISWFVNNVEVHTAQT

QTHREDYNSTIRVVSHLPIQHQDWMSGKEFKCKVNNKDLPSPIERTISK

PKGLVRAPQVYTLPPPAEQLSRKDVSLTCLVVGFNPGDISVEWTSNGHT

EENYKDTAPVLDSDGSYFIYSKLNMKTSKWEKTDSFSCNVRHEGLKNYY

LKKTISRSPGK*.
(* or ** denotes a stop codon throughout this specification).

Optionally, the NLRP3 immunogen comprises the sequence:

(SEQ ID NO: 30)
EDYPPQKGCIPLPRGQTEKADHVD.

Optionally, the NLRP3 immunogen comprises a carrier protein conjugated to the sequence EDYPPQKGCIPL-PRGQTEKADHVD (SEQ ID NO: 30), optionally conjugated to the N-terminal end of the sequence EDYPPQKG-CIPLPRGQTEKADHVD (SEQ ID NO: 30).

A carrier protein, conjugated to a peptide, is known in the art to help the peptide generate a stronger immune response. Optionally, the carrier protein is KLH.

Optionally, the carrier protein is conjugated to the sequence EDYPPQKGCIPLPRGQTEKADHVD (SEQ ID NO: 30) via a linker, optionally the linker is Hydrazide-Ahx.

Optionally, the NLRP3 immunogen is:

(SEQ ID NO: 30)
KLH-Hydrazide-Ahx-EDYPPQKGCIPLPRGQTEKADHVD.

As is understood in the art, a hydrazide is a class of organic compounds characterized by a nitrogen-nitrogen covalent bond with four substituents with at least one of them being an acyl group. Ahx denotes a 6-carbon linear aminohexanoic linker.

Optionally, the modulator is raisable, optionally raised, against one or more immunogens selected from NLRP3 immunogen and IL-1 R1 immunogen, wherein the IL-1 R1 immunogen comprises the sequence:

(SEQ ID NO: 1)
MKVLLRLICFIALLISSLEADKCKEREEKIILVSSANEIDVRPCPLNPN

EHKGTITWYKDDSKTPVSTEQASRIHQHKEKLWFVPAKVEDSGHYYCVV

RNSSYCLRIKISAKFVENEPNLCYNAQAIFKQKLPVAGDGGLVCPYMEF

FKNENNELPKLQWYKDCKPLLLDNIHFSGVKDRLIVMNVAEKHRGNYTC

HASYTYLGKQYPITRVIEFITLEENKPTRPVIVSPANETMEVDLGSQIQ

LICNVTGQLSDIAYWKWNGSVIDEDDPVLGEDYYSVENPANKRRSTLIT

VLNISEIESRFYKHPFTCFAKNTHGIDAAYIQLIYPVTNFQKLEGGPSV

FIFPPNIKDVLMISLTPKVTCVVVDVSEDDPDVQISWFVNNVEVHTAQT

QTHREDYNSTIRVVSHLPIQHQDWMSGKEFKCKVNNKDLPSPIERTISK

PKGLVRAPQVYTLPPPAEQLSRKDVSLTCLVVGFNPGDISVEWTSNGHT

EENYKDTAPVLDSDGSYFIYSKLNMKTSKWEKTDSFSCNVRHEGLKNYY

LKKTISRSPGK*.
(* denotes a stop codon)

and the NLRP3 immunogen comprises the sequence:

```
                                              (SEQ ID NO: 30)
    KLH-Hydrazide-Ahx-EDYPPQKGCIPLPRGQTEKADHVD.
```

Optionally, the modulator is a bi-antibody comprising one or more of the binding regions of a first antibody raisable, optionally raised, against IL-1 R1 immunogen and comprising the sequence:

```
                                               (SEQ ID NO: 1)
MKVLLRLICFIALLISSLEADKCKEREEKIILVSSANEIDVRPCPLNPNE

HKGTITWYKDDSKTPVSTEQASRIHQHKEKLWFVPAKVEDSGHYYCVVRN

SSYCLRIKISAKFVENEPNLCYNAQAIFKQKLPVAGDGGLVCPYMEFFKN

ENNELPKLQWYKDCKPLLLDNIHFSGVKDRLIVMNVAEKHRGNYTCHASY

TYLGKQYPITRVIEFITLEENKPTRPVIVSPANETMEVDLGSQIQLICNV

TGQLSDIAYWKWNGSVIDEDDPVLGEDYYSVENPANKRRSTLITVLNISE

IESRFYKHPFTCFAKNTHGIDAAYIQLIYPVTNFQKLEGGPSVFIFPPNI

KDVLMISLTPKVTCVVVDVSEDDPDVQISWFVNNVEVHTAQTQTHREDYN

STIRVVSHLPIQHQDWMSGKEFKCKVNNKDLPSPIERTISKPKGLVRAPQ

VYTLPPPAEQLSRKDVSLTCLVVGFNPGDISVEWTSNGHTEENYKDTAPV

LDSDGSYFIYSKLNMKTSKWEKTDSFSCNVRHEGLKNYYLKKTISRSPGK

*,
(*denotes a stop codon)
``` and one or more of the binding regions of a second antibody raised against NLRP3 immunogen comprising the sequence:

```
                                              (SEQ ID NO: 30)
    KLH-Hydrazide-Ahx-EDYPPQKGCIPLPRGQTEKADHVD.
```

Optionally, the modulator is a bi-antibody comprising one or more complementary determining regions (CDRs) of a first antibody raisable, optionally raised, against IL-1 R1 immunogen and comprising the sequence:

```
                                               (SEQ ID NO: 1)
MKVLLRLICFIALLISSLEADKCKEREEKIILVSSANEIDVRPCPLNPNE

HKGTITWYKDDSKTPVSTEQASRIHQHKEKLWFVPAKVEDSGHYYCVVRN

SSYCLRIKISAKFVENEPNLCYNAQAIFKQKLPVAGDGGLVCPYMEFFKN

ENNELPKLQWYKDCKPLLLDNIHFSGVKDRLIVMNVAEKHRGNYTCHASY

TYLGKQYPITRVIEFITLEENKPTRPVIVSPANETMEVDLGSQIQLICNV

TGQLSDIAYWKWNGSVIDEDDPVLGEDYYSVENPANKRRSTLITVLNISE

IESRFYKHPFTCFAKNTHGIDAAYIQLIYPVTNFQKLEGGPSVFIFPPNI

KDVLMISLTPKVTCVVVDVSEDDPDVQISWFVNNVEVHTAQTQTHREDYN

STIRVVSHLPIQHQDWMSGKEFKCKVNNKDLPSPIERTISKPKGLVRAPQ

VYTLPPPAEQLSRKDVSLTCLVVGFNPGDISVEWTSNGHTEENYKDTAPV

LDSDGSYFIYSKLNMKTSKWEKTDSFSCNVRHEGLKNYYLKKTISRSPGK

*,
(*denotes a stop codon)
``` and one or more CDRs of a second antibody raised against NLRP3 immunogen comprising the sequence:

```
                                              (SEQ ID NO: 30)
    KLH-Hydrazide-Ahx-EDYPPQKGCIPLPRGQTEKADHVD.
```

Optionally, the first and/or second antibody is a monoclonal antibody.

Optionally, the consensus sequence of the heavy chain of the first antibody (to IL-1 R1) is

```
                                               (SEQ ID NO: 7)
MGWVWNLPFLMAAAQSIQAQIQLVQSGPELRKPGETVRISCKASGYPFTT

AGLQINVQKMSGKGLKWIGWMNTQSEVPKYAEEFKGRIAFSLETAASTAY

LQINNLKTEDTATYFCAKSVYFNWRYFDVWGAGTTVTVSSAKTTPPPVYP

LA.
```

Optionally, the heavy chain CDRs of the first antibody comprise: GYPFTTAG (SEQ ID NO: 60); MNTQSEVP (SEQ ID NO: 61); and AKSVYFNWRYFDV (SEQ ID NO: 62).

Optionally, the consensus sequence of the light chain of the first antibody (to IL-1 R1) is

```
                                              (SEQ ID NO: 12)
MRSPAQFLGLLLFWTSASRCDIVMTQSPATLSVTPGDRVSLSCRASQSIS

DYLSWYQQRSHESPRLIIKYASQSISGIPSRFSGSGSGSDFTLSINSVEP

EDVGVYYCQHGHSFPLTFGSGTKLELKRADAAPTVSIFPPSSEQLTSGGA

SVVCFLNNFYPK.
```

Optionally, the light chain CDRs of the first antibody comprise: QSISDY (SEQ ID NO: 63); YAS; and QHGHSFPLT (SEQ ID NO: 64).

Optionally, the consensus sequence of the heavy chain of the second antibody (against NLRP3) is

```
                                              (SEQ ID NO: 36)
MDFGLSWVFLVLVLKGVQCEVQLVESGGGLVKPGGSLKLSCAASGFTFSD

YYMYWVRQTPEKRLEWVATISDGGTYTYYPDSVKGRFTISRDNAKNNLYL

QMNSLKSEDTAMYYCARGWVSTMVKLLSSFPYWGQGTLVTVSAAKTTPPS

VYPLA.
```

Optionally, the heavy chain CDRs of the second antibody comprise: GFTFSDYY (SEQ ID NO: 65); ISDGGTYT (SEQ ID NO: 66); and ARGWVSTMVKLLSSFPY (SEQ ID NO: 67).

Optionally, the consensus sequence of the light chain of the second antibody (to NLRP3) is

```
                                              (SEQ ID NO: 43)
MAWISLLLSLLALSSGAISQAVVTQESALTTSPGETVTLTCRSSTGAVTT

SNYANWVQEKPDHLFTGLIGGTNNRAPGVPARFSGSLIGDKAALTITGAQ

TEDEAIYFCALWYSNYWVFGGGTKLTVLGQPKSSPSVTLFPPSTEELSL.
```

Optionally, the light chain CDRs of the second antibody comprise: TGAVTTSNY (SEQ ID NO: 68); GTN; and ALWYSNYWV (SEQ ID NO: 69).

Optionally, the modulator is capable of binding simultaneously to IL-1 R1 and NLRP3. Optionally, or additionally, the modulator is capable of binding sequentially to IL-1 R1 and NLRP3.

Optionally, the light chain of a bi-specific antibody of the present invention has the amino acid sequence:

(SEQ ID NO: 57)
MVSSAQFLGLLLLCFQGTRCDIVMTQSPATLSVTPGDRVSLSCRASQSIS

DYLSWYQQRSHESPRLIIKYASQSISGIPSRFSGSGSGSDFTLSINSVEP

EDVGVYYCQHGHSFPLTFGSGTKLELKRADAAPTVSIFPPSSEQLTSGGA

SVVCFLNNFYPKDINVKWKIDGSERQNGVLNSWTDQDSKDSTYSMSSTLT

LTKDEYERHNSYTCEATHKTSTSPIVKSFNRNEC**.

Optionally, the heavy chain of a bi-specific antibody of the present invention has the amino acid sequence:

(SEQ ID NO: 59)
MGWTLVFLFLLSVTAGVHSQIQLVQSGPELRKPGETVRISCKASGYPFTT

AGLQWVQKMSGKGLKWIGWMNTQSEVPKYAEEFKGRIAFSLETAASTAYL

QINNLKTEDTATYFCAKSVYFNWRYFDVWGAGTTVTVSSAKTTAPSVYPL

APVCGDTTGSSVTLGCLVKGYFPEPVTLTWNSGSLSSGVHTFPAVLQSDL

YTLSSSVTVTSSTWPSQSITCNVAHPASSTKVDKKIEPRGPTIKPCPPCK

CPAPNLLGGPSVFIFPPKIKDVLMISLSPIVTCVVVDVSEDDPDVQISWF

VNNVEVHTAQTQTHREDYNSTLRVVSALPIQHQDWMSGKEFKCKVNNKDL

PAPIERTISKPKGSVRAPQVYVLPPPEEEMTKKQVTLTCMVTDFMPEDIY

VEWTNNGKTELNYKNTEPVLDSDGSYFMYSKLRVEKKNWVERNSYSCSVV

HEGLHNHHTTKSFSRTPGKGSAGGSGGDSEVOLVESGGGLVKPGGSLKLS

CAASGFTFSDYYMYWVRQTPEKRLEWVATISDGGTYTYYPDSVKGRFTIS

RDNAKNNLYLQMNSLKSEDTAMYYCARGWVSTMVKLLSSFPYWGQGTLVT

VSAGGGGSGGGGSGGGGSQAVVTQESALTTSPGETVTLTCRSSTGAVTTS

NYANWVQEKPDHLFTGLIGGTNNRAPGVPARFSGSLIGDKAALTITGAQT

EDEAIYFCALWYSNYWVFGGGTKLTVLGQPK**.

By "binding simultaneously" to both of IL-1 R1 and NLRP3, it is meant that the modulator is capable of binding to each of IL-1 R1 and/or NLRP3, whether said IL-1R1 and/or NLRP3 are formed as a complex, or whether they are not formed as a complex.

In a second aspect, the invention provides an NLRP3 inflammasome modulator as defined herein in relation to the first aspect of the invention for use in the treatment or prophylaxis of an inflammation-related disorder, optionally an inflammatory eye disease, such as glaucoma, as described in the first aspect of the invention, in which the NLRP3 inflammasome is known to play a key role in the disease pathogenesis.

An advantage of the bispecific antibody as the modulator is that it can be used at lower, and thus less toxic, concentrations than single antibodies, therefore, reducing cytotoxicity potential. Being bi-specific allows for a more stable antibody with greater purity.

Being a biological has a longer half live thus confers a major advantage over small molecule inhibitors.

In a third aspect, the present invention provides a method for the treatment and/or prophylaxis of an inflammation-related disorder, optionally an inflammatory eye disease, such as glaucoma, the method comprising the steps of:
providing a therapeutically effective amount of an NLRP3 inflammasome modulator as defined herein in relation to the first aspect of the invention which suppresses activation and/or signalling of the NLRP3 inflammasome, and
administering the therapeutically effective amount of said compound to a subject in need of such treatment.

In a fourth aspect, the present invention provides for use of an NLRP3 inflammasome modulator as defined herein in relation to the first aspect of the invention in the preparation of a medicament for the treatment of an inflammation-related disorder, optionally an inflammatory eye disease, such as glaucoma.

In a fifth aspect, the present invention provides a method to reduce or prevent or treat at least one symptom of an inflammation-related disorder, optionally an inflammatory eye disease, such as glaucoma, in a subject comprising selectively inhibiting and/or reducing activation of the inflammasome pathway by the use of an NLRP3 inflammasome modulator as defined herein in relation to the first aspect of the invention.

Optionally, the modulator is for use in the treatment or prevention of at least one symptom of an inflammation-related disorder in a subject comprising selectively inhibiting and or reducing activation of the inflammasome pathway by the use of the modulator.

Optionally, the light chain of a bi-specific antibody has the amino acid sequence of SEQ ID NO: 57 and the heavy chain of a bi-specific antibody the amino acid sequence of SEQ ID NO: 59 and may be referred to herein as InflaMab or Inflamab.

Optionally, InflaMab may have disease modifying effects in systemic conditions such as but not limited to Atherosclerosis, whereby it prevents/inhibits inflammation therefore preventing plaque build up and/or plaque rupture thus reducing risk of myocardial infarction.

Optionally, InflaMab may have disease modifying effects in eye diseases such as but not limited to Glaucoma, whereby it prevents/inhibits inflammation, reduces intraocular pressure and/or prevents loss of retinal ganglion cells and axons, protecting the optic nerve and preserving visual acuity, and/or preventing blindness.

Optionally, InflaMab may have disease modifying effects in neurological conditions such as but not limited to Alzheimer's Disease, whereby it prevents/inhibits inflammation, reduces/inhibits amyloid plaque load, and/or prevents of cognitive dysfunction.

The modulator as defined herein may have utility in individuals with multi-morbidities or co-morbidities associated with inflammation.

Optionally, the modulator as defined in relation to of any of the aforementioned aspects of the invention, denoted as Inflamab, is a 210 kiloDalton (kDa) bispecific mouse antibody composed of two pairs of light chain and two pairs of heavy chains with scFv domains fused to the N-terminal, complexed together via disulphide bonds.

As used herein, an "inflammation-related disorder" includes, but is not limited to, Atherosclerosis, inflammatory eye conditions such as Age-Related Macular degeneration, Dry Eye Syndrome, Glaucoma, Sjogren's syndrome, Diabetes, Inflammatory eye disease, Depression, Alzheimer's Disease, Parkinson's Disease, Inflammatory Bowel Disease, Rheumatoid Arthritis, Ageing, Dermatological conditions and Cancer.

Optionally, the subject is a mammal, such as a human.

The term "antibody" should be construed as covering any binding member or substance having a binding domain with the required specificity. The antibody of the invention may be a monoclonal antibody, or a fragment, functional equivalent or homologue thereof. The term includes any polypeptide comprising an immunoglobulin binding domain, whether natural or wholly or partially synthetic. Chimeric molecules comprising an immunoglobulin binding domain, or equivalent, fused to another polypeptide are therefore included.

Fragments of a whole antibody can perform the function of antigen binding. Examples of such binding fragments are; a Fab fragment comprising of the VL, VH, CL and CH1 antibody domains; an Fv fragment consisting of the VL and VH domains of a single antibody; a F(ab')2 fragments, a bivalent fragment comprising two linked Fab fragments; a single chain Fv molecule (scFv), wherein a VH domain and a VL domain are linked by a peptide linker which allows the two domains to associate to form an antigen binding site; or a bi- or tri-specific antibody, which may be multivalent or multispecific fragments constructed by gene fusion.

A fragment of an antibody or of a polypeptide for use in the present invention, generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids.

The term "antibody" includes antibodies which have been "humanized". Methods for making humanised antibodies are known in the art.

Aptamers are peptide molecules that bind to specific target molecules. Aptamers are in the realm between a small molecule and a biologic. They exhibit significant advantages relative to antibody therapeutics in terms of size, synthetic accessibility and modification.

Modulators as described herein may be used in assays, such as ELISAs, to detect NLRP3 from human blood or tissue samples. Thus, in a further aspect, the present invention provides a kit comprising one or more modulators of the first aspect of the invention. Optionally, the kit further comprises instructions for use of said kit. Optionally, the kit is for detecting NLRP3 in human cells, in blood or tissue samples.

Figure 1:
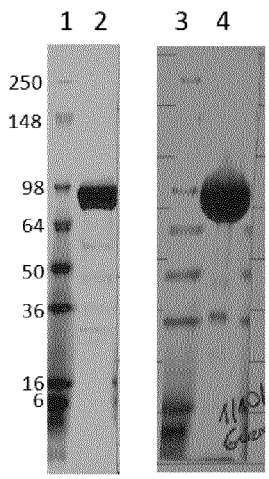

In the drawings:

FIG. 1: 4-20% denaturing, reducing and non-reducing, SDS-PAGE analysis of IL-1 R1 FC. Molecular weight marker shown in kiloDaltons.

Figure 2:
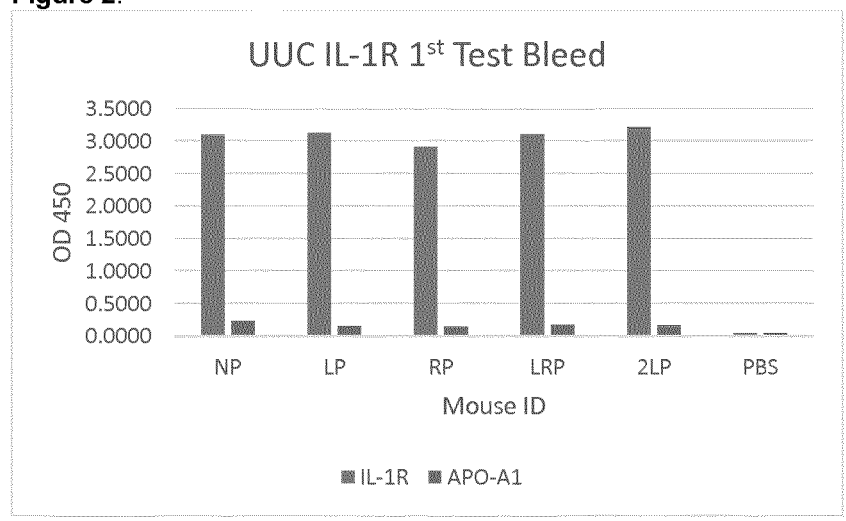

FIG. 2: UUC IL-1 R $1^{st}$ Bleed.

Figure 3:
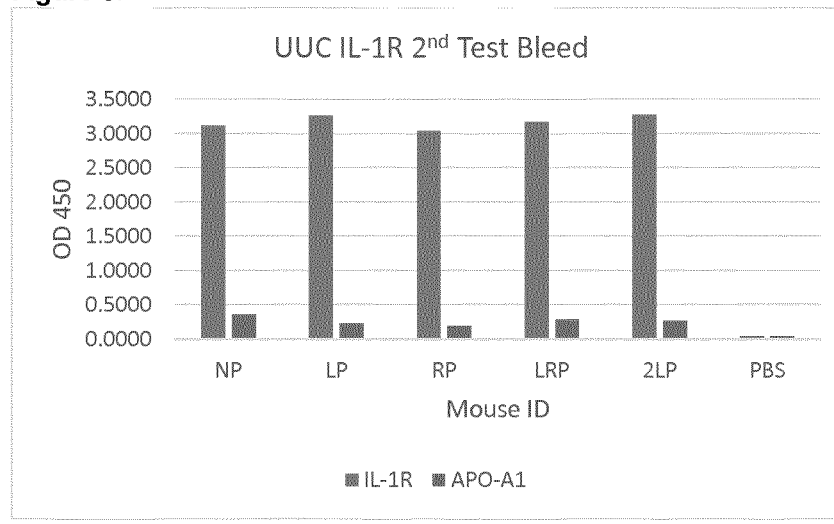

FIG. 3: UUC IL-1 R $2^{nd}$ Bleed.

Figure 4:
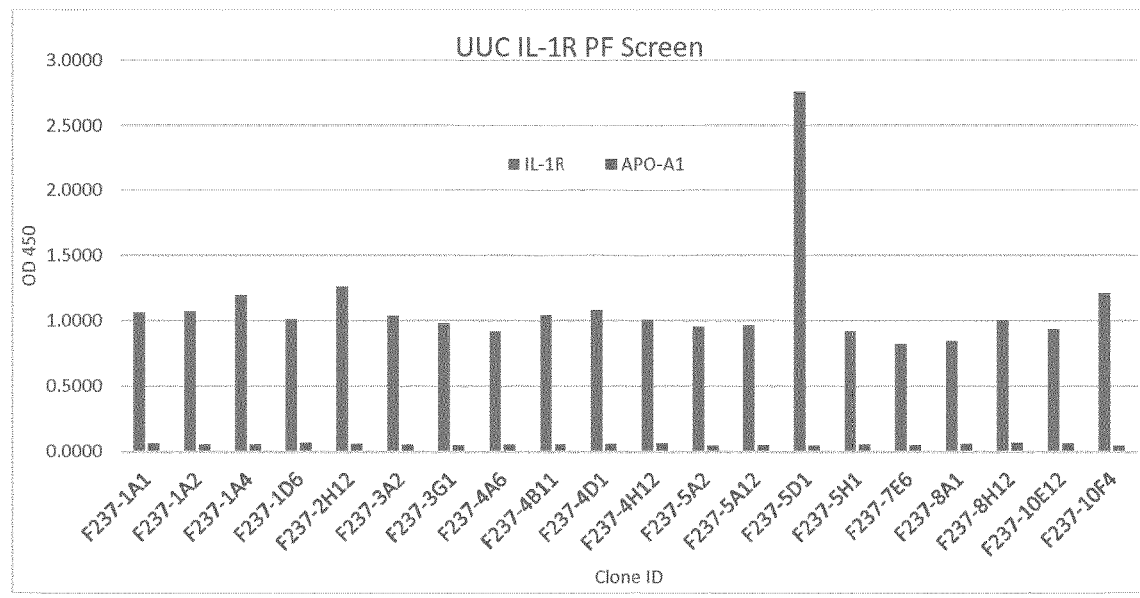

FIG. 4: Post Fusion Screening Results.

Figure 5:
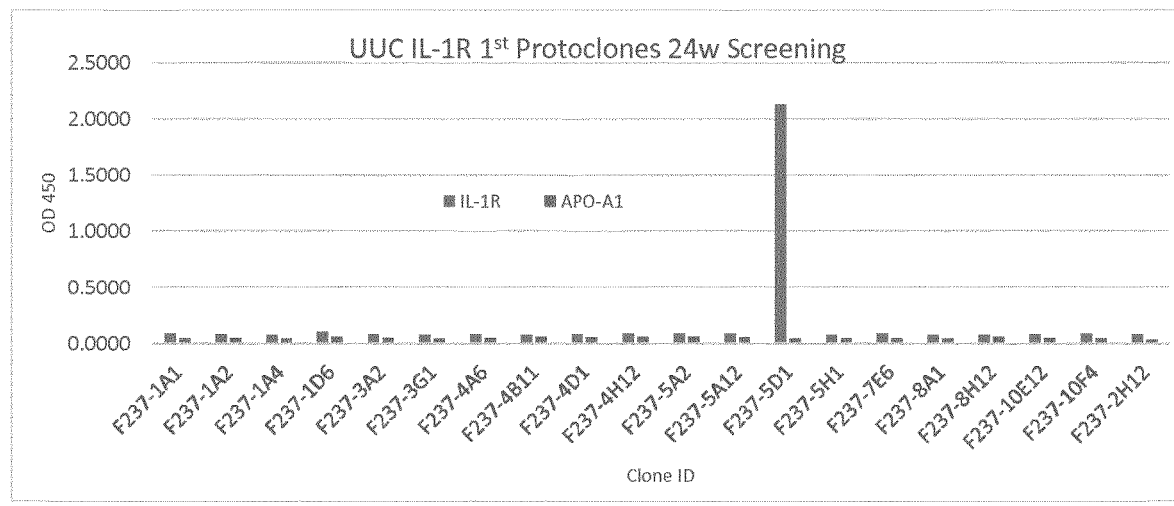

FIG. 5: $1^{st}$ Protoclones 24 well.

Figure 6:
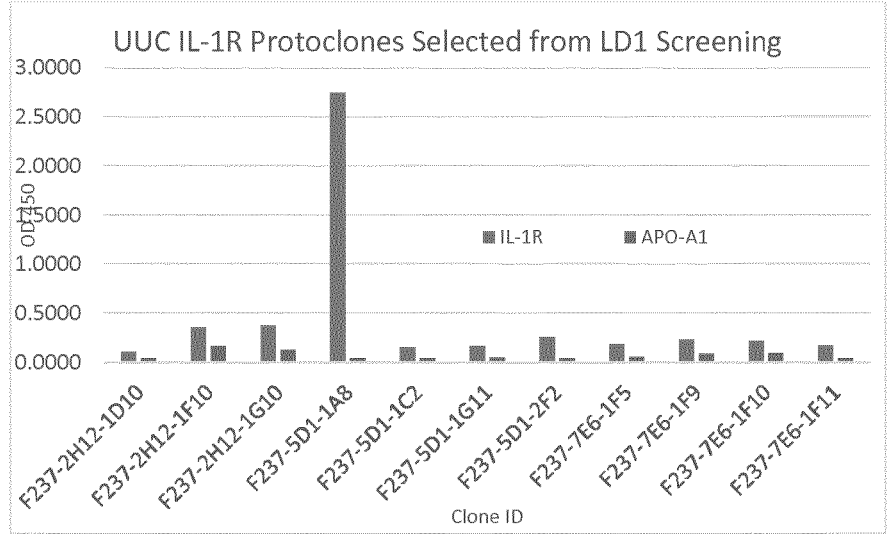

FIG. 6: LD1 Screening Results.

Figure 7:
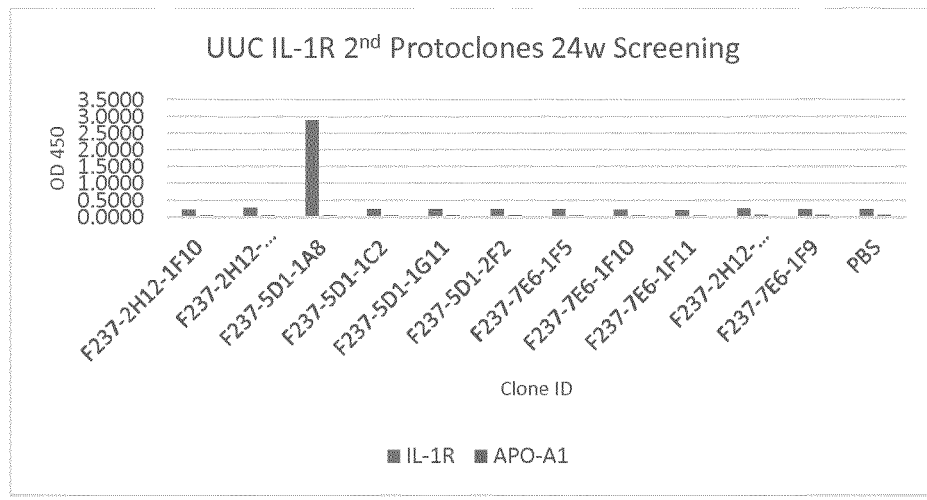

FIG. 7: 24 Well-Plate Screening Results.

Figure 8:
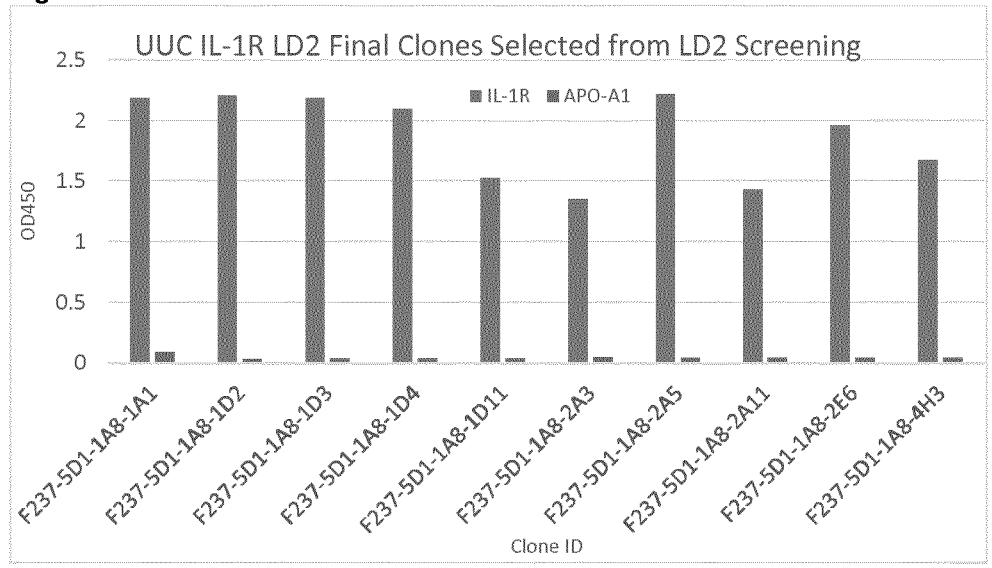

FIG. 8: Final Selected Hybridomas from F237 5D1-1A8.

Figure 9:
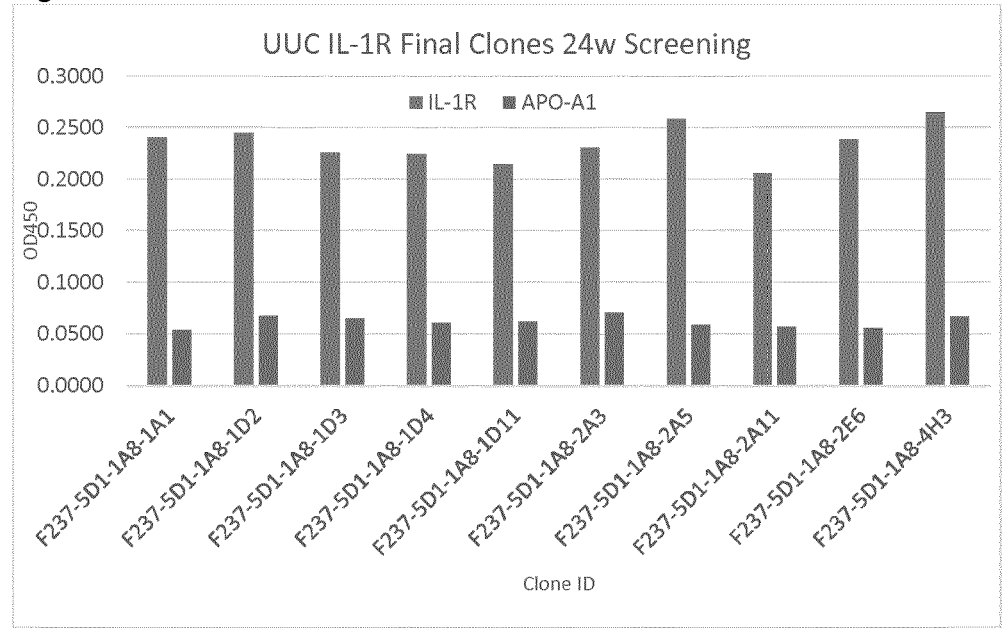

FIG. 9: Final Selected Hybridomas from F237 5D1-1A8 final 24w Screening.

Figure 10:
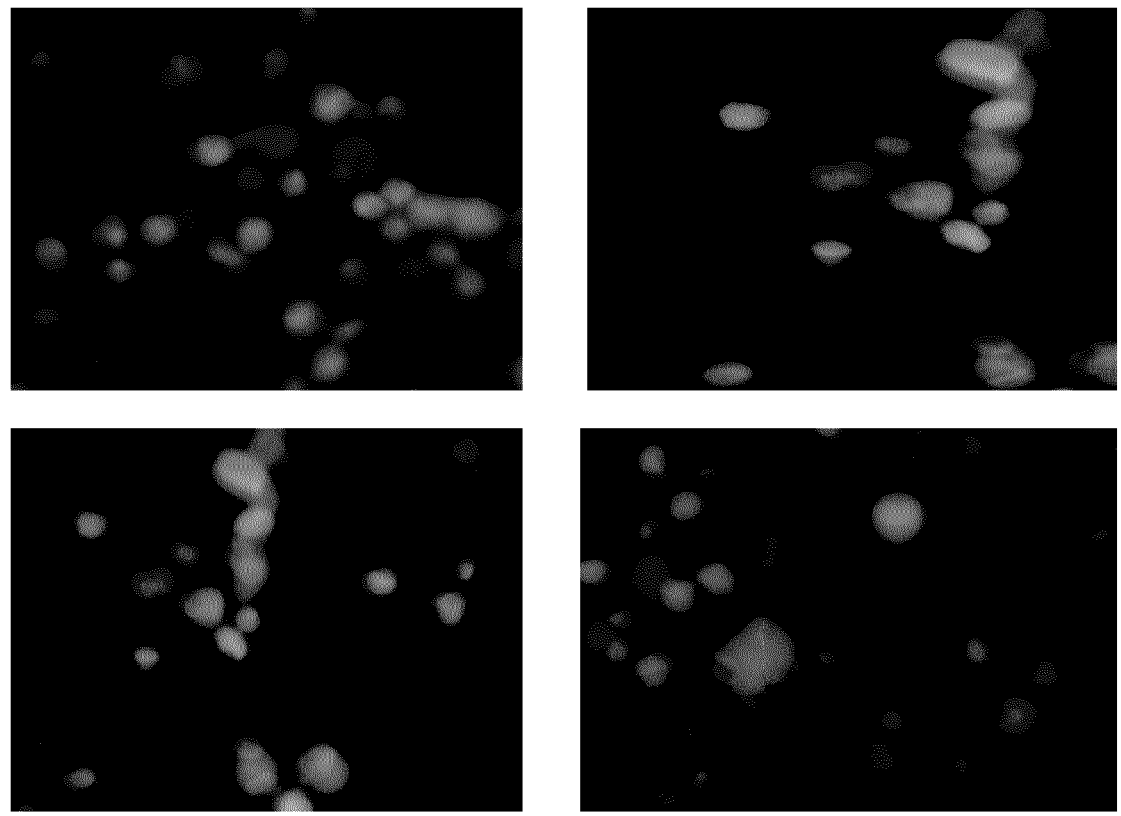

FIG. 10: IL-1 R1 Internalisation in THP1 cells—immunofluorescence imaging. Fluorescence microscopic images taken from THP1 macrophages treated with LPS and ATP to induce the expression of the IL-1 R1.

FIG. 11: IL-1 R1 Internalisation in THP1 cells—flow cytometry.

Figure 12:
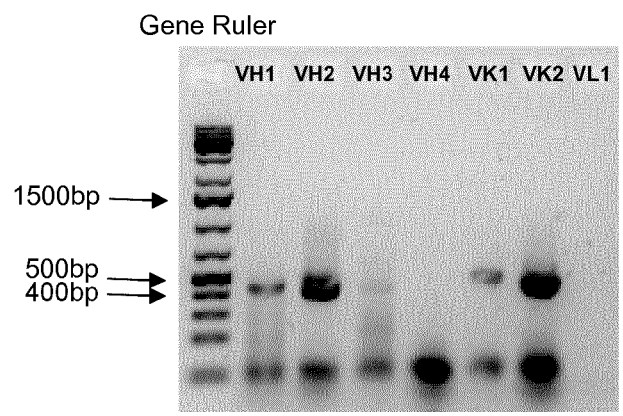

FIG. 12: PCR using several combinations of Ig variable domain primers.

Figure 13:
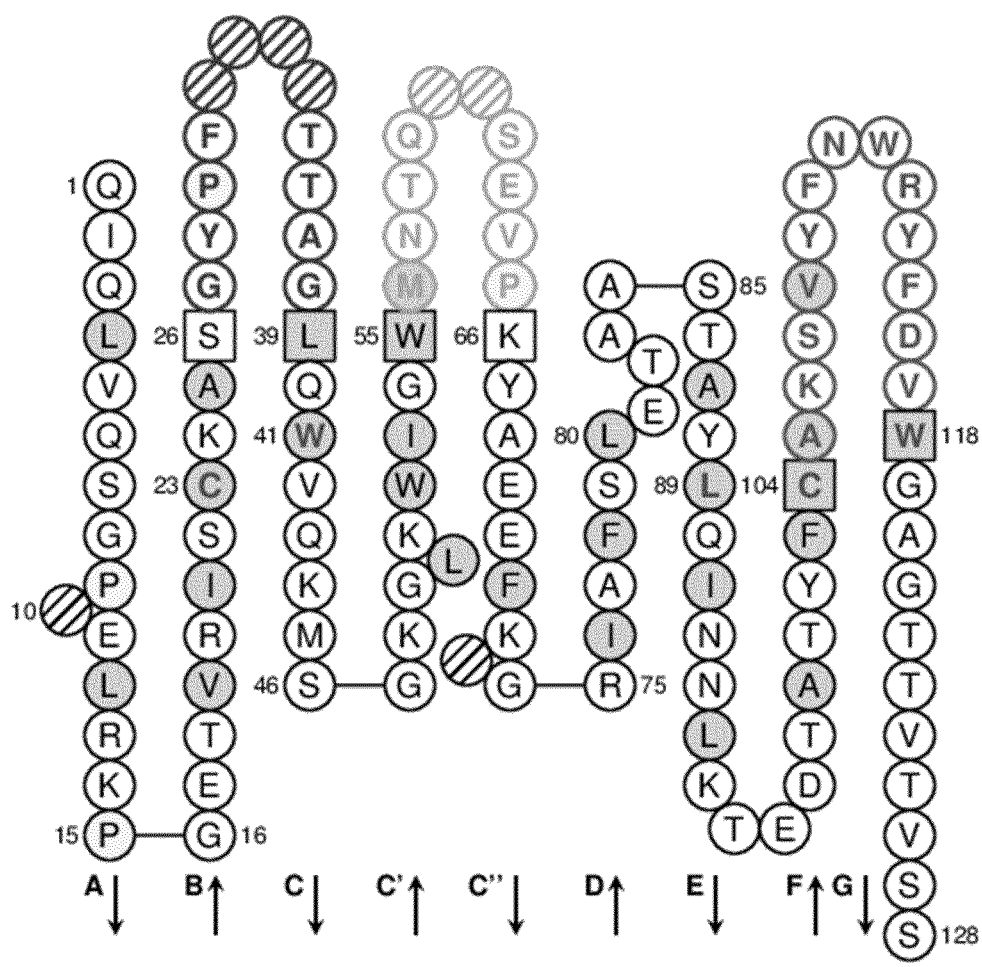

FIG. 13: Graphical representation of the CDR loops. Ref: Lefranc, M.-P. et al., Dev. Comp. Immunol., 27, 55-77 (2003) PMID: 12477501).

Figure 14:
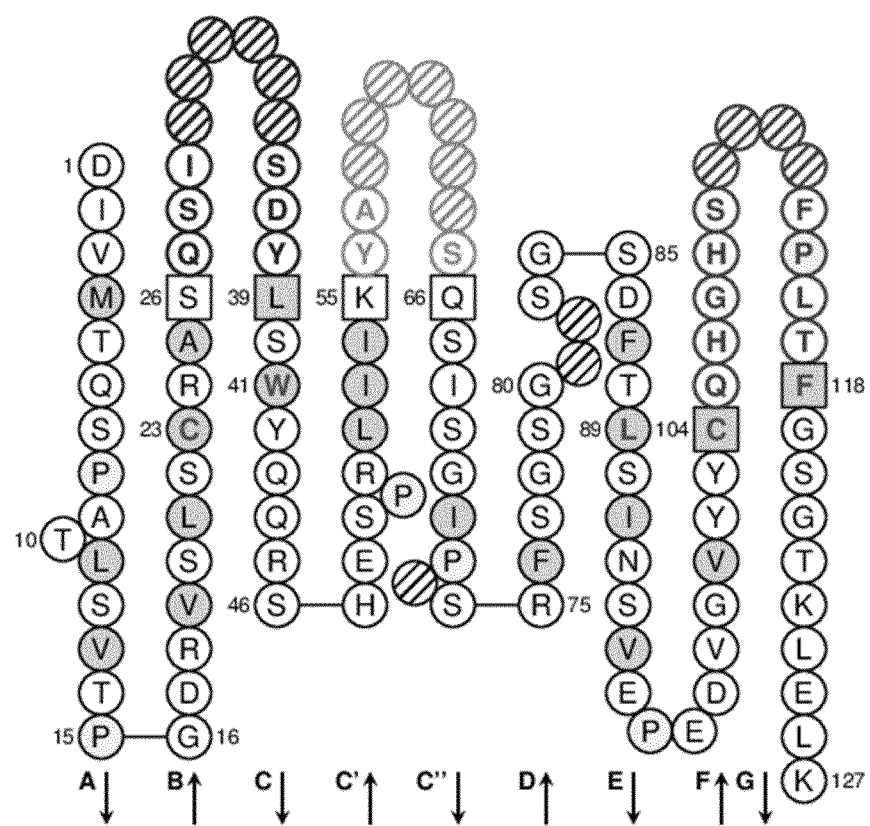

FIG. 14: Graphical representation of the CDR loops (Lefranc, M.-P. et al., Dev. Comp. Immunol., 27, 55-77 (2003) PMID: 12477501).

FIG. 15: Structure of NLRP3 inflammasome. Bergsbaken, T.; Fink, S. L.; Cookson, B. T. (2009). "Pyroptosis: Host cell death and inflammation". Nature Reviews Microbiology. 7 (2): 99-109. doi:10.1038/nrmicro2070. PMC 2910423. PMID 19148178. and Dagenais, M.; Skeldon, A.; Saleh, M. (2011). "The inflammasome: In memory of Dr. Jurg Tschopp". Cell Death and Differentiation. 19 (1): 5-12. doi:10.1038/cdd.2011.159. PMC 3252823. PMID 22075986. http://jonlieffmd.com/blog/cellular-intelligence-blog/inflammasomes-are-large-complex-signaling-platforms FIG. 16: Sequence alignment using CLUSTAL 0 (1.2.4) of the consensus sequences of C-term domains of human and mouse NALP (NLRP) proteins.

Figure 17:
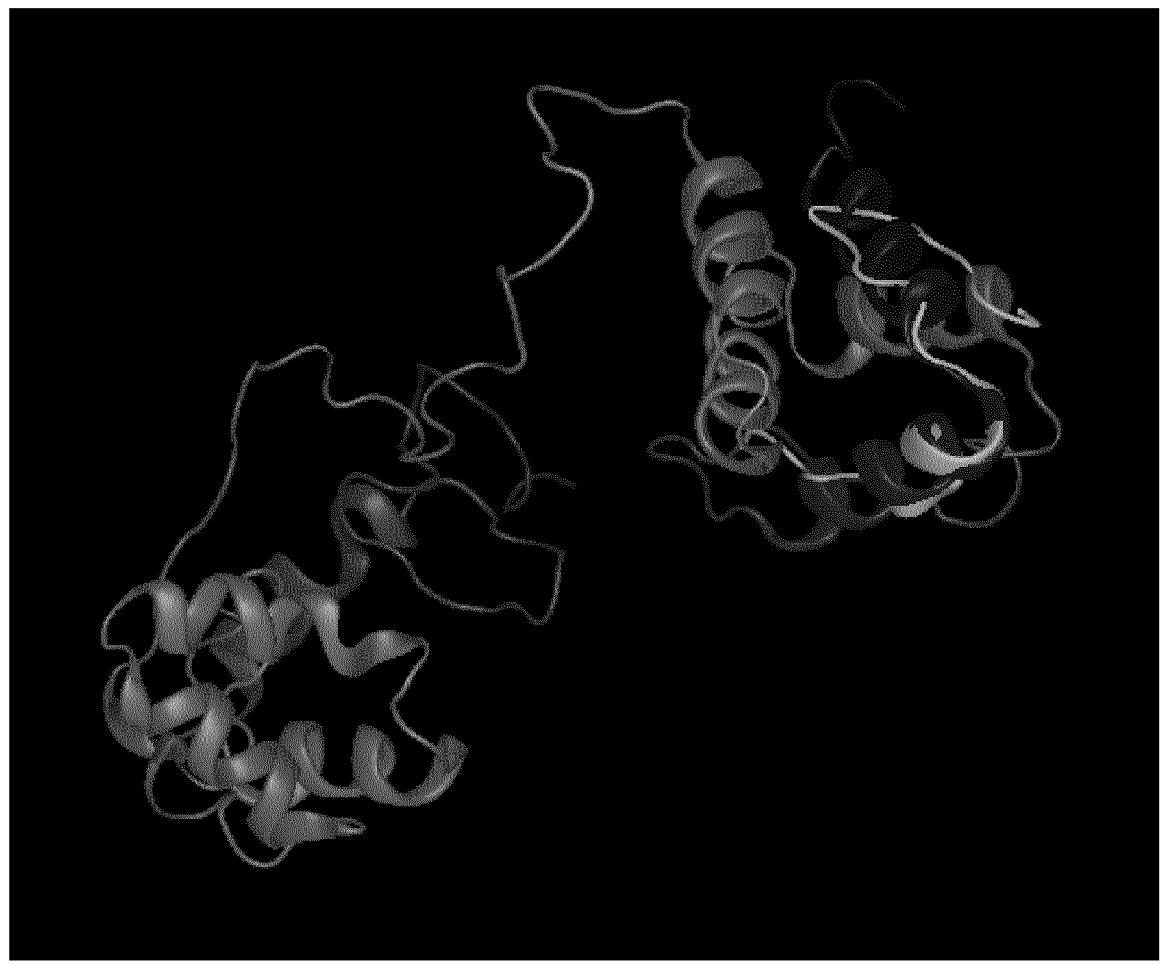

FIG. 17: Novafold predicted structure of Peptide FUS_746_001 (Yellow) aligned to NLRP3 PDB: 3QF2 showing secondary structural features using Protean 3D, version 14.0.1

Figure 18:
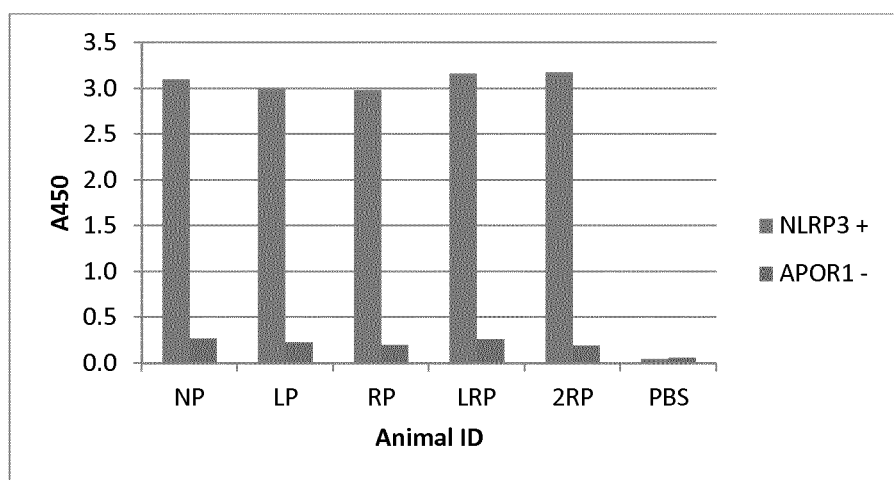

FIG. 18: Immunized mice expressed high levels of the NLRP3 mAb.

Figure 19:
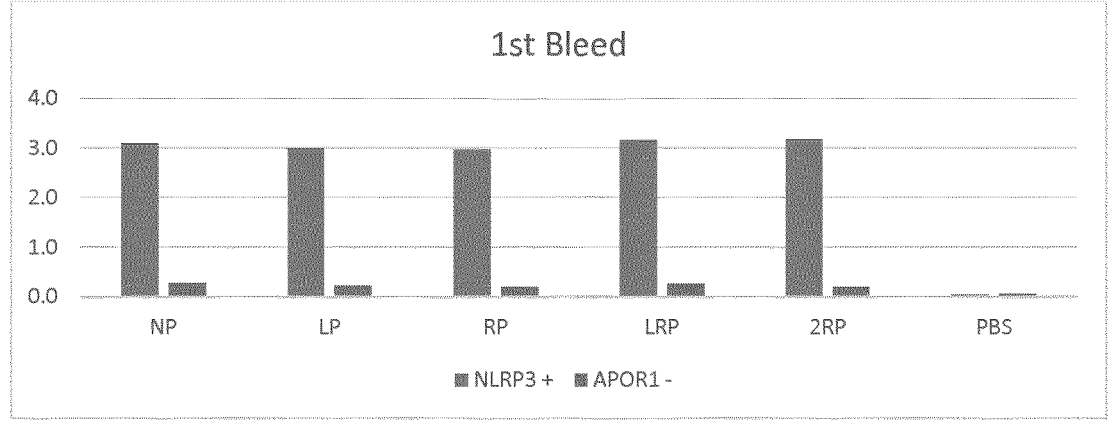

FIG. 19: UUC NLRP3 $1^{st}$ Bleed.

Figure 20:
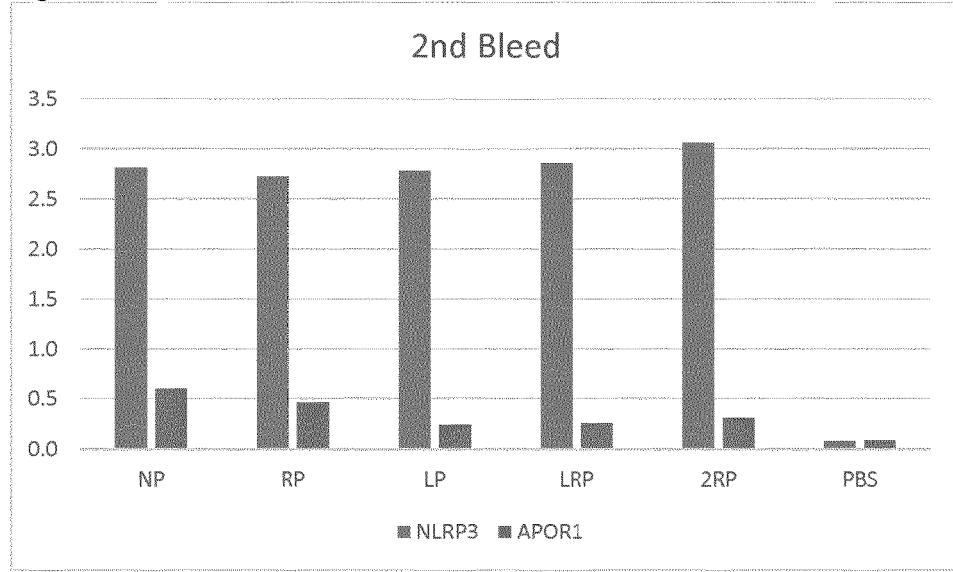

FIG. 20: UUC NLRP3 $2^{nd}$ Bleed.

Figure 21:
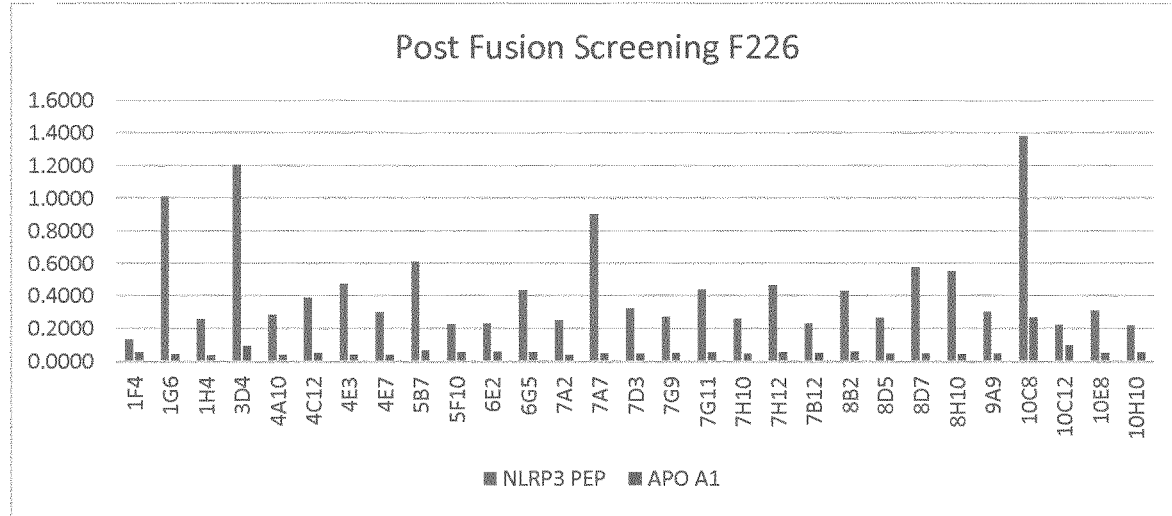

FIG. 21: Post Fusion Screening Results.

Figure 22:
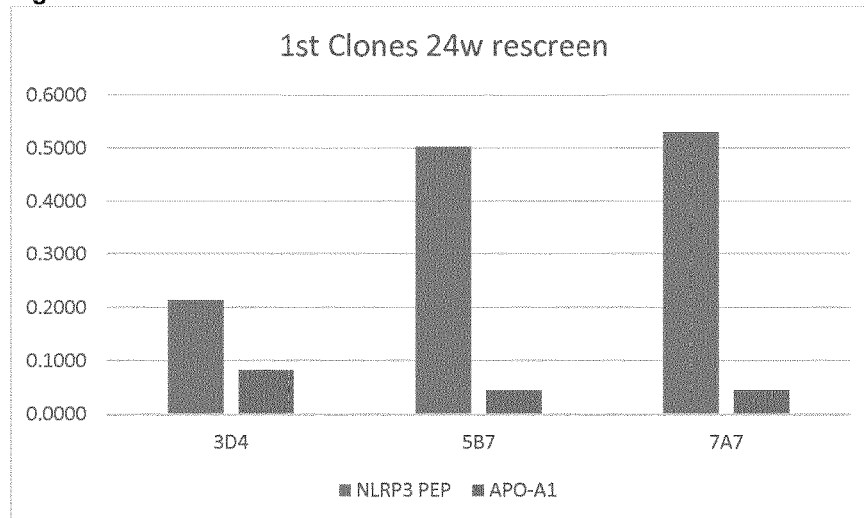

FIG. 22: $1^{st}$ Protoclones 24 well.

Figure 23:
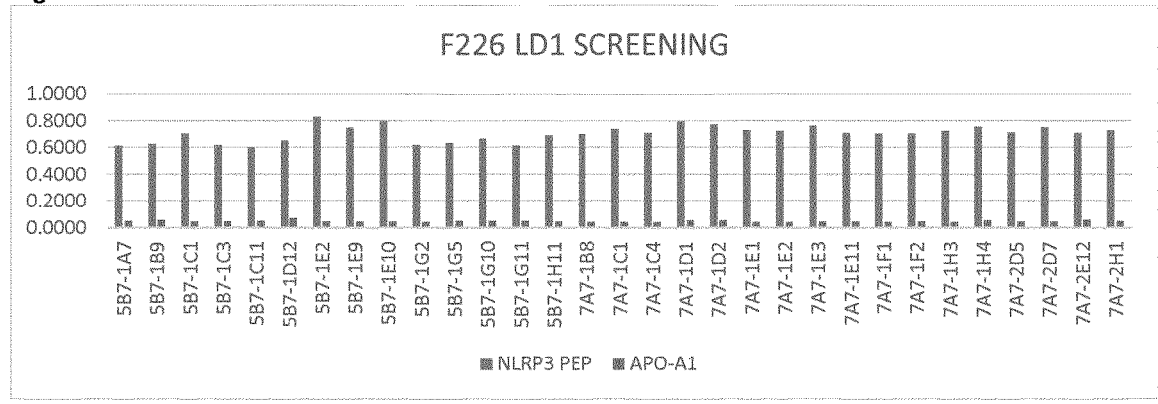

FIG. 23: LD1 Screening Results.

Figure 24:
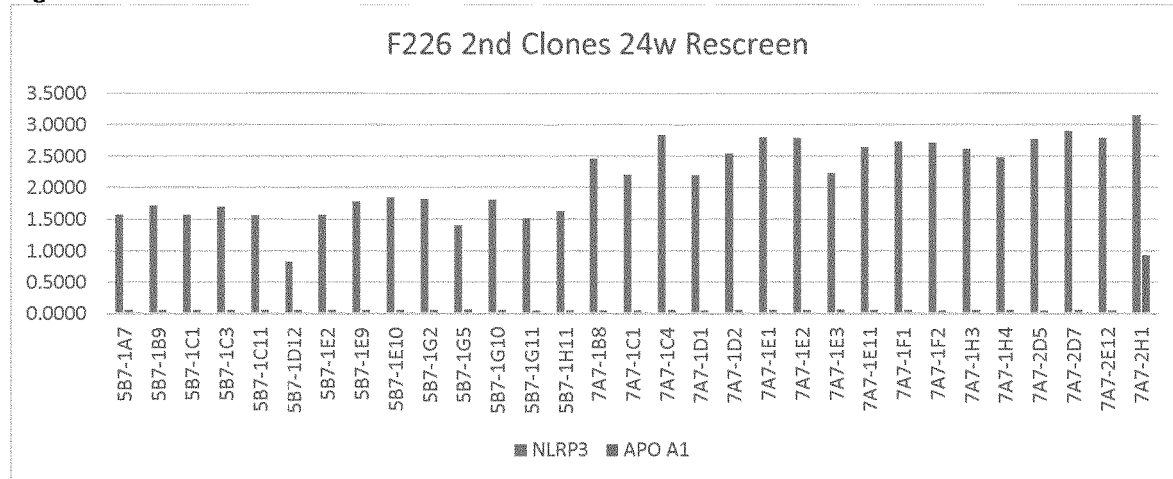

FIG. 24: 24 Well-Plate Screening Results.

Figure 25:
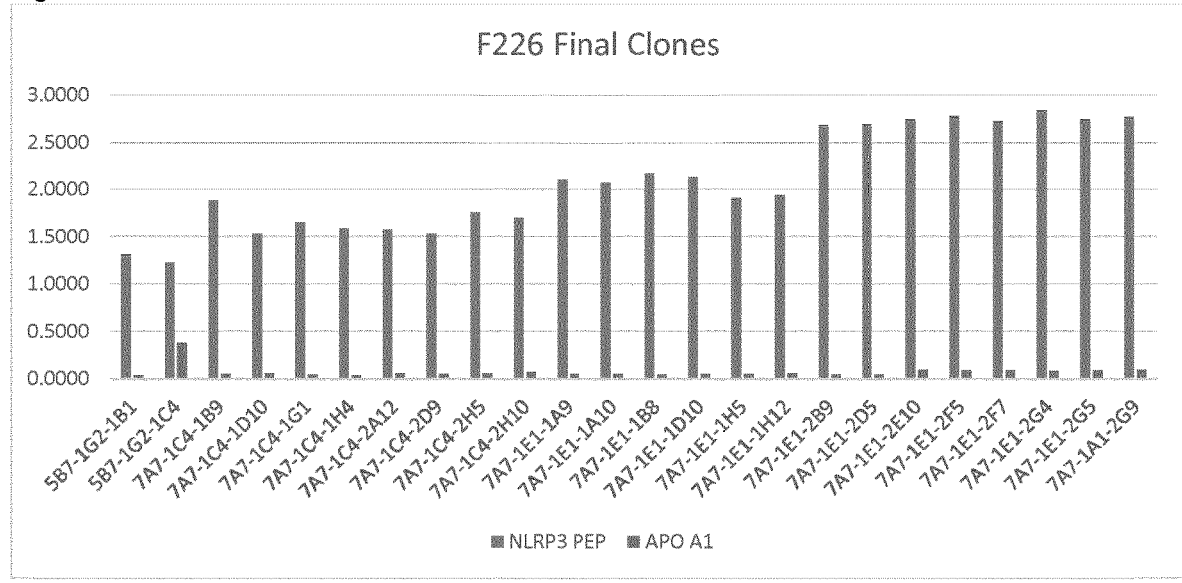

FIG. 25: Final Selected Hybridomas from F226.

Figure 26:
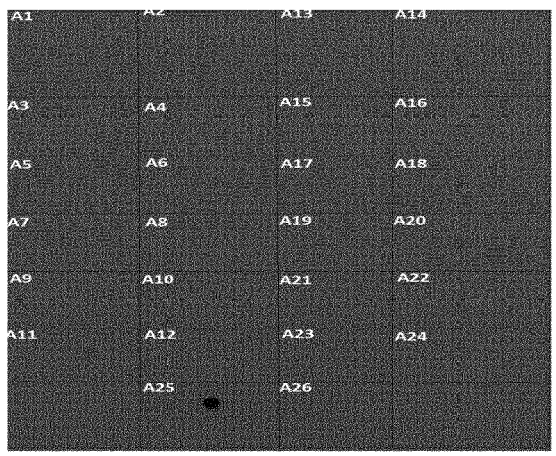

FIG. 26: Dot Blot analysis.

Figure 27:
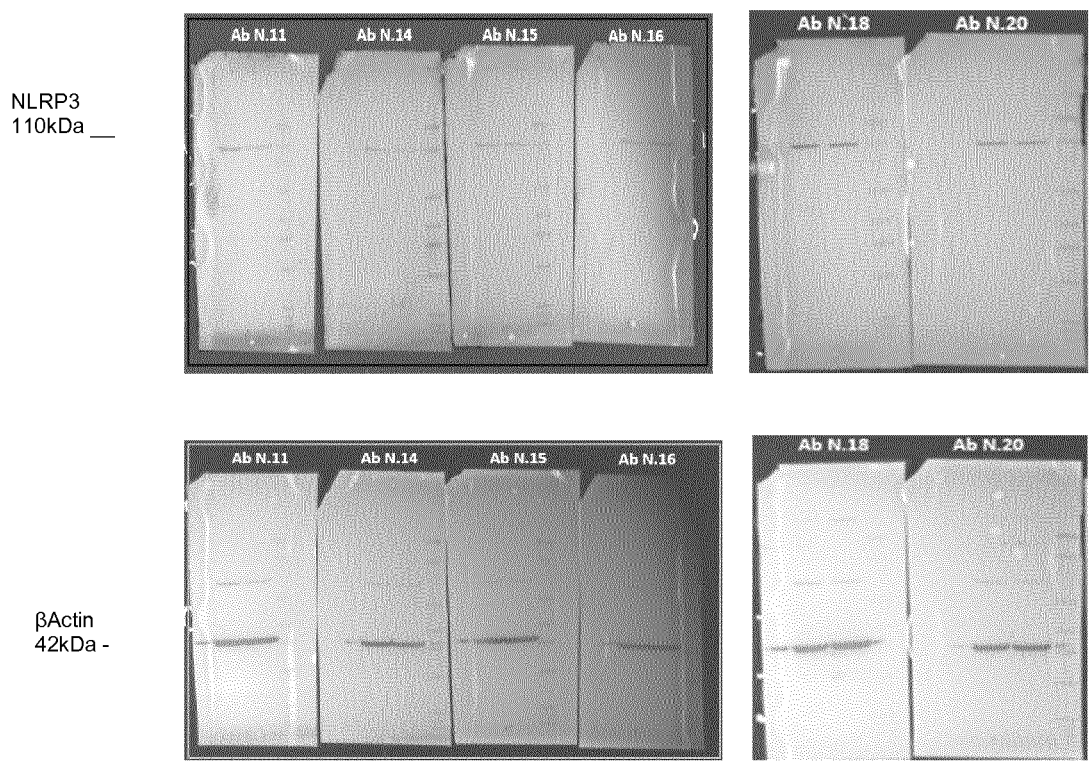

FIG. 27: Western Blot Analysis.

Figure 28:
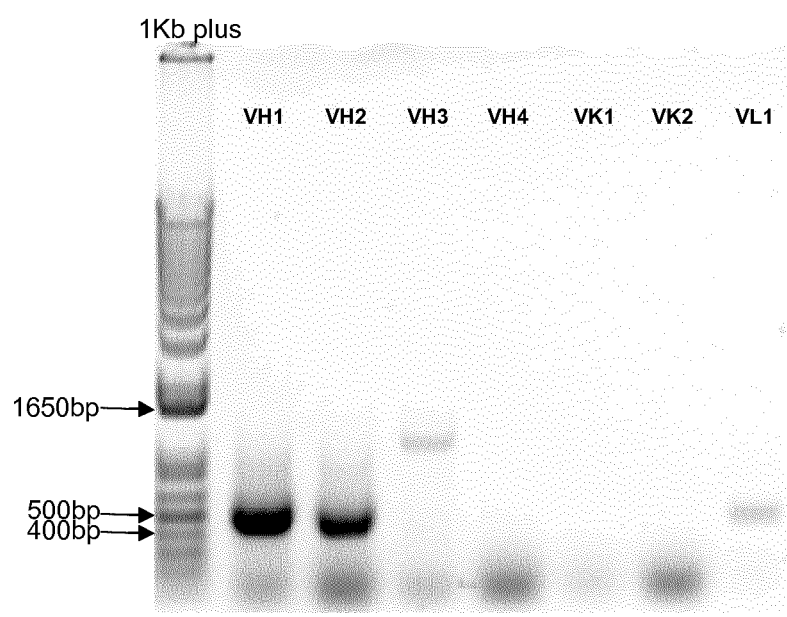

FIG. 28: PCR using several combinations of Ig variable domain primers.

Figure 29:
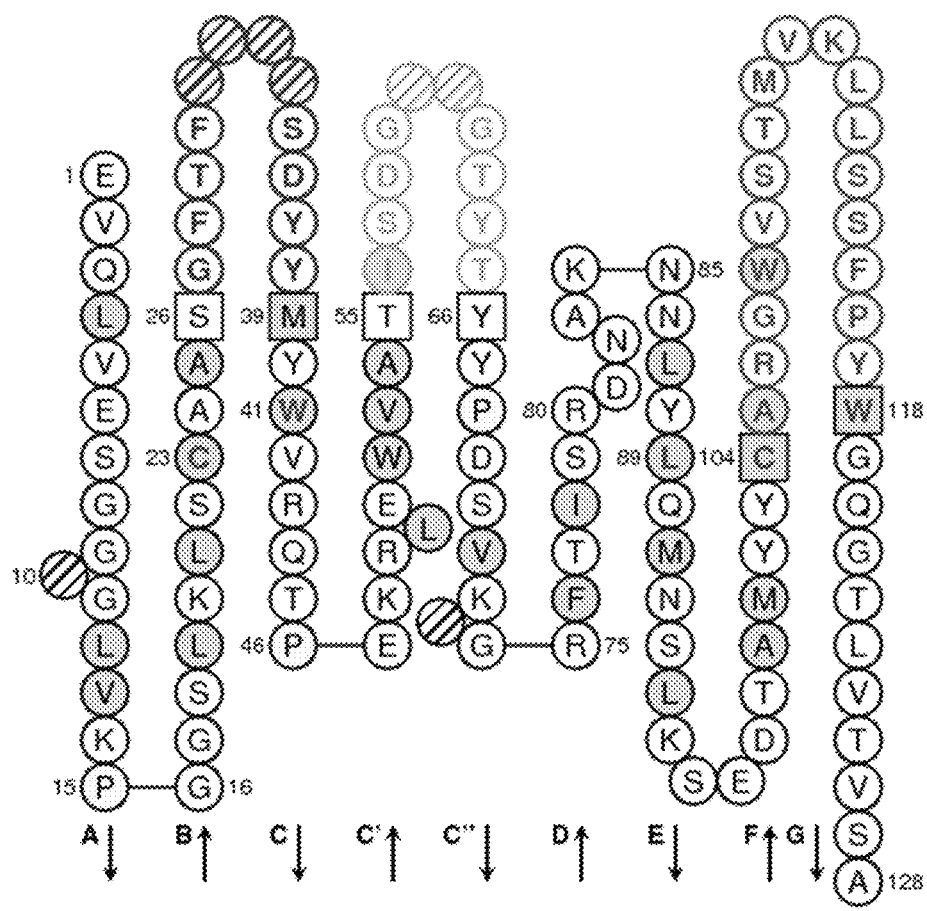

FIG. 29: Graphical representation of the CDR loops (Lefranc, M.-P. et al., Dev. Comp. Immunol., 27, 55-77 (2003) PMID: 12477501).

Figure 30:
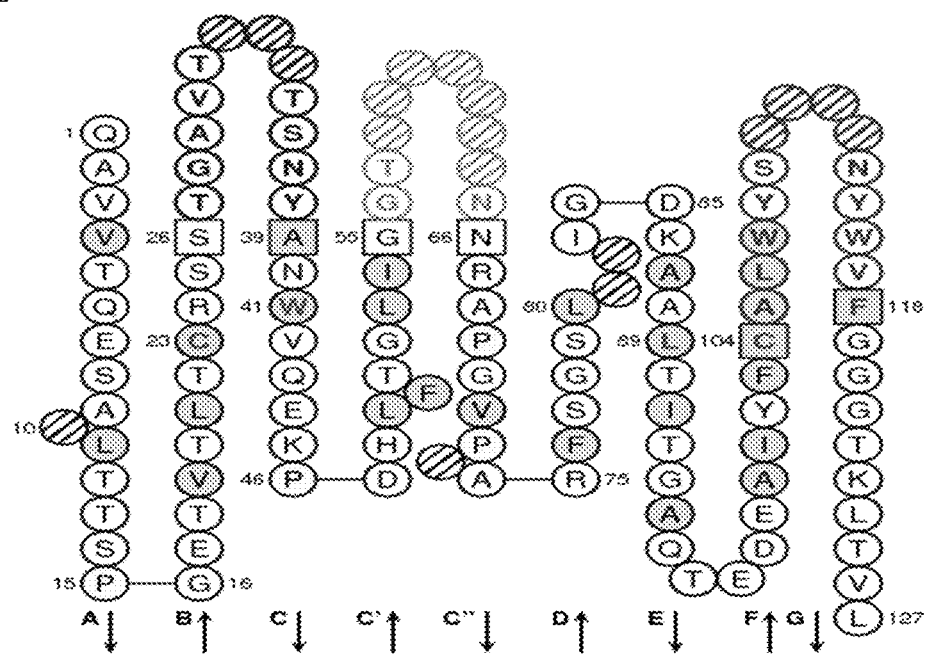

FIG. 30: Graphical representation of the CDR loops (Lefranc, M.-P. et al., Dev. Comp. Immunol., 27, 55-77 (2003) PMID: 12477501).

Figure 31:
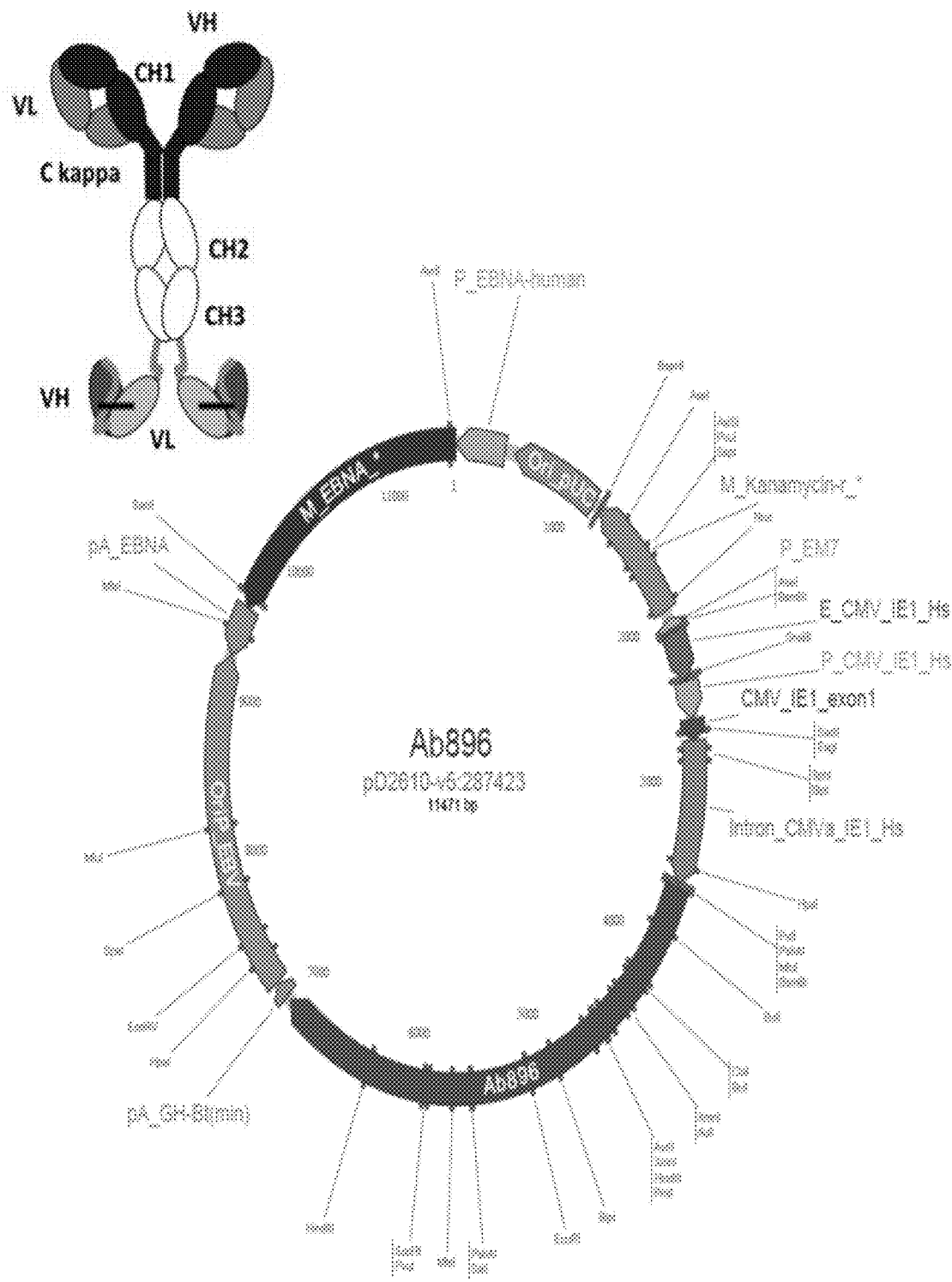

FIG. 31: Diagram illustrating the bispecific design and the plasmid map of InflaMab.

Figure 32:
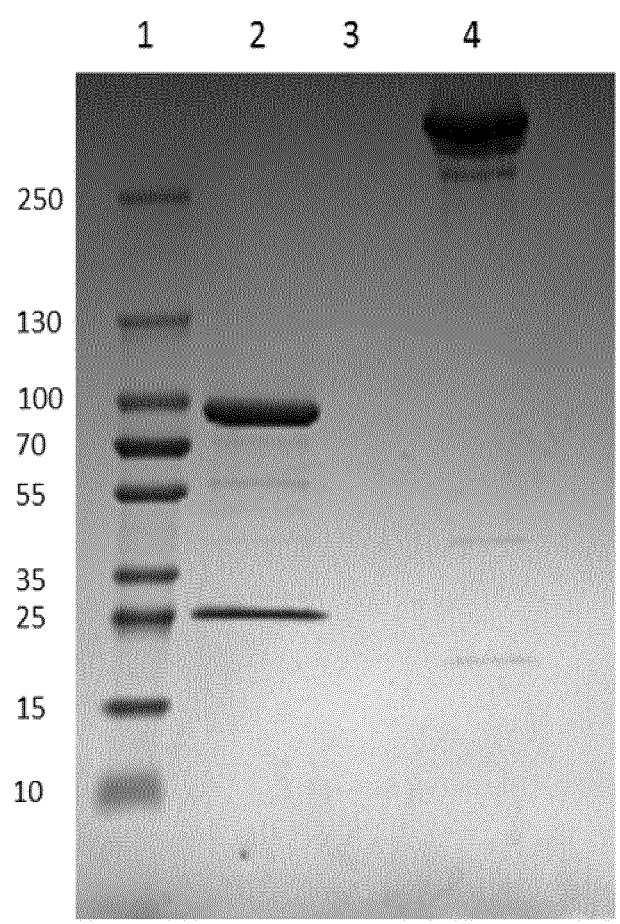

FIG. 32: 4-20% SDS-PAGE analysis of InflaMab. Molecular weight marker shown in kiloDaltons.

FIG. 33: Inflamab prevents IL-1 release. (Note, "Ulster Ab" is synonymous with "Inflamab" and "Bi-specific Ab".)

Figure 34:
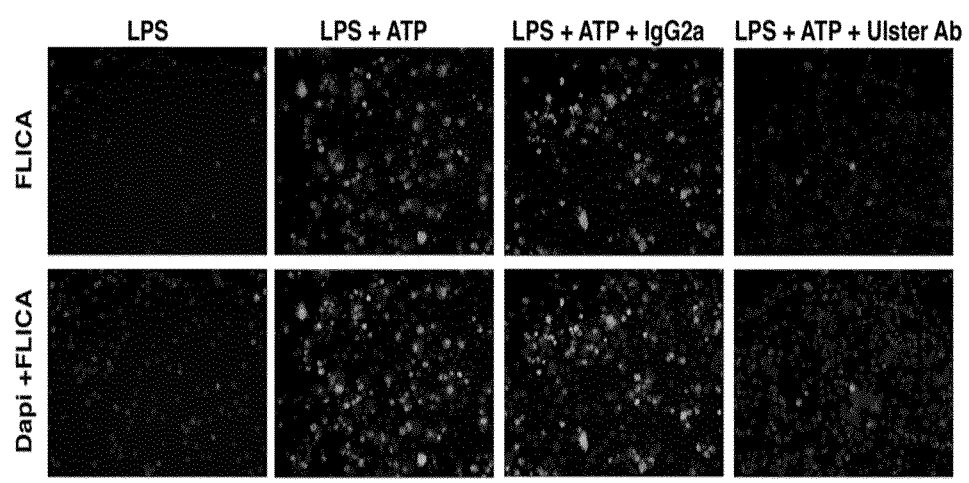

FIG. 34: Inflamab prevents caspase-1 activation in THP1 cells.

FIG. 35: Internalization of Inflamab.

Figure 36A:
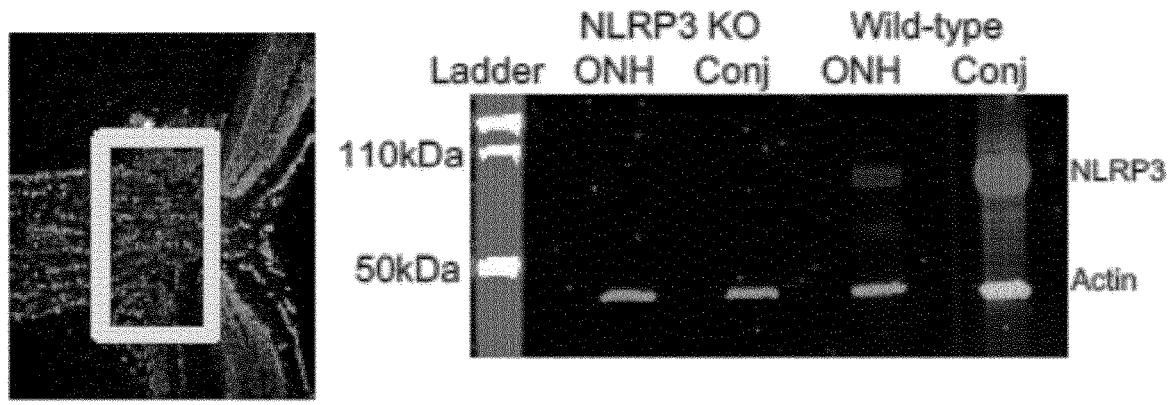
Figure 36B:
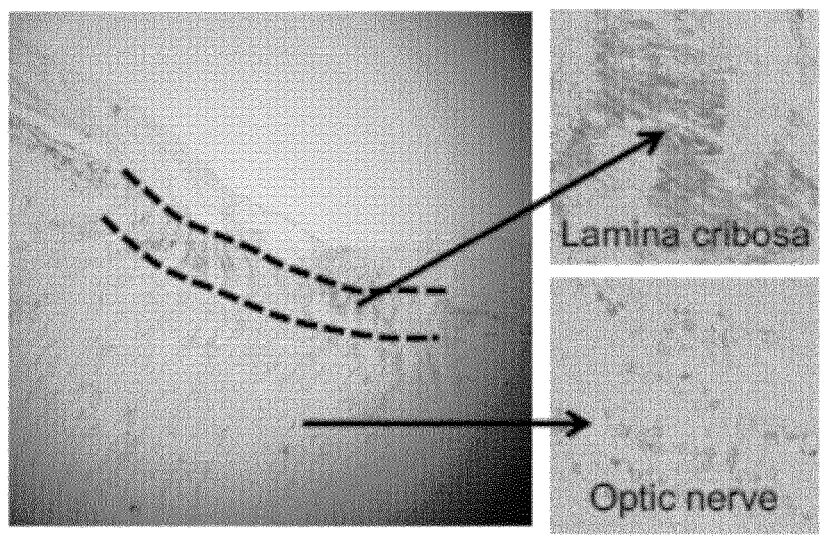

FIG. 36: Constitutive expression of NLRP3 in the mouse and human ONH.

Figure 37:
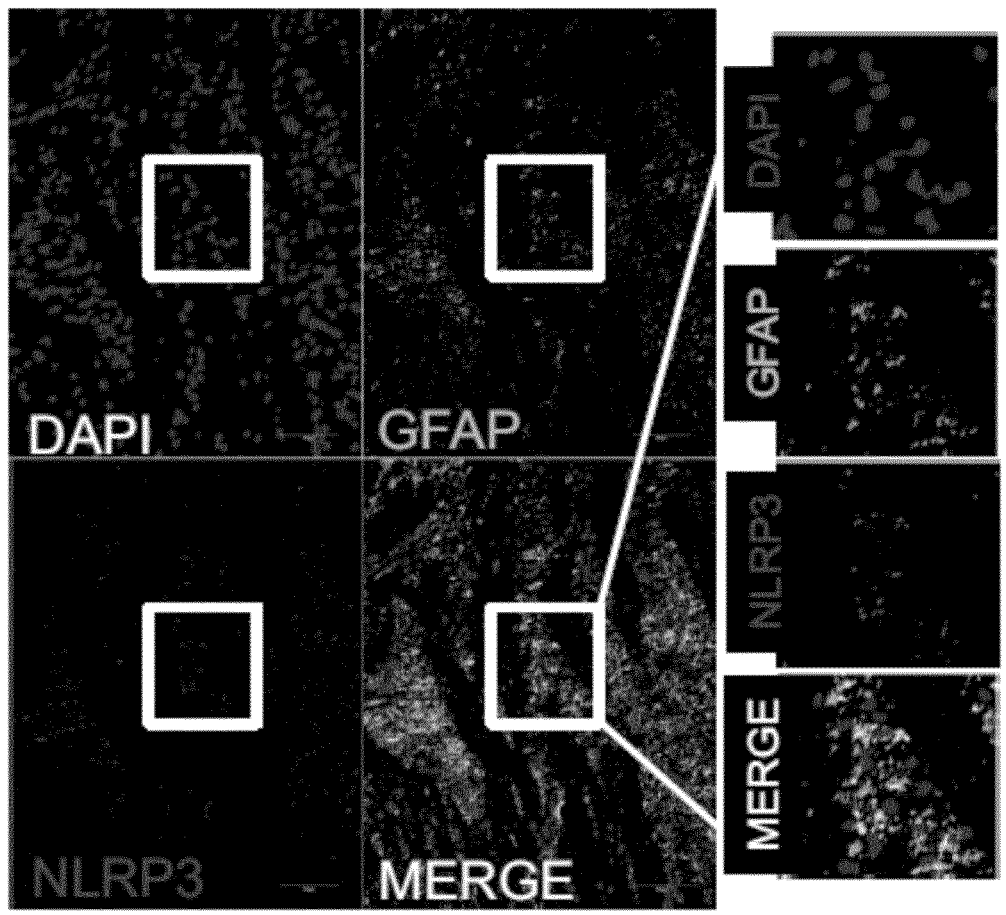

FIG. 37: Constitutive NLRP3 expression in the astrocytes of the human ONH.

Figure 38:
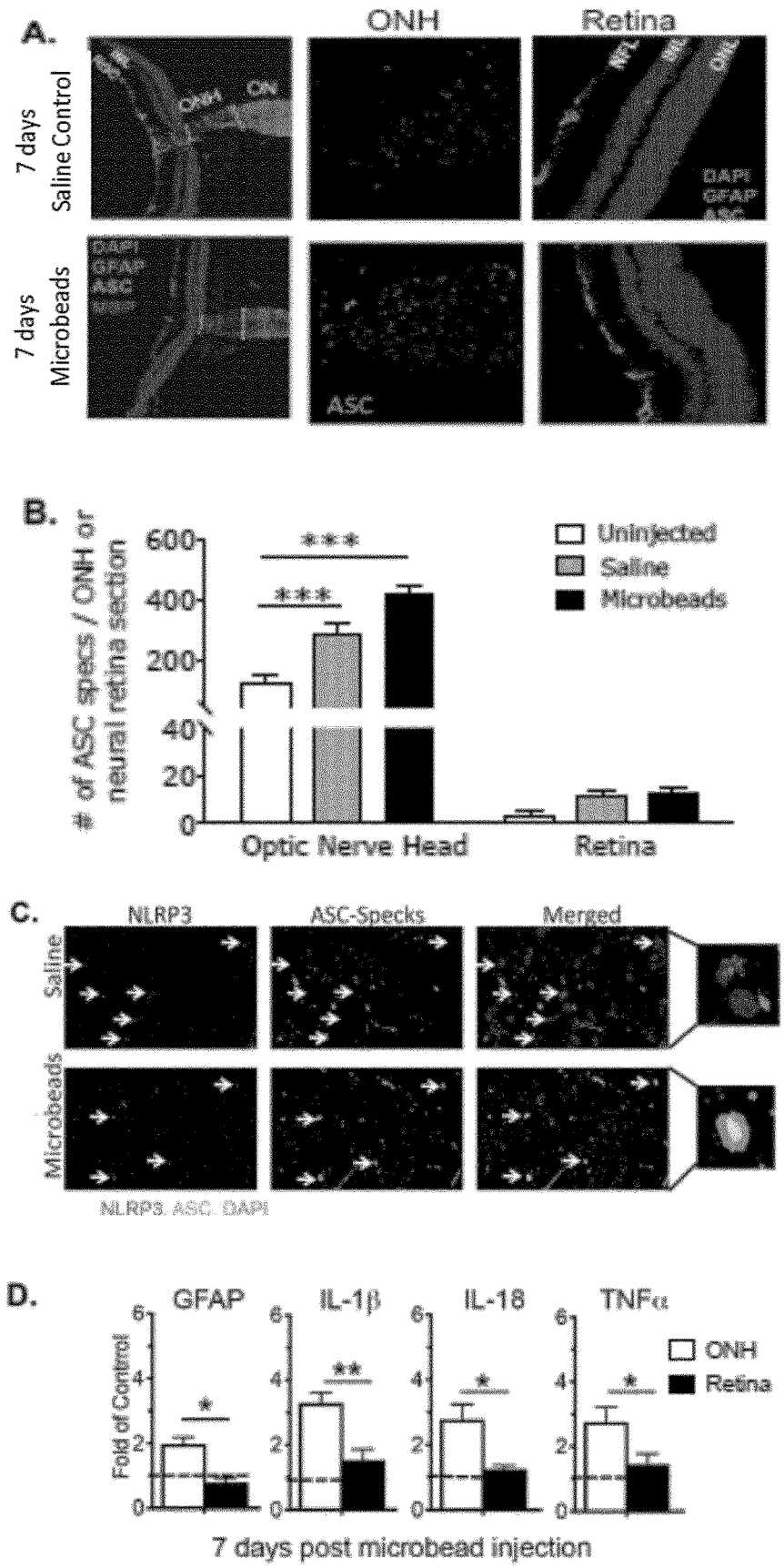

FIG. 38: Assembly of the NLRP3 inflammasome in the ONH coincides with the induction of inflammatory mediators at 7 days post microbead injection.

Figure 39:
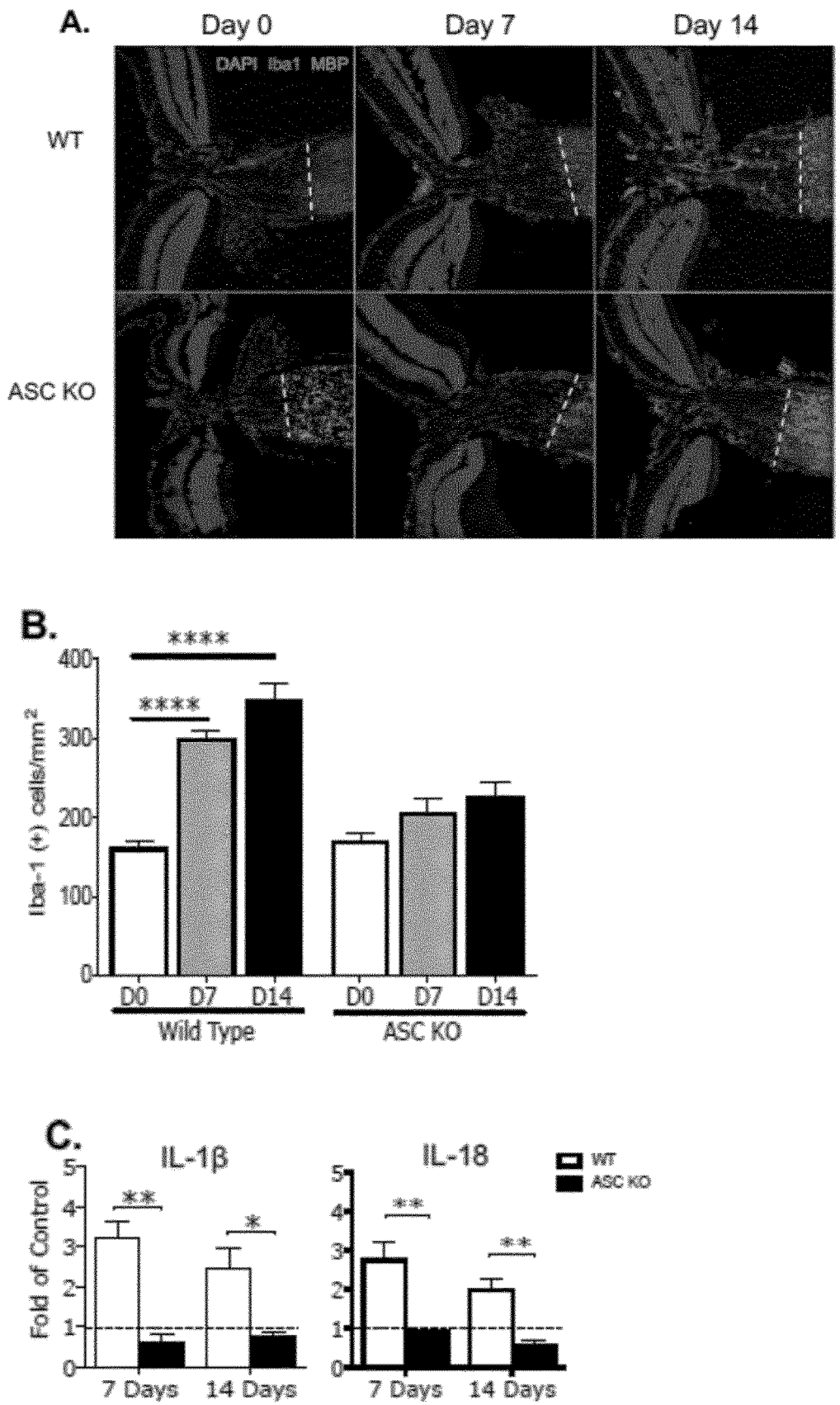

FIG. 39: Early induction of inflammatory mediators and accumulation of Iba1+ cells in the ONH is abrogated in inflammasome deficient (ASC KO) mice.

FIG. 40: ASC and NLRP3 are required for IOP-induced axon degeneration and death of RGCs in microbead-induced mouse model of glaucoma.

FIG. 41: NLRP3 small molecule inhibitor, MCC950, prevents death of RGCs in microbead model of glaucoma.

Figure 42:
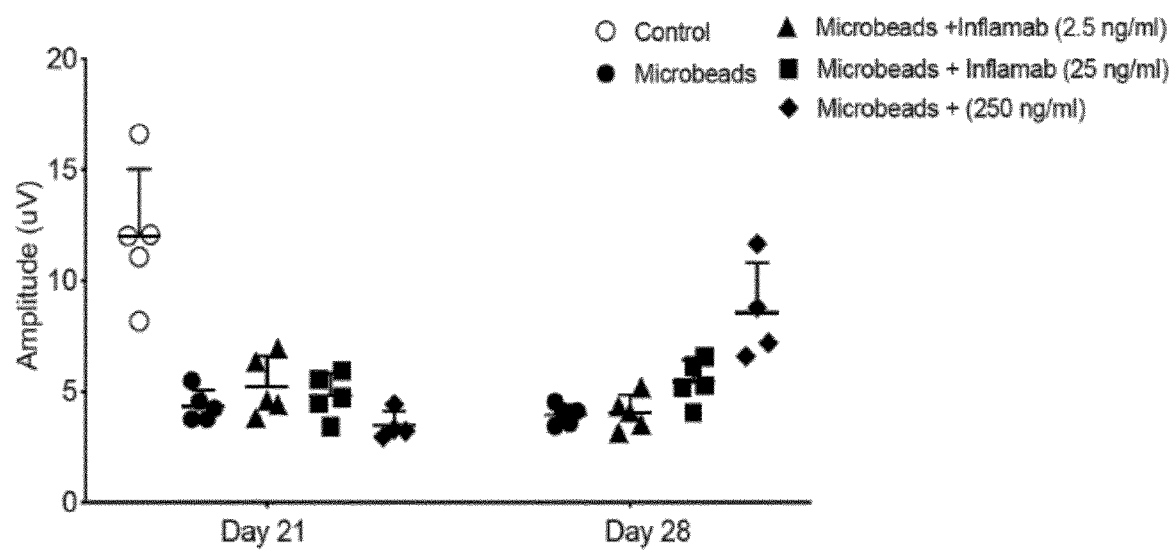

FIG. 42: InflaMab prevents death of RGCs in microbead model of glaucoma.

In a particular use or method of treatment, the modulator of the invention, e.g. the bi-specific antibody, acts according to steps which include:
1. Targeting the bispecific antibody to IL-1 R1 to allow internalisation and entry of the antibody into the cell.
2. Targeting the antibody to NLRP3 in order to inhibit NLRP3 inflammasome assembly and subsequent IL-1 release from the cell, thus reducing inflammation.
3. Targeting the antibody to IL-1 R1 triggers internalisation of the IL-1 R1, thus making less IL-1R1 available for IL-1β binding resulting in further inhibiting the potentiation and amplification of inflammation.

Such a modulator of the first aspect of the invention provides a surprisingly additive inhibitory effect upon the inflammasome as a whole, not only the NLRP3 protein portion and thus will provide a more effective inhibitor of inflammasome-related diseases.

EXAMPLES

Transient Expression of IL-1R1 FC fusion (Example 1)
Generation of a monoclonal antibody against IL-1 R1 (Example 2)
IL-1 R1 monoclonal antibody sequencing report (Example 3)
NLRP3 peptide synthesis (Example 4)
Generation of a monoclonal antibody against NLRP3 (Example 5)
NLRP3 monoclonal sequencing report (Example 6)
InflaMab design (Example 7)
InflaMab transient expression (Example 8)
InflaMab for Atherosclerosis/Coronary Artery Disease (Example 9)

Example 1: Transient Expression of IL-1R1 Fc Fusion

IL-1 R1 Fc is transiently expressed and purified in HEK293 cells. The purified protein is evaluated for size and purity by SDS PAGE and tested for endotoxin levels. Finally the protein is evaluated for activity by ELISA.

A mammalian expression vector encoding interleukin-1 receptor (IL-1 R1) Fc fusion protein was transfected into HEK293 cells. The expressed Fc fusion protein was subsequently purified from cell culture supernatant using standard chromatography techniques. The concentration and purity were determined for the purified product.

Transient Transfection of HEK293 Cells and Purification of Protein

DNA coding for the amino acid sequence of IL-1 R1 Fc (see Example 1A) was synthesised and cloned into a mammalian transient expression plasmid pD2610-v1 (DNA2.0). IL-1R1 Fc was expressed using a HEK293 cell based transient expression system and the resulting antibody containing cell culture supernatants was clarified by centrifugation and filtration. Two lots of IL-1 R1 Fc were purified (using AKTA chromatography equipment) from cell culture supernatants via protein A affinity chromatography. Purified protein was dialysed/buffer exchanged into phosphate buffered saline solution. The purity of the recombinant protein was determined to be >95%, as judged by Sodium Dodecyl Sulphate Polyacrylamide gels (FIG. 1). Protein concentration was determined by measuring absorbance (1.0 mg/ml=A280 of 1.37). Details of the purified product are summarized in Table 1.

FIG. 1 shows 4-20% denaturing, reducing and non-reducing, SDS-PAGE analysis of IL-1 R1 FC. Molecular weight marker shown in kiloDaltons. Lanes are as follows:

| Lane Number | Sample | Lot | Amount (µg) | Conditions |
|---|---|---|---|---|
| 1 | See Blue plus 2 (Thermo Fisher) | — | — | Reducing |
| 2 | IL-1R1 FC | 1 | — | Reducing |
| 3 | Blank | — | — | NA |
| 4 | IL-1R1 FC | 2 | — | Reducing |

TABLE 1

Purification summary: IL-1R1 Fc

| Sample | Lot | Concentration (mg/ml) | Volume (ml) | Total (mg) | Purity | Endotoxin (EU/mg) |
|---|---|---|---|---|---|---|
| IL-1R1Fc | 1 | 0.64 | 1.6 | 1.02 | >95% | ND |
| IL-1R1Fc | 2 | 0.95 | 1.4 | 1.33 | >95% | ND |

Abbreviations are as follows; ND, not determined.

Example 1A: IL-1 R1 Fc Amino Acid Sequence

```
                                        (SEQ ID NO: 1)
MKVLLRLICFIALLISSLEADKCKEREEKIILVSSANEIDVRPCPLNPNE

HKGTITWYKDDSKTPVSTEQASRIHQHKEKLWFVPAKVEDSGHYYCVVRN

SSYCLRIKISAKFVENEPNLCYNAQAIFKQKLPVAGDGGLVCPYMEFFKN

ENNELPKLQWYKDCKPLLLDNIHFSGVKDRLIVMNVAEKHRGNYTCHASY

TYLGKQYPITRVIEFITLEENKPTRPVIVSPANETMEVDLGSQIQLICNV

TGQLSDIAYKWNGSVIDEDDPVLGEDYYSVENPANKRRSTLITVLNISE

IESRFYKHPFTCFAKNTHGIDAAYIQLIYPVTNFQKLEGGPSVFIFPPNI

KDVLMISLTPKVTCVVVDVSEDDPDVQISWFVNNVEVHTAQTQTHREDYN

STIRVVSHLPIQHQDWMSGKEFKCKVNNKDLPSPIERTISKPKGLVRAPQ

VYTLPPPAEQLSRKDVSLTCLVVGFNPGDISVEWTSNGHTEENYKDTAPV

LDSDGSYFIYSKLNMKTSKWEKTDSFSCNVRHEGLKNYYLKKTISRSPGK*
```

Example 2: Generation of a Monoclonal Antibody Against IL-1 R1

The aim of this project is to generate a monoclonal antibody against IL-1 R1. A population of 5 mice were immunised and screened for positive immune responses. After selecting a suitable candidate for fusion, splenocytes were fused with partner cells to produce a population of hybridomas. This population underwent a series of limiting dilutions and screening assays to produce fully monoclonal cell lines.

Cell Line Nomenclature

The product name "F237 5D1-1A8-2A5" refers to one of the 10 chosen monoclonal hybridoma cell lines. The name is comprised of components describing the production pathway at each stage. Each hybridoma selected from the post-fusion screening and each limiting dilution was given a number corresponding to the plate number and well location on that plate for which the hybridoma was chosen (i.e.

5D1-1A8-2A5). This nomenclature traces the derivation of each individual hybridoma allowing for clear differentiation in the screening process.

Abbreviations

| | |
|---|---|
| Ab | Antibody |
| DMSO | Dimethyl Sulfoxide |
| FCS | Fetal Calf Serum |
| ELISA | Enzyme-Linked Immunosorbent Assay |
| RT | Room Temperature |
| OD | Optical Density |
| PBST | Phosphate-buffered saline + 1% Tween 20 |
| PBS | Phosphate-buffered saline |
| RPM | Revolutions per minute |
| NP, LP, | Mouse Identification: No Punch, |
| RP, LRP, 2LP | Left Punch, Right Punch Left/Right Punch, 2 Left Punches |
| HAT | Hypoxanthine, Aminopterin, Thymidine supplement |
| HATR Media[1] | DMEM supplemented with 2% Roche (HFCS), 2% HAT, 1% Pen/Strep, 1% L-Glutamine |
| SFM | Serum Free Medium |
| PEG | Polyethylene Glycol |
| GAM-HRP | Goat Anti-Mouse-Horse Radish Peroxidase |
| HT | Hypoxanthine and Thymidine |
| LD1 | First Limiting Dilution |
| LD2 | Second Limiting Dilution |

[1]This is the media that was used for all cultures following fusion and screening.

Materials
Reagents and Media

| Reagent | Supplier | Catalogue No. |
|---|---|---|
| L-glutamine | Gibco | 25030-024 |
| HAT Supplement | Gibco | 21060-017 |
| HFCS | Roche | 11363735001 |
| DMEM Glutamax | Gibco | 61965-059 |
| Penicillin/Streptomycin | Gibco | 15140-122 |
| FCS | Gibco | 16000.044 |
| DMSO | Sigma | D2650 |
| Trypan Blue | Sigma | T8154 |
| PEG | Sigma | 10783641001 |
| Freund's Adjuvant Complete | Sigma | F5881 |
| Freund's Adjuvant Incomplete | Sigma | F5506 |
| Sodium Hydrogen Carbonate | VWR | 27778.260 |
| Sodium Carbonate | Sigma | S2127-500G |
| Powdered Milk | Marvel | Original Dried Skimmed |
| Tween 20 (10%) | Sigma | P1379-1L |
| GAM-HRP (Fc Specific) | Sigma | A2554 |
| TMB | Biopanda | TMB-S-002 |
| Mr. Frosty | Nalgene | 55710-200 |

Disposables

| Name | Supplier | Catalogue No. |
|---|---|---|
| 25 cm$^2$ static flasks | Corning | 430639 |
| 75 cm$^2$ static flasks | Corning | 430641 |
| 96-well plate sterile | Corning | 3595 |
| 96-well plate sterile TPP | Primer Scientific | 92696T |
| Cryovials | Fisher Scientific | 366656 |
| Maxi Sorb 96-well plates | Nunc | 442404 |

Equipment
 $CO_2$ Cell culture static incubators (SANYO)
 Plate reader Sunrise (Tecan)
 Centurion Scientific K40R Centrifuge
 Grant-Bio Multishaker PSU 20
Methods
Antigen Preparation Once the immunogen (IL-1R1) was purified, these solutions were diluted to 200 µg/ml in sterile, EF-PBS and aliquoted in volumes of 600 µl for immunisation and 150 µl for boosts and ELISA screening. These aliquots were labelled and stored at −20° C.

Immunisations

A population of 5 BalbC mice were immunised subcutaneously with 200 µl of a 1:1 emulsion of Freund's Adjuvant Complete (Sigma) and a 600 µl aliquot of IL-1 R1 prepared herein. Two weeks after the 1$^{st}$ immunisation, the population was immunized with a 2$^{nd}$ injection at the same volumes and concentrations as the original injection only using Freund's Adjuvant Incomplete (Sigma) instead. One week after the 2$^{nd}$ immunisation, the mice were tagged by ear punches (NP, RP, LP, LRP, 2LP), and test bleeds were screened as described herein for preliminary results. Three weeks after the 2$^{nd}$ immunisation, the population was immunised a 3$^{rd}$ time using the same method as the 2$^{nd}$ injection. One week after the 3$^{rd}$ immunisation, test bleeds were screened, and the mouse with an ear tag of RP was then selected for fusion.

Test Bleed ELISAs

Tail bleeds were taken from the population of 5 BalbC mice and centrifuged at 8000 rpm for 10 min at RT (room temperature). The blood serum from each mouse was collected, loaded onto the plate the same day as screening, and stored at −20° C. This screening was performed twice for the selection of a suitable mouse for fusion.

The day prior to screening, a Maxi Sorp plate was coated by adding 100 µl/well of 50 mM sodium carbonate coating buffer (pH 9.5) containing the IL-1 R1 at 1 µg/ml. A separate coating solution was prepared by diluting APO-A1 in the same coating buffer at 1 µg/ml. These solutions were loaded onto the plate in alternating rows so as to provide two wells to load each sample that demonstrates a positive and negative result. This plate was incubated overnight at 4° C. in static conditions.

The following morning, coating buffer was removed, and 200 µl/well of blocking solution (4.0% w/v semi skim milk powder, 1×PBS) was added and agitated at 150 rpm for 2 hr at RT. The plate was washed three times with PBS-T (0.1% v/v Tween 20). PBS was loaded into each well at 100 µl/well, and 1 µl of each test bleed serum was loaded into each positive and negative well. The plate was incubated at 150 rpm (Grant Shaker) for 2 hrs at room temperature. These samples were then removed and washed four times with PBS-T. 100 µl/well GAM-HRP diluted 1:5000 (Sigma, UK) was added, and the plate was incubated for 1 hr with agitation at 150 rpm at RT. The secondary antibody was removed, and the plate was washed four times with PBS-T and once in PBS. 100 µl/well of TMB substrate solution was added and incubated at 37° C. for 10 minutes. 50 µl 1 M HCl was added per well and the plate immediately read at 450 nm on a Tecan Sunrise plate reader.

After the second test bleed ELISA screening, the mouse with an ear tag of RP was selected for fusion by expressing the most positive immune response.

Boost Injections

One week after the 3$^{rd}$ and final immunization, a boost injection was given to BalbC mouse RP by injecting 100 µl of aliquoted IL-1 R1 at 200 µg/ml without any adjuvant.

Fusion F237

One week before fusion, SP2 cells were broken out from liquid nitrogen and were passaged in 10% FCS DMEM supplemented with 1% Pen/Strep, 1% L-glutamine until 3×12 ml T75 flasks were 75%-90% confluent on the day of fusion. On the day of the fusion, SP2 cells were dislodged by tapping the flask and were centrifuged at 1000 rpm for 5 min at 37° C. The cells were resuspended in 20 ml SFM DMEM, centrifuged again, and resuspended in 10 ml SFM DMEM. SP2 cells were stored in a Sterilin tube in SFM at 37° C., 6% $CO_2$ until needed.

After euthanasia, the spleen was aseptically removed from the mouse that showed the strongest immune response. Splenocytes were extracted by puncturing both ends of the spleen with a fine gauge needle and flushing 10-15 ml SFM DMEM. Splenocytes were transferred to a sterilin tube and washed twice with 20 ml serum free DMEM by centrifugation at 1300 rpm for 5 min at 37° C. and gently removing the supernatant. The splenocytes were resuspended in 10 ml Serum free DMEM in a sterilin tube.

Using the SP2 cells stored at 37° C., the SP2 cells were added to the splenocytes. This SP2/splenocytes culture was centrifuged at 1300 rpm for 5 min at 37° C. After discarding the supernatant, 1 ml PEG was added to the SP2/splenocytes culture dropwise while stirring continuously over a period of 3 min. 1 ml SFM DMEM was added to the fusion mixture and stirred for 4 min. 10 ml SFM DMEM was added dropwise to the fresh culture and incubated for in 37° C. water bath for 5 min. The cells were then centrifuged at 1000 rpm for 5 min at 37° C. The pellet was resuspended in 200 mL HATR media and was plated at 200 μl/well in 10×96 well culture plates which were incubated 11 days at 37° C. in 6% $CO_2$ prior to screening.

Post-Fusion Screening and Post-LD Screening

Eleven days after fusion, protoclones were screened by ELISA. 20× Maxi Sorp 96 well plates were coated as described herein using APO-A1 at 1 μg/ml as the negative control for specificity. The coating solution was removed and the plates were blocked as described herein. Samples were prepared by removing 160 μl of supernatant from each well of the ten fusion plates, limiting dilution plates, or 24-well plates and transferring to fresh 96 well culture plates containing 50 μl 1×PBS. After 2 hours of blocking, the blocking solution was removed, and the plates were washed 3× with PBS-T. The samples from each dilution plate were loaded onto the ELISA plates at 100 μl/well by adding 1 row from each dilution plate per 2 rows on the ELISA plates to account for specificity of the coating antigens. Two wells per ELISA were incubated with 100 μl 1×PBS as a negative control. These samples were incubated at 150 rpm for 2 hours at room temperature.

Limiting Dilutions

Once the hybridoma populations were expanded in 24-well plates and growing well, a secondary screen was performed to select the most specific and highest producing populations for rounds of limiting dilutions.

Both limiting dilutions were performed for 1-3 protoclones each by seeding 2-4×96-well plates at 1 cell/well in 200 μl culture/well. The plates were prepared by counting each culture in the 24-well plate and were diluted 10× as an intermediate dilution, then were diluted to 200 cells in 40 ml. The culture was plated at 200 μl/well and left to incubate at 37° C., 6% $CO_2$ for 7-10 days until the wells were 80%-90% confluent. Each well for both limiting dilutions were screened by ELISA as described herein.

Final Clone Selection

Following the second limiting dilution, 10 clones were selected for expansion in a 24 well plate. Each clone was left to grow in 37° C., 6% $CO_2$ for 6 days until each well became 80%-90% confluent. When the clones were well established in the 24-well plates, each clone at 1 ml/well was transferred to a T25 flask containing 5 ml fresh 10% HATR DMEM for cryopreservation.

Cryopreservation of Monoclonal Cell Lines

Once the clones were well established (80%-90% confluency) in T25 flasks, each 5 ml culture was centrifuged at 1000 rpm for 5 min at 37° C. and was resuspended in 1 ml of fresh 10% DMEM HATR media. Each 1 ml culture was transferred to a cryovial containing 300 μl of a 1:1 ratio of FCS to DMSO. The vials were sealed and placed in a Mr. Frosty and transferred to the −70° C. freezer for short-term storage.

Cell Preparation for Sequencing

Anti-IL-1 R1 produced from clone F237 5D1-1A8-2A5 was selected for sequencing. Once the culture was confluent in the T25 flask, the supernatant was discarded. The cells were dislodged by cell scraping into 2 ml fresh media and were centrifuged at 7,600 rpm for 5 min at RT. The supernatant was then discarded and the pellet was flash frozen in liquid nitrogen and placed in −70° C. until ready for mRNA extraction.

Immunisation and Screening of Test Bleeds

A colony of mice were immunised with an IL-1 R1 immunogen (produced in house in CHO cells) and regular test bleeds were taken over an 11 week period. Test bleeds were screened for IL-1 R1 mAb expression levels using ELISA and internalisation capability using the pHrodo fluorescent assay (Thermo Fisher Scientific, UK https://www-.thermofisher.com/order/catalog/product/P35369 and https://www.sigmaaldrich.com/catalog/product/sigma/m4280?lang=en&region=GB).

Results

Test Bleed 1

One week after the $2^{nd}$ immunisation, a tail bleed was taken from each of the 5 mice and screened against IL-1R and APO-A1 for determination of a suitable animal for fusion and a relative specificity of the polyclonal antibody produced—see FIG. 2.

Test Bleed 2

After screening sera from tail bleeds, the mouse with an ear tag of RP was selected for the fusion of its splenocytes to fusion partner SP2 culture as it demonstrated the best immune response—see FIG. 3.

Post-Fusion Screening

Once the wells in each plate had reached 70%-80% confluency, the plates were screened by ELISA against IL-1 R1 and APO-A1. The hybridoma population producing the highest responses were selected for expansion in a 24-well plate—see FIG. 4.

$1^{st}$ 24-Well Plate Screening

Clones were selected from the post-fusion screening and were arrayed into a 24 well plate for expansion followed by a secondary screening that determines suitable protoclones for the first round of limiting dilutions—see FIG. 5.

Limiting Dilution 1 Screening

Once the $1^{st}$ limiting dilution plates were confluent, the limiting dilution was screened by ELISA against IL-1 R1 and APO-A1. Eleven hybridoma populations were selected from F237 2H12, F237 5D1, and F237 7E6 that demonstrated the highest and most specific response—see FIG. 6.

$2^{nd}$ 24-Well Plate Screening

When the clones became confluent in the 24-well plate, each clone was screened by ELISA against IL-1 R1 and APO-A1. F237-5D1-1A8 was selected for the 2$^{nd}$ round of limiting dilution over 4×96 well plates—see FIG. 7.

Limiting Dilution 2 Screening

Once the wells in each plate had reached 70%-80% confluency, the plates were screened by ELISA against IL-1 R1 and APO-A1. The hybridoma population producing the highest response and highest specificity were selected for expansion in a 24-well plate and cryopreservation—see FIG. 8.

IL-IR1 Internalisation in THP1 Cells was Immunofluorescence Imaged

Fluorescence microscopic images taken from THP1 macrophages treated with LPS and ATP to induce the expression of the IL-1 R1—see FIG. 10. The cells were incubated with mouse serum from several different mice, containing the test antibody against the IL-1 R1, which was conjugated to a pHrodo™ dye (that will only fluoresce within a cell). Strong IL-1 R1 immunoreactivity was observed in the nucleus and cytoplasm of the THP1 cells. IL-1R1 and DAPI staining at ×40 magnification. No staining was observed in the secondary antibody only treated control cells. Images are from four different wells used in two different experiments. The best mouse was selected to take forward to the fusion hybridoma and cloning stages.

THP1 macrophages (see FIG. 11) treated with LPS and ATP to induce the expression of the IL-1R1. The cells were incubated with mouse serum from several mice containing the test monoclonal antibody against the IL-1 R1, which was conjugated to a pHrodo dye (that will only fluoresce within a cell) and analysed with flow cytometry. More fluorescence was seen in the IL-1 R1 antibody treated cells (i) as compared to the control secondary antibody only treated cells (ii). Using this data and that from FIG. 3, the best mouse was chosen to take forward to the fusion hybridoma and cloning stages.

Conclusions

The aim of the project was to produce a range of antibodies against IL-1 R1. Once the mice were immunised and screened, RP was selected for fusion. 10 monoclonal hybridoma cell lines were produced from two rounds of limiting dilutions. Each population was selected by highest production and highest specificity for IL-1 R1. These final cell lines have been frozen down, and the antibody expressed by this cell line will be sequenced.

Example 3: IL-1R1 Monoclonal Antibody Sequencing mRNA was extracted from the hybridoma cell pellets. Total RNA was extracted from the pellets using a conventional RNA extraction protocol. Cell pellets were homogenised using RNA STAT-60 reagent. Upon addition of chloroform, the homogenate separated into an aqueous phase and an organic phase, and total RNA was isolated in the aqueous phase. Isopropanol was used to precipitate the RNA, followed by ethanol washes and solubilisation in water.

RT-PCR cDNA was created from the RNA by reverse-transcription with an oligo(dT) primer. PCR reactions are set up using variable domain primers to amplify both the VH and VL regions of the monoclonal antibody DNA giving the following bands—see FIG. 12.

The VH and VL products were cloned into the Invitrogen sequencing vector pCR2.1 and transformed into TOP10 cells and screened by PCR for positive transformants. Selected colonies were picked and analyzed by DNA sequencing on an ABI3130xI Genetic Analyzer, the result may be seen below.

Sequencing Results

Heavy Chain
$V_H$ Amino Acid Sequence Alignment:

```
                         1                                                  50
VH1.1         (1)   MEWSCVML FLMAAAQSIQAQIQLVQSGPELRKPGETVRISCKASGYPFTT
VH1.4         (1)   MECSCVML FLMAAAQSIQAQIQLVQSGPELRKPGETVRISRKASGYPFTT
VH1.3         (1)   MGWSWVML FLMAAAQSIQAQIQLVQSGPELRKPGETVRISCKASGYPFTT
VH2.1         (1)   MGWVWNLL FLMAAAQSIQAQIQLVQSGPELRKPGETVRISCKASGYPFTT
VH2.5         (1)   MGWVWTLP FLMAAAQSIQAQIQLVQSGPELRKPGETVRISCKASGYPFTT
VH2.3         (1)   MGWVWNLP FLMAAAQSIQAQIQLVQSGPELRKPGETVRISCKASGYPFTT
VH1.2         (1)   MDWVWTLP FLMAAAQSIQAQIQLVQSGPELRKPGETVRISCKASGYPFTT
VH2.4         (1)   MDWLWNLP FLMAAAQSIQAQIQLVQSGPELRKPGETVRISCKASGYPFTT
Consensus     (1)   MGWVWNLPFLMAAAQSIQAQIQLVQSGPELRKPGETVRISCKASGYPFTT 51                                                 100
VH1.1        (51)   AGLQWVQKMSGKGLKWIGWMNTQSEVPKYAEEFKGRIAFSLETAASTAYL
VH1.4        (51)   AGLQWVQKMSGKGLKWIGWMNTQSEVPKYAEEFKGRIAFSLETAASTAYL
VH1.3        (51)   AGLQWVQKMSGKGLKWIGWMNTQSEVPKYAEEFKGRIAFSLETAASTAYL
VH2.1        (51)   AGLQWVQKMSGKGLKWIGWMNTQSEVPKYAEEFKGRIAFSLETAASTAYL
VH2.5        (51)   AGLQWVQKMSGKGLKWIGWMNTQSEVPKYAEEFKGRIAFSLETAASTAYL
VH2.3        (51)   AGLQWVQKMSGKGLKWIGWMNTQSEVPKYAEEFKGRIAFSLETAASTAYL
VH1.2        (51)   AGLQWVQKMSGKGLKWIGWMNTQSEVPKYAEEFKGRIAFSLETAASTAYL
VH2.4        (51)   AGLQWVQKMSGKGLKWIGWMNTQSEVPKYAEEFKGRIAFSLETAASTAYL
Consensus    (51)   AGLQWVQKMSGKGLKWIGWMNTQSEVPKYAEEFKGRIAFSLETAASTAYL 101                                                150
VH1.1       (101)   QINNLKTEDTATYFCAKSVYFWWRYFDVWGAGTTVTVSSAKTTPPPVYPL
VH1.4       (101)   QINNLKTEDTATYFCAKSVYFWWRYFDVWGAGTTVTVSSAKTTPPSVFPL
VH1.3       (101)   QINNLKTEDTATYFCAKSVYFWWRYFDVWGAGTTVTVSSAKTTPPPVYPL
VH2.1       (101)   QINNLKTEDTATYFCAKSVYFWWRYFDVWGAGTTVTVSSAKTTPPPVYPL
VH2.5       (101)   QINNLKTEDTATYFCAKSVYFWWRYFDVWGAGTTVTVSSAKTTPPPVYPL
VH2.3       (101)   QINNLKTEDTATYFCAKSVYFWWRYFDVWGAGTTVTVSSAKTTPPPVYPL
```

-continued

| Heavy Chain $V_H$ Amino Acid Sequence Alignment: | | |
|---|---|---|
| VH1.2 | (101) | QINNLKTEDTATYFCAKSVYFWWRYFDVWGAGTTVTVSSAKTTPPSVYPL |
| VH2.4 | (101) | QINNLKTEDTATYFCAKSVYFWWRYFDVWGAGTTVTVSSAKTTPPPVYPL |
| Consensus | (101) | QINNLKTEDTATYFCAKSVYFWWRYFDVWGAGTTVTVSSAKTTPPPVYPL |
|  |  | 151 |
| VH1.1 | (151) | A |
| VH1.4 | (151) | A |
| VH1.3 | (151) | A |
| VH2.1 | (151) | V |
| VH2.5 | (151) | V |
| VH2.3 | (151) | A |
| VH1.2 | (151) | A |
| VH2.4 | (151) | A |
| Consensus | (151) | A |
|  |  |  |
| VH1.1 | (SEQ ID NO: 2) |  |
| VH1.4 | (SEQ ID NO: 3) |  |
| VH1.3 | (SEQ ID NO: 4) |  |
| VH2.1 | (SEQ ID NO: 5) |  |
| VH2.5 | (SEQ ID NO: 6) |  |
| VH2.3 | (SEQ ID NO: 7) |  |
| VH1.2 | (SEQ ID NO: 8) |  |
| VH2.4 | (SEQ ID NO: 9) |  |
| Consensus | (SEQ ID NO: 7) |  |

Key to amino acid shading:
Black      non-similar residues
Bold       consensus residue derived from a block of residues at
           a given position
Underlined residues similar in structure to consensus residue or
           each other when no consensus found
Italicised consensus residue derived from a completely conserved
           residue at a given position
Underlined/ residue weakly similar to consensus residue at given
italicized  position $V_H$ Consensus Amino Acid Sequence:

(SEQ ID NO: 7)
MGWVWNLPFLMAAAQSIQAQIQLVQSGPELRKPGETVRISCKASGYPFTT

AGLQINVQKMSGKGLKWIGWMNTQSEVPKYAEEFKGRIAFSLETAASTAY

LQINNLKTEDTATYFCAKSVYFNWRYFDVWGAGTTVTVSSAKTTPPPVYP

LA

The variable domain is highlighted in BOLD.
The Complementarity Determining Regions (CDRs) are underlined as determined by the IMGT numbering system (Lefranc, M.-P. et al., Nucleic Acids Research, 27, 209-212 (1999))—see FIG. 13.
Key to Amino Acid Shading, in FIG. 13:
Blue shaded circles are hydrophobic (non-polar) residues in frameworks 1-3 at sites that are hydrophobic in the majority of antibodies.
Yellow shaded circles are proline residues.
Squares are key residues at the start and end of the CDR.
Red amino acids in the framework are structurally conserved amino acids.

| Light Chain $V_L$ Amino Acid Sequence Alignment: | | |
|---|---|---|
|  |  | 1                                                  50 |
| VK1.1 | (1) | MRAPAQFLGLLLLWTSASRCDIVMTQSPATLSVTPGDRVSLSCRASQSIS |
| VK1.5 | (1) | MRAPAQLLGLLLFWTSASRCDIVMTQSPATLSVTPGDRVSLSCRASQSIS |
| VK1.3 | (1) | MRSPAQFLGLLLFWTSASRCDIVMTQSPATLSVTPGDRVSLSCRASQSIS |
| VK1.4 | (1) | MRSPAQFLGLLLFWTSASRCDIVMTQSPATLSVTPGDRVSLSCRASQSIS |
| VK2.1 | (1) | MVSSAQFLGLLLFWTSASRCDIVMTQSPATLSVTPGDRVSLSCRASQSIS |
| VK2.6 | (1) | MVSTAQFLGLLLFWTSASRCDIVMTQSPATLSVTPGDRVSLSCRASQSIS |
| Consensus | (1) | MRSPAQFLGLLLFWTSASRCDIVMTQSPATLSVTPGDRVSLSCRASQSIS |
|  |  | 51                                                100 |
| VK1.1 | (51) | DYLSWYQQRSHESPRLIIKYASQSISGIPSRFSGSGSGSDFTLSINSVEP |
| VK1.5 | (51) | DYLSWYQQRSHESPRLIIKYASQSISGIPSRFSGSGSGSDFTLNINSVEP |
| VK1.3 | (51) | DYLSWYQQRSHESPRLIIKYASQSISGIPSRFSGSGSGSDFTLSINSVEP |
| VK1.4 | (51) | DYLSWYQQRSHESPRLIIKYASQSISGIPSRFSGSGSGSDFTLSINSVEP |
| VK2.1 | (51) | DYLSWYQQRSHESPRLIIKYASQSISGIPSRFSGSGSGSDFTLSINSVEP |
| VK2.6 | (51) | DYLSWYQQRSHESPRLIIKYASQSISGIPSRFSGSGSGSDFTLSINSVEP |
| Consensus | (51) | DYLSWYQQRSHESPRLIIKYASQSISGIPSRFSGSGSGSDFTLSINSVEP |

Light Chain
V_L Amino Acid Sequence Alignment:

```
                    101                                               150
VK1.1       (101)   EDVGVYYCQHGHSFPLTFGSGTKLELKRADAAPTVSIFPPSSEQLTSGGA
VK1.5       (101)   EDVGVYYCQHGHSFPLTFGSGTKLELKRADAAPTVSIFPPSSEQLTSGGA
VK1.3       (101)   EDVGVYYCQHGHSFPLTFGSGTKLELKRADAAPTVSIFPPSSEQLTSGGA
VK1.4       (101)   EDVGVYYCQHGHSFPLTFGSGTKLELKRADAAPTVSIFPPSSEQLTSGGA
VK2.1       (101)   EDVGVYYCQHGHSFPLTFGSGTKLELKRADAAPTVSIFPPSSEQLTSGGA
VK2.6       (101)   EDVGVYYCQHGHSFPLTFGSGTKLELKRADAAPTVSIFPPSSEQLTSGGA
Consensus   (101)   EDVGVYYCQHGHSFPLTFGSGTKLELKRADAAPTVSIFPPSSEQLTSGGA 151       162
VK1.1       (151)   SVVCFLNNFYFK
VK1.5       (151)   SVVCFLNNFYFK
VK1.3       (151)   SVVCFLNNFYFK
VK1.4       (151)   SVVCFLNNFYFR
VK2.1       (151)   SVVCFLNNFYFK
VK2.4       (151)   SVVCFLNNFYFR
Consensus   (151)   SVVCFLNNFYFK VK1.1       (SEQ ID NO: 10)
VK1.5       (SEQ ID NO: 11)
VK1.3       (SEQ ID NO: 12)
VK1.4       (SEQ ID NO: 13)
VK2.1       (SEQ ID NO: 14)
VK2.6       (SEQ ID NO: 15)
Consensus   (SEQ ID NO: 12)
```

Key to amino acid shading:
Black — non-similar residues
Bold — consensus residue derived from a block of residues at a given position
Underlined — residues similar in structure to consensus residue or each other when no consensus found
Italicised — consensus residue derived from a completely conserved residue at a given position
Underlined/italicized — residue weakly similar to consensus residue at given position V_L Consensus Amino Acid Sequence:

(SEQ ID NO: 12)
MRSPAQFLGLLLFWTSASRCDIVMTQSPATLSVTPGDRVSLSCRAS<u>QSIS</u>

<u>DYLSWYQQRSHESPRLIIK</u>YAS<u>QSISGIPSRFSGSGSGSDFTLSINSVEP</u>

EDVGVYYC<u>QHGHSFPLT</u>FGSGTKLELKRADAAPTVSIFPPSSEQLTSGGA

SVVCFLNNFYPK

The variable domain is highlighted in BOLD.

The Complementarity Determining Regions (CDRs) are underlined as determined by the IMGT numbering system (Lefranc, M.-P. et al., Nucleic Acids Research, 27, 209-212 (1999))—see FIG. 14.

Key to Amino Acid Shading, in FIG. 14:

Blue shaded circles are hydrophobic (non-polar) residues in frameworks 1-3 at sites that are hydrophobic in the majority of antibodies.

Yellow shaded circles are proline residues.

Squares are key residues at the start and end of the CDR.

Red amino acids in the framework are structurally conserved amino acids.

VH Sequencing results:
VH1.1 DNA Sequence:
(SEQ ID NO: 16)
ATGGAATGGAGCTGTGTCATGCTCTTTCTCATGGC

AGCAGCTCAAAGTATCCAAGCACAGATCCAGTTGG

TGCAGTCTGGACCTGAGCTGAGGAAGCCTGGAGAG

ACAGTCAGGATCTCCTGCAAGGCCTCTGGGTATCC

CTTCACAACTGCTGGATTGCAGTGGGTACAGAAGA

TGTCAGGAAAGGGTTTGAAATGGATTGGCTGGATG

AACACCCAGTCTGAAGTGCCAAAATATGCAGAAGA

GTTCAAGGGACGGATTGCCTTCTCTTTGGAAACCG

CTGCCAGTACTGCATATTTACAGATAAACAACCTC

AAAACTGAGGACACGGCAACGTATTTCTGTGCGAA

ATCGGTCTATTTTAACTGGAGATATTTCGATGTCT

GGGGTGCAGGGACCACGGTCACCGTCTCCTCAGCC

AAAACGACACCCCCACCCGTTTATCCACTGGCC

VH1.1 Amino Acid Sequence:
(SEQ ID NO: 2)
MEWSCVMLFLMAAAQSIQAQIQLVQSGPELRKPGE

TVRISCKASGYPFTTAGLQWVQKMSGKGLKWIGWM

NTQSEVPKYAEEFKGRIAFSLETAASTAYLQINNL

KTEDTATYFCAKSVYFNWRYFDVWGAGTTVTVSSA

KTTPPPVYPLA

-continued

VH1.3 DNA Sequence:
(SEQ ID NO: 17)
ATGGGATGGAGCTGGGTCATGCTCTTTCTCATGGC
AGCAGCTCAAAGTATCCAAGCACAGATCCAGTTGG
TGCAGTCTGGACCTGAGCTGAGGAAGCCTGGAGAG
ACAGTCAGGATCTCCTGCAAGGCTTCTGGGTATCC
CTTCACAACTGCTGGACTGCAGTGGGTACAGAAGA
TGTCAGGAAAGGGTTTGAAATGGATTGGCTGGATG
AACACCCAGTCTGAAGTGCCAAAATATGCAGAAGA
GTTCAAGGGACGGATTGCCTTCTCTTTGGAAACCG
CTGCCAGTACTGCATATTTACAGATAAACAACCTC
AAAACTGAGGACACGGCAACGTATTTCTGTGCGAA
ATCGGTCTATTTTAACTGGAGATATTTCGATGTCT
GGGGTGCAGGGACCACGGTCACCGTCTCCTCAGCC
AAAACGACACCCCCACCCGTTTATCCCTTGGCC VH1.3 Amino Acid Sequence:
(SEQ ID NO: 4)
MGWSWVMLFLMAAAQSIQAQIQLVQSGPELRKPGE
TVRISCKASGYPFTTAGLQVVVQKMSGKGLKWIGW
MNTQSEVPKYAEEFKGRIAFSLETAASTAYLQINN
LKTEDTATYFCAKSVYFNWRYFDVWGAGTTVTVSS
AKTTPPPVYPLA VH1.4 DNA Sequence:
(SEQ ID NO: 18)
ATGGAATGCAGCTGTGTAATGCTCTTTCTCATGGC
AGCAGCTCAAAGTATCCAAGCACAGATCCAGTTGG
TGCAGTCTGGACCTGAGCTGAGGAAGCCTGGAGAG
ACAGTCAGGATCTCCCGCAAGGCTTCTGGGTATCC
CTTCACAACTGCTGGATTGCAGTGGGTACAGAAGA
TGTCAGGAAAGGGTTTGAAATGGATTGGCTGGATG
AACACCCAGTCTGAAGTGCCAAAATATGCAGAAGA
GTTCAAGGGACGGATTGCCTTCTCTTTGGAAACCG
CTGCCAGTACTGCATATTTACAGATAAACAACCTC
AAAACTGAGGACACGGCAACGTATTTCTGTGCGAA
ATCGGTCTATTTTAACTGGAGATATTTCGATGTCT
GGGGTGCAGGGACCACGGTCACCGTCTCCTCAGCC
AAAACGACACCCCCATCCGTCTTCCCCCTGGCA VH1.4 Amino Acid Sequence:
(SEQ ID NO: 3)
MECSCVMLFLMAAAQSIQAQIQLVQSGPELRKPGE
TVRISRKASGYPFTTAGLQWVQKMSGKGLKWIGWM
NTQSEVPKYAEEFKGRIAFSLETAASTAYLQINNL
KTEDTATYFCAKSVYFNWRYFDVWGAGTTVTVSSA
KTTPPSVFPLA VH2.1 DNA Sequence:
(SEQ ID NO: 19)
ATGGGTTGGGTGTGGAACTTGCTATTCCTCATGGC
AGCAGCTCAAAGTATCCAAGCACAGATCCAGCTGG
TGCAGTCTGGACCTGAGCTGAGGAAGCCTGGAGAG
ACAGTCAGGATCTCCTGCAAGGCTTCTGGGTATCC
CTTCACAACTGCTGGATTGCAGTGGGTACAGAAGA
TGTCAGGAAAGGGTTTGAAATGGATTGGCTGGATG
AACACCCAGTCTGAAGTGCCAAAATATGCAGAAGA
GTTCAAGGGACGGATTGCCTTCTCTTTGGAAACCG
CTGCCAGTACTGCATATTTACAGATAAACAACCTC
AAAACTGAGGACACGGCAACGTATTTCTGTGCGAA
ATCGGTCTATTTTAACTGGAGATATTTCGATGTCT
GGGGTGCAGGGACCACGGTCACCGTCTCCTCAGCC
AAAACGACACCCCCACCCGTCTATCCACTGGTC VH2.1 Amino Acid Sequence:
(SEQ ID NO: 5)
MGWVWNLLFLMAAAQSIQAQIQLVQSGPELRKPGE
TVRISCKASGYPFTTAGLQWVQKMSGKGLKWIGWM
NTQSEVPKYAEEFKGRIAFSLETAASTAYLQINNL
KTEDTATYFCAKSVYFNWRYFDVWGAGTTVTVSSA
KTTPPPVYPLV VH1.2 DNA Sequence:
(SEQ ID NO: 20)
ATGGATTGGGTGTGGACCTTGCCATTCCTCATGGC
AGCAGCTCAAAGTATCCAAGCACAGATCCAGTTGG
TGCAGTCTGGACCTGAGCTGAGGAAGCCTGGAGAG
ACAGTCAGGATCTCCTGCAAGGCTTCTGGGTATCC
CTTCACAACTGCTGGATTGCAGTGGGTACAGAAGA
TGTCAGGAAAGGGTTTGAAATGGATTGGCTGGATG
AACACCCAGTCTGAAGTGCCAAAATATGCAGAAGA
GTTCAAGGGACGGATTGCCTTCTCTTTGGAAACCG
CTGCCAGTACTGCATATTTACAGATAAACAACCTC
AAAACTGAGGACACGGCAACGTATTTCTGTGCGAA
ATCGGTCTATTTTAACTGGAGATATTTCGATGTCT
GGGGTGCAGGGACCACGGTCACCGTCTCCTCAGCC
AAAACGACACCCCCATCTGTCTATCCACTGGCC VH1.2 Amino Acid Sequence:
(SEQ ID NO: 8)
MDWVVVTLPFLMAAAQSIQAQIQLVQSGPELRKPG
ETVRISCKASGYPFTTAGLQWVQKMSGKGLKWIGW
MNTQSEVPKYAEEFKGRIAFSLETAASTAYLQINN
LKTEDTATYFCAKSVYFNWRYFDVWGAGTTVTVSS
AKTTPPSVYPLA VH2.3 DNA Sequence:
(SEQ ID NO: 21)
ATGGGTTGGGTGTGGAACTTGCCATTCCTCATGGC

AGCAGCTCAAAGTATCCAAGCACAGATCCAGTTGG

TGCAGTCTGGACCTGAGCTGAGGAAGCCTGGAGAG

ACAGTCAGGATCTCCTGCAAGGCTTCTGGGTATCC

CTTCACAACTGCTGGATTGCAGTGGGTACAGAAGA

TGTCAGGAAAGGGTTTGAAATGGATTGGCTGGATG

AACACCCAGTCTGAAGTACCAAAATATGCAGAAGA

GTTCAAGGGACGGATTGCCTTCTCTTTGGAAACCG

CTGCCAGCACTGCATATTTACAGATAAACAACCTC

AAAACTGAGGACACGGCAACGTATTTCTGTGCGAA

ATCGGTCTATTTTAACTGGAGATATTTCGATGTCT

GGGGTGCAGGGACCACGGTCACCGTCTCCTCAGCC

AAAACGACACCCCCACCCGTCTATCCATTGGCC

VH2.3 Amino Acid Sequence:
(SEQ ID NO: 7)
MGWVWNLPFLMAAAQSIQAQIQLVQSGPELRKPGE

TVRISCKASGYPFTTAGLQVVVQKMSGKGLKWIGW

MNTQSEVPKYAEEFKGRIAFSLETAASTAYLQINN

LKTEDTATYFCAKSVYFNWRYFDVWGAGTTVTVSS

AKTTPPPVYPLA

VH2.4 DNA Sequence:
(SEQ ID NO: 22)
ATGGATTGGCTGTGGAACTTGCCATTCCTCATGGC

AGCAGCTCAAAGTATCCAAGCACAGATCCAGTTGG

TGCAGTCTGGACCTGAGCTGAGGAAGCCTGGAGAG

ACAGTCAGGATCTCCTGCAAGGCTTCTGGGTATCC

CTTCACAACTGCTGGATTGCAGTGGGTACAGAAGA

TGTCAGGAAAGGGTTTGAAATGGATTGGCTGGATG

AACACCCAGTCTGAAGTGCCAAAATATGCAGAAGA

GTTCAAGGGACGGATTGCCTTCTCTTTGGAAACCG

CTGCCAGTACTGCATATTTACAGATAAACAACCTC

AAAACTGAGGACACGGCAACGTATTTCTGTGCGAA

ATCGGTCTATTTTAACTGGAGATATTTCGATGTCT

GGGGTGCAGGGACCACGGTCACCGTCTCCTCAGCC

AAAACGACACCCCCACCCGTCTATCCACTGGCC

VH2.4 Amino Acid Sequence:
(SEQ ID NO: 9)
MDWLWNLPFLMAAAQSIQAQIQLVQSGPELRKPGE

TVRISCKASGYPFTTAGLQVVVQKMSGKGLKWIGW

MNTQSEVPKYAEEFKGRIAFSLETAASTAYLQINN

LKTEDTATYFCAKSVYFNWRYFDVWGAGTTVTVSS

AKTTPPPVYPLA

VH2.5 DNA Sequence:
(SEQ ID NO: 23)
ATGGGTTGGGTGTGGACCTTGCCATTCCTCATGGC

AGCAGCTCAAAGTATCCAAGCACAGATCCAGTTGG

TGCAGTCTGGACCTGAGCTGAGGAAGCCTGGAGAG

ACAGTCAGGATCTCCTGCAAGGCTTCTGGGTATCC

CTTCACAACTGCTGGATTGCAGTGGGTACAGAAGA

TGTCAGGAAAGGGTTTGAAATGGATTGGCTGGATG

AACACCCAGTCTGAAGTGCCAAAATATGCAGAAGA

GTTCAAGGGACGGATTGCCTTCTCTTTGGAAACCG

CTGCCAGTACTGCATATTTACAGATAAACAACCTC

AAAACTGAGGACACGGCGACGTATTTCTGTGCGAA

ATCGGTCTATTTTAACTGGAGATATTTCGATGTCT

GGGGTGCAGGGACCACGGTCACCGTCTCCTCAGCC

AAAACGACACCCCCACCCGTCTATCCCTGGTC

VH2.5 Amino Acid Sequence:
(SEQ ID NO: 6)
MGWVWTLPFLMAAAQSIQAQIQLVQSGPELRKPGE

TVRISCKASGYPFTTAGLQWVQKMSGKGLKWIGWM

NTQSEVPKYAEEFKGRIAFSLETAASTAYLQINNL

KTEDTATYFCAKSVYFNWRYFDVWGAGTTVTVSSA

KTTPPPVYPLV

VL Sequencing Results:

VK1.1 DNA Sequence:
(SEQ ID NO: 24)
ATGAGGGCCCCTGCTCAGTTTCTTGGGCTTTTGCT

TCTCTGGACTTCAGCCTCCAGATGTGACATTGTGA

TGACTCAGTCTCCAGCCACCCTGTCTGTGACTCCA

GGAGATAGAGTCTCTCTTTCCTGCAGGGCCAGCCA

GAGTATTAGCGACTACTTATCCTGGTATCAACAAA

GATCTCATGAGTCTCCAAGGCTTATCATCAAATAT

GCTTCCCAATCCATCTCTGGGATCCCCTCCAGGTT

CAGTGGCAGTGGATCAGGGTCAGACTTCACTCTCA

GTATCAACAGTGTGGAACCTGAAGATGTTGGAGTG

TATTACTGTCAACATGGTCACAGCTTTCCGCTCAC

GTTCGGTTCTGGGACCAAGCTGGAGCTGAAACGGG

CTGATGCTGCACCAACTGTATCCATCTTCCCACCA

TCCAGTGAGCAGTTAACATCTGGAGGTGCCTCAGT

CGTGTGCTTCTTGAACAACTTCTACCCCAAAGA

VK1.1 Amino Acid Sequence:
(SEQ ID NO: 10)
MRAPAQFLGLLLLWTSASRCDIVMTQSPATLSVTP

GDRVSLSCRASQSISDYLSWYQQRSHESPRLIIKY

ASQSISGIPSRFSGSGSGSDFTLSINSVEPEDVGV

YYCQHGHSFPLTFGSGTKLELKRADAAPTVSIFPP

SSEQLTSGGASVVCFLNNFYPK

VK1.3 DNA Sequence:
(SEQ ID NO: 25)
ATGAGGTCCCCTGCTCAGTTCCTTGGGCTTTTGCT

TTTCTGGACTTCAGCCTCCAGATGTGACATTGTGA

TGACTCAGTCTCCAGCCACCCTGTCTGTGACTCCA

GGAGATAGAGTCTCTCTTTCCTGCAGGGCCAGCCA

GAGTATTAGCGACTACTTATCCTGGTATCAACAAA

GATCTCATGAGTCTCCAAGGCTTATCATCAAATAT

GCTTCCCAATCCATCTCTGGGATCCCCTCCAGGTT

CAGTGGCAGTGGATCAGGGTCAGACTTCACTCTCA

GTATCAACAGTGTGGAACCTGAAGATGTTGGAGTG

TATTACTGTCAACATGGTCACAGCTTTCCGCTCAC

GTTCGGTTCTGGGACCAAGCTGGAGCTGAAACGGG

CTGATGCTGCACCAACTGTATCCATCTTCCCACCA

TCCAGTGAGCAGTTAACATCTGGAGGTGCCTCAGT

CGTGTGCTTCTTGAACAACTTCTACCCCAAA

VK1.3 Amino Acid Sequence:
(SEQ ID NO: 12)
MRSPAQFLGLLLFWTSASRCDIVMTQSPATLSVTP

GDRVSLSCRASQSISDYLSWYQQRSHESPRLIIKY

ASQSISGIPSRFSGSGSGSDFTLSINSVEPEDVGV

YYCQHGHSFPLTFGSGTKLELKRADAAPTVSIFPP

SSEQLTSGGASVVCFLNNFYPK

VK1.4 DNA Sequence:
(SEQ ID NO: 26)
ATGAGGTCCCCAGCTCAGTTTCTGGGGCTTTTGCT

TTTCTGGACTTCAGCCTCCAGATGTGACATTGTGA

TGACTCAGTCTCCAGCCACCCTGTCTGTGACTCCA

GGAGATAGAGTCTCTCTTTCCTGCAGGGCCAGCCA

GAGTATTAGCGACTACTTATCCTGGTATCAACAAA

GATCTCATGAGTCTCCAAGGCTTATCATCAAATAT

GCTTCCCAATCCATCTCTGGGATCCCCTCCAGGTT

CAGTGGCAGTGGATCAGGGTCAGACTTCACTCTCA

GTATCAACAGTGTGGAACCTGAAGATGTTGGAGTG

TATTACTGTCAACATGGTCACAGCTTTCCGCTCAC

GTTCGGTTCTGGGACCAAGCTGGAGCTGAAACGGG

CTGATGCTGCACCAACTGTATCCATCTTCCCACCA

TCCAGTGAGCAGTTAACATCTGGAGGTGCCTCAGT

CGTGTGCTTCTTGAACAACTTCTACCCCAGAGA

VK1.4 Amino Acid Sequence:
(SEQ ID NO: 13)
MRSPAQFLGLLLFWTSASRCDIVMTQSPATLSVTP

GDRVSLSCRASQSISDYLSWYQQRSHESPRLIIKY

ASQSISGIPSRFSGSGSGSDFTLSINSVEPEDVGV

YYCQHGHSFPLTFGSGTKLELKRADAAPTVSIFPP

SSEQLTSGGASVVCFLNNFYPR

VK1.5 DNA Sequence:
(SEQ ID NO: 27)
ATGAGGGCCCCTGCTCAGCTCCTGGGGCTTTTGCT

TTTCTGGACTTCAGCCTCCAGATGTGACATTGTGA

TGACTCAGTCTCCAGCCACCCTGTCTGTGACTCCA

GGAGATAGAGTCTCTCTTTCCTGCAGGGCCAGCCA

GAGTATTAGCGACTACTTATCCTGGTATCAACAAA

GATCTCATGAGTCTCCAAGGCTTATCATCAAATAT

GCTTCCCAATCCATCTCTGGGATCCCCTCCAGGTT

CAGTGGCAGTGGATCAGGGTCAGACTTCACTCTCA

ATATCAACAGTGTGGAACCTGAAGATGTTGGAGTG

TATTACTGTCAACATGGTCACAGCTTTCCGCTCAC

GTTCGGTTCTGGGACCAAGCTGGAGCTGAAACGGG

CTGATGCTGCACCAACTGTATCCATCTTCCCACCA

TCCAGTGAGCAGTTAACATCTGGAGGTGCCTCAGT

CGTGTGCTTCTTGAACAACTTCTATCCCAAAGA

VK1.5 Amino Acid Sequence:
(SEQ ID NO: 11)
MRAPAQLLGLLLFWTSASRCDIVMTQSPATLSVTP

GDRVSLSCRASQSISDYLSWYQQRSHESPRLIIKY

ASQSISGIPSRFSGSGSGSDFTLNINSVEPEDVGV

YYCQHGHSFPLTFGSGTKLELKRADAAPTVSIFPP

SSEQLTSGGASVVCFLNNFYPK

VK2.1 DNA Sequence:
(SEQ ID NO: 28)
ATGGTATCCTCAGCTCAGTTCCTTGGACTTTTGCT

TTTCTGGACTTCAGCCTCCAGATGTGACATTGTGA

TGACTCAGTCTCCAGCCACCCTGTCTGTGACTCCA

GGAGATAGAGTCTCTCTTTCCTGCAGGGCCAGCCA

GAGTATTAGCGACTACTTATCCTGGTATCAACAAA

GATCTCATGAGTCTCCAAGGCTTATCATCAAATAT

GCTTCCCAATCCATCTCTGGGATCCCCTCCAGGTT

CAGTGGCAGTGGATCAGGGTCAGACTTCACTCTCA

GTATCAACAGTGTGGAACCTGAAGATGTTGGAGTG

TATTACTGTCAACATGGTCACAGCTTTCCGCTCAC

GTTCGGTTCTGGGACCAAGCTGGAGCTGAAACGGG

CTGATGCTGCACCAACTGTATCCATCTTCCCACCA

```
-continued
TCCAGTGAGCAGTTAACATCTGGAGGTGCCTCAGT

CGTGTGCTTCTTGAACAACTTCTACCCCAAA

VK2.1 Amino Acid Sequence:
                             (SEQ ID NO: 14)
MVSSAQFLGLLLFWTSASRCDIVMTQSPATLSVTP

GDRVSLSCRASQSISDYLSWYQQRSHESPRLIIKY

ASQSISGIPSRFSGSGSGSDFTLSINSVEPEDVGV

YYCQHGHSFPLTFGSGTKLELKRADAAPTVSIFPP

SSEQLTSGGASVVCFLNNFYPK

VK2.6 DNA Sequence:
                             (SEQ ID NO: 29)
ATGGTGTCCACAGCTCAGTTCCTTGGACTTTTGCT

TTTCTGGACTTCAGCCTCCAGATGTGACATTGTGA

TGACTCAGTCTCCAGCCACCCTGTCTGTGACTCCA

GGAGATAGAGTCTCTCTTTCCTGCAGGGCCAGCCA

GAGTATTAGCGACTACTTATCCTGGTATCAACAAA

GATCTCATGAGTCTCCAAGGCTTATCATCAAATAT

GCTTCCCAATCCATCTCTGGGATCCCCTCCAGGTT

CAGTGGCAGTGGATCAGGGTCAGACTTCACTCTCA

GTATCAACAGTGTGGAACCTGAAGATGTTGGAGTG

TATTACTGTCAACATGGTCACAGCTTTCCGCTCAC

GTTCGGTTCTGGGACCAAGCTGGAGCTGAAACGGG

CTGATGCTGCACCAACTGTATCCATCTTCCCACCA

TCCAGTGAGCAGTTAACATCTGGAGGTGCCTCAGT

CGTGTGCTTCTTGAACAACTTCTACCCCAGAGA

VK2.6 Amino Acid Sequence:
                             (SEQ ID NO: 15)
MVSTAQFLGLLLFWTSASRCDIVMTQSPATLSVTP

GDRVSLSCRASQSISDYLSWYQQRSHESPRLIIKY

ASQSISGIPSRFSGSGSGSDFTLSINSVEPEDVGV

YYCQHGHSFPLTFGSGTKLELKRADAAPTVSIFPP

SSEQLTSGGASVVCFLNNFYPR
```

Example 4—NLRP3 Antigen Synthesis

Design of a peptide (antigen) to NLRP3 that will generate an antibody response capable of inhibiting formation of the NLRP3 inflammasome.

The NLRP-3 inflammasome is a heterogenous protein complex that forms in mammalian cells in response to inflammatory stimulus, the ability to regulate and attenuate its formation could have important therapeutic potential for a range of inflammatory disorders. A peptide will be designed, derived from the NALP3 protein sequence which should generate antibodies capable of blocking the binding of NALP3 to the other protein components in the NLRP3 inflammasome complex.

NLRP3 activation occurs by the self-assembly of NLRP protein with ASC, which is a hetero-complex of CARD, PYD and Caspase-1 domains. NLRP3 and ASC interact through their respective PYD domains, which contain a large proportion of highly conserved charged amino acid residues which interact to form electrostatic interactions, which stabilize the complex—see FIG. 15.

FIG. 16 shows sequence alignment using CLUSTAL 0 (1.2.4) of the consensus sequences of C-terminal domains of human and mouse NALP (NLRP) proteins. Red indicates a residue recognized as essential for NLRP/ASC interaction by site-directed mutagenesis (Vajjhala et al, 2012).

Peptide selection was concentrated on the sequence region from 1-61 which has been studied extensively and is involved in the interaction with ASC (Vajjhala et al, 2012). The region has also been well modelled by crystallography, with a number of PDB structures available for this domain. PDB model 3QF2, which consists of the PYR domain of NLRP3 was selected as the most useful PDB structural reference. Initial peptide candidate sequences were selected on the basis of accessibility and visibility as potential epitopes, and also degree of similarity between mouse and human sequence, whilst maintaining difference with other NLRP variants. These initial 3 peptides were modelled into 3D structures using NovaFold.

NovaFold Analysis

NovaFold is a 3D protein modelling software that uses the I-TASSER algorithm, a combination of template based threading (from PDB) and ab initio methods to predict the folding of a protein or peptide. It is used in this context to predict the presence of secondary structural features within a peptide which are known to be exhibited by the sequence in situ within the parent protein. This can help optimise the selection of a peptide sequence which best reflects the folding and proximity based relationships within the parent protein, helping to maximize the potential of the immunogenic protein resulting in an antibody with full activity towards the corresponding epitope in the full length protein.

Modelling of Peptides and Alignment

Four distinct sequences were modelled using NovaFold, and the resulting highest scoring models were assessed and then aligned to the parent NLRP3 structure as represented by PDB:3QF2.

TABLE 2

Comparison of alignment and structural features of peptide candidates modelled using Novafold 12.0 and aligned to NLRP3 structure PDB: 3QF2 using Protean 3D, version 14.0.1.

| Peptide ID | Location in Consensus sequence | Sequence | Secondary Structure |
|---|---|---|---|
| FUS_746_001 | 30-53 | EDYPPQKGCIPL PRGQTEKADHVD (SEQ ID NO: 30) | α-helix |
| FUS_746_002 | 35-53 | QKGCIPLPRGQT EKADHVD (SEQ ID NO: 31) | none |
| FUS_746_003 | 35-49 | QKGCIPLPRGQT EKA (SEQ ID NO: 32) | none |

The modelling and comparison indicates that peptide FUS_746_001 is the preferred candidate for use as a peptide immunogen. In addition to demonstrating the greatest alignment with the model of the parent protein, it also demonstrates high similarity in prediction of secondary structure and is an accessible epitopic target.

Peptide FUS_746_001 Alignment using a Novafold predicted structure is shown in FIG. 17.

Conclusion

The modelling of the software should always be taken as advisory, rather than definitive and interpreted on this basis, particularly if strong secondary structural features are not known to be found within the parent molecule. With this in mind, however, the modelling suggests that peptide FUS_746_001, sequence EDYPPQKGCIPL-PRGQTEKADHVD (SEQ ID NO: 30) would be a best candidate for selection as the immunogen for this project on the basis of alignment to the parent protein, and predicted antigenicity. The peptide also shows only a few points of difference between the mouse and human sequence, which supports the production of an antibody response in mice that may allow for cross reactivity between these species, which is also a desirable feature, whilst minimising cross reactivity to other NLRP types. Note: It is recommended to add an N-terminal Cys residue for cross-linking to KLH.

REFERENCES

Zhang, Y., 2008. I-TASSER server for protein 3D structure prediction. BMC Bioinformatics, 23 January 9(40).
Vajjhala, P. R., Mirams, R. E., and Hill, J. M. (2012). Multiple binding sites on the pyrin domain of ASC protein allow self-association and interaction with NLRP3 protein. J. Biol. Chem. 287, 41732-41743

NLRP3 Antigen Synthesis

The NLRP3 peptide was synthesised by bioSynthesis Inc, Texas, conjugated to KLH using maleimide coupling through an additional C-terminal cysteine residue.

ELISA screening results of 1st bleed from mice immunised with NLRP3 immunogen—see FIG. 18.

Example 5—Generation of a Monoclonal Antibody Against NLRP3

A population of 5 mice were immunised and screened for positive immune responses. After selecting a suitable candidate for fusion, splenocytes were fused with partner cells to produce a population of hybridomas. This population underwent a series of limiting dilutions and screening assays to produce fully monoclonal cell lines.

Cell Line Nomenclature

The product name "F226 7A7-1E1-2D5" refers to one of the 10 chosen monoclonal hybridoma cell lines. The name is comprised of components describing the production pathway at each stage. Each hybridoma selected from the post-fusion screening and each limiting dilution was given a number corresponding to the plate number and well location on that plate for which the hybridoma was chosen (i.e. 7A7-1E1-205). This nomenclature traces the derivation of each individual hybridoma allowing for clear differentiation in the screening process.

Abbreviations

| | |
|---|---|
| Ab | Antibody |
| DMSO | Dimethyl Sulfoxide |
| FCS | Fetal Calf Serum |
| ELISA | Enzyme-Linked Immunosorbent Assay |
| RT | Room Temperature |
| OD | Optical Density |
| PBST | Phosphate-buffered saline + 1% Tween 20 |
| PBS | Phosphate-buffered saline |
| RPM | Revolutions per minute |
| NP, LP, RP, LRP, 2LP | Mouse Identification: No Punch, Left Punch, Right Punch Left/Right Punch, 2 Left Punches |
| HAT | Hypoxanthine, Aminopterin, Thymidine supplement |
| HATR Media[2] | DMEM supplemented with 2% Roche (HFCS), 2% HAT, 1% Pen/Strep, 1% L-Glutamine |
| SFM | Serum Free Medium |
| PEG | Polyethylene Glycol |
| GAM-HRP | Goat Anti-Mouse-Horse Radish Peroxidase |
| HT | Hypoxanthine and Thymidine |
| LD1 | First Limiting Dilution |
| LD2 | Second Limiting Dilution |

[1]This is the media that was used for all cultures following fusion and screening.

Materials
Reagents and Media

| Reagent | Supplier | Catalogue No. |
|---|---|---|
| L-glutamine | Gibco | 25030-024 |
| HAT Supplement | Gibco | 21060-017 |
| HFCS | Roche | 11363735001 |
| DMEM Glutamax | Gibco | 61965-059 |
| Penicillin/Streptomycin | Gibco | 15140-122 |
| FCS | Gibco | 16000.044 |
| DMSO | Sigma | D2650 |
| Trypan Blue | Sigma | T8154 |
| PEG | Sigma | 10783641001 |
| Freund's Adjuvant Complete | Sigma | F5881 |
| Freund's Adjuvant Incomplete | Sigma | F5506 |
| Sodium Hydrogen Carbonate | VWR | 27778.260 |
| Sodium Carbonate | Sigma | S2127-500G |
| Powdered Milk | Marvel | Original Dried Skimmed |
| Tween 20 (10%) | Sigma | P1379-1L |
| GAM-HRP (Fc Specific) | Sigma | A2554 |
| TMB | Biopanda | TMB-S-002 |
| Mr. Frosty | Nalgene | 55710-200 |

Disposables

| Name | Supplier | Catalogue No. |
|---|---|---|
| 25 cm$^2$ static flasks | Corning | 430639 |
| 75 cm$^2$ static flasks | Corning | 430641 |
| 96-well plate sterile | Corning | 3595 |
| 96-well plate sterile TPP | Primer Scientific | 92696T |
| Cryovials | Fisher Scientific | 366656 |
| Maxi Sorb 96- well plates | Nunc | 442404 |

Equipment
  CO$_2$ Cell culture static incubators (SANYO)
  Plate reader Sunrise (Tecan)
  Centurion Scientific K40R Centrifuge
  Grant-Bio Multishaker PSU 20

Methods
Antigen Preparation

Once the immunogen; NLRP3 peptide-KLH conjugate (bioSynthesis Inc, Texas) was received, these solutions were diluted to 400 µg/ml in sterile, EF-PBS and aliquoted in volumes of 600 µl for immunisation and 150 µl for boosts and ELISA screening. These aliquots were labelled and stored at −20° C.

Immunisations

A population of 5 BalbC mice were immunised subcutaneously with 200 μl of a 1:1 emulsion of Freund's Adjuvant Complete (Sigma) and a 600 μl aliquot of NLRP3 peptide-KLH conjugate prepared herein. Two weeks after the $1^{st}$ immunisation, the population was immunized with a $2^{nd}$ injection at the same volumes and concentrations as the original injection only using Freund's Adjuvant Incomplete (Sigma) instead. One week after the $2^{nd}$ immunisation, the mice were tagged by ear punches (NP, RP, LP, LRP, 2LP), and test bleeds were screened as described herein for preliminary results. Three weeks after the $2^{nd}$ immunisation, the population was immunised a $3^{rd}$ time using the same method as the $2^{nd}$ injection. One week after the $3^{rd}$ immunisation test bleeds were screened, and RP was then selected for fusion.

Test Bleed ELISAs

Tail bleeds were taken from the population of 5 BalbC mice and centrifuged at 8000 rpm for 10 min at RT. The blood serum from each mouse was collected, loaded onto the plate the same day as screening, and stored at −20° C. This screening was performed twice for the selection of a suitable mouse for fusion.

The day prior to screening, a Maxi Sorb plate was coated by adding 100 μl/well of 50 mM sodium carbonate coating buffer (pH 9.5) containing the free NLRP3 peptide at 1 μg/ml. A separate coating solution was prepared by diluting APO-A1 in the same coating buffer at 1 μg/ml. These solutions were loaded onto the plate in alternating rows so as to provide two wells to load each sample that demonstrates a positive and negative result. This plate was incubated overnight at 4° C. in static conditions.

The following morning coating buffer was removed, and 200 μl/well of blocking solution (4.0% w/v semi skim milk powder, 1×PBS) was added and agitated at 150 rpm for 2 hr at RT. The plate was washed three times with PBS-T (0.1% v/v Tween 20). PBS was loaded into each well at 100 μl/well, and 1 μl of each test bleed serum was loaded into each positive and negative well. The plate was incubated at 150 rpm (Grant Shaker) for 2 hrs at room temperature. These samples were then removed and washed four times with PBS-T. 100 μl/well GAM-HRP diluted 1:5000 (Sigma, UK) was added, and the plate was incubated for 1 hr with agitation at 150 rpm at RT. The secondary antibody was removed, and the plate was washed four times with PBS-T and once in PBS. 100 μl/well of TMB substrate solution was added and incubated at 37° C. for 10 minutes. 50 μl 1 M HCl was added per well and the plate immediately read at 450 nm on a Tecan Sunrise plate reader.

After the second test bleed ELISA screening, RP was selected for fusion by expressing the most positive immune response.

Boost Injections

One week after the $3^{rd}$ and final immunization, a boost injection was given to BalbC mouse RP by injecting 100 μl of aliquoted IL-1R at 200 μg/ml without any adjuvant.

Fusion F226 One week before fusion, SP2 cells were broken out from liquid nitrogen and were passaged in 10% FCS DMEM supplemented with 1% Pen/Strep, 1% L-glutamine until 3×12 ml T75 flasks were 75%-90% confluent on the day of fusion. On the day of the fusion, SP2 cells were dislodged by tapping the flask and were centrifuged at 1000 rpm for 5 min at 37° C. The cells were resuspended in 20 ml SFM DMEM, centrifuged again, and resuspended in 10 ml SFM DMEM. SP2 cells were stored in a Sterilin tube in SFM at 37° C., 6% $CO_2$ until needed.

After euthanasia, the spleen was aseptically removed from the mouse that showed the strongest immune response. Splenocytes were extracted by puncturing both ends of the spleen with a fine gauge needle and flushing 10-15 ml SFM DMEM. Splenocytes were transferred to a sterilin tube and washed twice with 20 ml serum free DMEM by centrifugation at 1300 rpm for 5 min at 37° C. and gently removing the supernatant. The splenocytes were resuspended in 10 ml Serum free DMEM in a sterilin tube.

Using the SP2 cells stored at 37° C., the SP2 cells were added to the splenocytes. This SP2/splenocytes culture was centrifuged at 1300 rpm for 5 min at 37° C. After discarding the supernatant, 1 ml PEG was added to the SP2/splenocytes culture dropwise while stirring continuously over a period of 3 min. 1 ml SFM DMEM was added to the fusion mixture and stirred for 4 min. 10 ml SFM DMEM was added dropwise to the fresh culture and incubated for in 37° C. water bath for 5 min. The cells were then centrifuged at 1000 rpm for 5 min at 37° C. The pellet was resuspended in 200 mL HATR media and was plated at 200 μl/well in 10×96 well culture plates which were incubated 11 days at 37° C. in 6% $CO_2$ prior to screening.

Post-Fusion Screening and Post-LD Screening

Eleven days after fusion, protoclones were screened by ELISA. 20× Maxi Sorb 96 well plates were coated as described in section 0 using APO-A1 at 1 μg/ml as the negative control for specificity. The coating solution was removed and the plates were blocked as described herein. Samples were prepared by removing 160 μl of supernatant from each well of the ten fusion plates, limiting dilution plates, or 24-well plates and transferring to fresh 96 well culture plates containing 50 μl 1×PBS. After 2 hours of blocking, the blocking solution was removed, and the plates were washed 3× with PBS-T. The samples from each dilution plate were loaded onto the ELISA plates at 100 μl/well by adding 1 row from each dilution plate per 2 rows on the ELISA plates to account for specificity of the coating antigens. Two wells per ELISA were incubated with 100 μl 1×PBS as a negative control. These samples were incubated at 150 rpm for 2 hours at room temperature.

Limiting Dilutions

Once the hybridoma populations were expanded in 24-well plates and growing well, a secondary screen was performed to select the most specific and highest producing populations for rounds of limiting dilutions.

Both limiting dilutions were performed for 1-3 protoclones each by seeding 2-4×96-well plates at 1 cell/well in 200 μl culture/well. The plates were prepared by counting each culture in the 24-well plate and were diluted 10× as an intermediate dilution, then were diluted to 200 cells in 40 ml. The culture was plated at 200 μl/well and left to incubate at 37° C., 6% $CO_2$ for 7-10 days until the wells were 80%-90% confluent. Each well for both limiting dilutions were screened by ELISA as described in section 0.

Final Clone Selection

Following the second limiting dilution, 10 clones were selected for expansion in a 24 well plate. Each clone was left to grow in 37° C., 6% $CO_2$ for 6 days until each well became 80%-90% confluent. When the clones were well established in the 24-well plates, each clone at 1 ml/well was transferred to a T25 flask containing 5 ml fresh 10% HATR DMEM for cryopreservation.

Cryopreservation of Monoclonal Cell Lines

Once the clones were well established (80%-90% confluency) in T25 flasks, each 5 ml culture was centrifuged at 1000 rpm for 5 min at 37° C. and was resuspended in 1 ml of fresh 10% DMEM HATR media. Each 1 ml culture was transferred to a cryovial containing 300 μl of a 1:1 ratio of FCS to DMSO. The vials were sealed and placed in a Mr. Frosty and transferred to the −70° C. freezer for short-term storage.

Cell Preparation for Sequencing

Anti-NLRP3 produced from clone F226 7A7-1E1-2D5 was selected for sequencing. Once the culture was confluent in the T25 flask, the supernatant was discarded. The cells were dislodged by cell scraping into 2 ml fresh media and were centrifuged at 7,600 rpm for 5 min at RT. The supernatant was then discarded and the pellet was flash frozen in liquid nitrogen and placed in −70° C. until ready for mRNA extraction.

Immunisation and Screening of Test Bleeds

A colony of mice were immunised with NLRP3 peptide-KLH conjugate (designed by bioinformatics and synthesised by bioSynthesis Inc, Texas) and regular test bleeds were taken over an 11 week period. Test bleeds were then screened against the antigen.

Upon identification of positive mice, a fusion was performed and supernatant from hybridoma clones were then validated. The specific antibodies then underwent limiting dilution and cloning to produce a stable hybridoma cell line against NLRP3.

The antibodies were screened using ELISA against the target protein—NLRP3—and clones with a signal of at least 3 times the background were selected. Antibodies from 24 clones were selected and further in house testing was performed to pick the best 6 clones.

Results

Test Bleed 1

One week after the $2^{nd}$ immunisation, a tail bleed was taken from each of the 5 mice and screened against unconjugated NLRP3 peptide and APO-A1 for determination of a suitable animal for fusion and a relative specificity of the polyclonal antibody produced—see FIG. 19.

Test Bleed 2

After screening sera from tail bleeds, 2RP was selected for the fusion of its splenocytes to fusion partner SP2 culture as it demonstrated the best immune response—see FIG. 20.

Post-Fusion Screening

Once the wells in each plate had reached 70%-80% confluency, the plates were screened by ELISA against NLRP3 peptide and APO-A1. The hybridoma population producing the highest responses were selected for expansion in a 24-well plate—see FIG. 21.

$1^{st}$ 24-Well Plate Screening

Clones were selected from the post-fusion screening and were arrayed into a 24 well plate for expansion followed by a secondary screening that determines suitable protoclones for the first round of limiting dilutions. 3 clones were selected and limiting dilutions prepared—see FIG. 22.

Limiting Dilution 1 Screening

Once the $1^{st}$ limiting dilution plates were confluent, the limiting dilution was screened by ELISA against NLRP3 Peptide and APO-A1. 31 hybridoma populations were selected from F226 5B7 and 7A7 that demonstrated the highest and most specific response. No clones from 3D4 were suitable—see FIG. 23.

$2^{nd}$ 24-Well Plate Screening

When the clones became confluent in the 24-well plate, each clone was screened by ELISA against NLRP3 peptide and APO-A1. F226 5B7-1E10, 5B7-1G2, 7A7-1C4 and 7A7-1E1 selected for the $2^{nd}$ round of limiting dilution over 2×96 well plates per clone—see FIG. 24.

Limiting Dilution 2 Screening

Once the wells in each plate had reached 70%-80% confluency, the plates were screened by ELISA against NLRP3 peptide and APO-A1. The 24 hybridoma populations producing the highest response and highest specificity were selected for expansion in a 24-well plate and cryopreservation—see FIG. 25.

Dot Blot analysis is shown in FIG. 26. Dot blots were performed using protein lysates from THP-1 macrophages to test supernatant containing the anti NLRP3 monoclonal antibody collected from the best 24 clones from a fusion hybridoma cell line (A25=positive control commercial anti NLRP3 monoclonal antibody (R&D Systems), A26=negative control PBS). Clones 6, 11, 15, 16, 18 and 20 were selected and further tested by Western blotting.

Western Blot Analysis is shown in FIG. 27. Western blots were performed using protein lysates from THP-1 macrophages to test supernatant containing anti-NLRP3 monoclonal antibody collected from the best 6 clones from a fusion hybridoma cell line untreated (lane 1) and stimulated with LPS and ATP (lane 2, (protein ladder lane 3)). Clone 18 was selected for sequencing and was used in the bispecific monoclonal antibody development.

Conclusions

The aim was to produce a range of antibodies against NLRP3 that were functional in preventing assembly of the NLRP3 inflammasome. Once the mice were immunised and screened, 2RP was selected for fusion. 24 monoclonal hybridoma cell lines were produced from two rounds of limiting dilutions. Each population was selected by highest production and highest specificity for NLRP3.

The clone F226 7A7-1E1-2D5 was shown to be most active in preventing NLRP3 assembly in the in vitro assay. These final cell lines have been frozen down, and the antibody expressed by this 7A7-1E1-2D5 will be sequenced for the next stage in the production of the bi-specific, InflaMab.

Example 6—NLRP3 Monoclonal Sequencing mRNA was extracted from the hybridoma cell pellets on 23/02/16. Total RNA was extracted from the pellets using Fusion Antibodies Ltd in-house RNA extraction protocol (see Example 3).

RT-PCR cDNA was created from the RNA by reverse-transcription with an oligo(dT) primer. PCR reactions are set up using variable domain primers to amplify both the VH and VL regions of the monoclonal antibody DNA giving the following bands (see FIG. 28):

The VH and VL products were cloned into the Invitrogen sequencing vector pCR2.1 and transformed into TOP10 cells and screened by PCR for positive transformants. Selected colonies were picked and analyzed by DNA sequencing on an ABI3130xI Genetic Analyzer, the result may be seen below.

Sequencing Results

```
                            Heavy Chain
                   V_H Amino Acid Sequence Alignment:

1                                                50
VH1.1       (1)    MNFGLSLVFLVLVLKGAQCEVQLVESGGGLVKPGGSLKLSCAASGFTFSD
VH3.7       (1)    -------FLVLVLKGVQCEVQLVESGGGLVKPGGSLKLSCAASGFTFSD
VH3.4       (1)    MDFGLSRVFLVLVLKGVQCEVQLVESGGGLVKPGGSLKLSCAASGFTFSD
VH3.1       (1)    MDFGLSWVFLVLVLKGVQCEVQLVESGGGLVKPGGSLKLSCAASGFTFSD
VH3.5       (1)    MDFGLSWVFLVLVLKGVQCEVQLVESGGGLVKPGGSLKLSCAASGFTFSD
VH3.8       (1)    MDFGLSWVFLVLVLKGVQCEVQLVESGGGLVKPGGSLKLSCAASGFTFSD
Consensus   (1)    MDFGLSRVFLVLVLKGVQCEVQLVESGGGLVKPGGSLKLSCAASGFTFSD 51                                               100
VH1.1       (51)   YYMYWVRQTPEKRLEWVATISDGGTYTYYPDSVKGRFTISRDNAKNNLYL
VH3.7       (51)   YYMYWVRQTPEKRLEWVATISDGGTYTYYPDSVKGRFTISRDNAKNNLYL
VH3.4       (51)   YYMYWVRQTPEKRLEWVATISDGGTYTYYPDSVKGRFTISRDNAKNNLYL
VH3.1       (51)   YYMYWVRQTPEKRLEWVATISDGGTYTYYPDSVKGRFTISRDNAKNNLYL
VH3.5       (51)   YYMYWVRQTPEKRLEWVATISDGGTYTYYPDSVKGRFTISRDNAKNNLYL
VH3.8       (51)   YYMYWVRQTPEKRLEWVATISDGGTYTYYPDSVKGRFTISRDNAKNNLYL
Consensus   (51)   YYMYWVRQTPEKRLEWVATISDGGTYTYYPDSVKGRFTISRDNAKNNLYL 101                                              150
VH1.1       (101)  QMNSLK--------------------------------------------
VH3.7       (101)  QMNSLKSEDTAMYYCARGWVSTMVKLLSSFPYWGQGTLVTVSAAKTTPPS
VH3.4       (101)  QMNSLKSEDTAMYYCARGWVSTMVKLLSSFPYWGQGTLVTVSAAKTTPPS
VH3.1       (101)  QMNSLKSEDTAMYYCARGWVSTMVKLLSSFPYWGQGTLVTVSAAKTTPPS
VH3.5       (101)  QMNSLKSEDTAMYYCARGWVSTMVKLLSSFPYWGQGTLVTVSAAKTTPPS
VH3.8       (101)  QMNSLKSEDTAMYYCARGWVSTMVKLLSSFPYWGQGTLVTVSAAKTTPPS
Consensus   (101)  QMNSLKSEDTAMYYCARGWVSTMVKLLSSFPYWGQGTLVTVSAAKTTPPS 151
VH1.1       (151)  -----
VH3.7       (151)  VYPLA
VH3.4       (151)  VYPLA
VH3.1       (151)  VYPLA
VH3.5       (151)  VYPLA
VH3.8       (151)  VYPLA
Consensus   (151)  VYPLA VH1.1       (SEQ ID NO: 33)
VH3.7       (SEQ ID NO: 34)
VH3.4       (SEQ ID NO: 35)
VH3.1       (SEQ ID NO: 36)
VH3.5       (SEQ ID NO: 36)
VH3.8       (SEQ ID NO: 36)
Consensus   (SEQ ID NO: 36)
```

Key to amino acid shading:
Black         non-similar residues
Bold          consensus residue derived from a block of residues at a given position
Underlined    residues similar in structure to consensus residue or each other when no consensus found
Italicised    consensus residue derived from a completely conserved residue at a given position
Underlined/italicized    residue weakly similar to consensus residue at given position $V_H$ Consensus Amino Acid Sequence:

(SEQ ID NO: 35)

MDFGLSWVFLVLVLKGVQCEVQLVESGGGLVKPGGSLKLSCAASGFTFSD

YYMYWVRQTPEKRLEWVATISDGGTYTYYPDSVKGRFTISRDNAKNNLYL

QMNSLKSEDTAMYYCARGWVSTMVKLLSSFPYWGQGTLVTVSAAKTTPPS

VYPLA

The variable domain is highlighted in BOLD.

The Complementarity Determining Regions (CDRs) are underlined as determined by the IMGT numbering system (Lefranc, M.-P. et al., Nucleic Acids Research, 27, 209-212 (1999))—see FIG. 29.

Key to Amino Acid Shading, in FIG. 29:
Blue shaded circles are hydrophobic (non-polar) residues in frameworks 1-3 at sites that are hydrophobic in the majority of antibodies.
Yellow shaded circles are proline residues.
Squares are key residues at the start and end of the CDR.
Red amino acids in the framework are structurally conserved amino acids.

```
                        Light Chain
             V_L Amino Acid Sequence Alignment:

1                                                 50
VL1.1       (1)  MAWISLIFSLLALSSGAISQAVVTQESALTTSPGETVTLTCRSSTGAVTT
VL1.6       (1)  MAWISLIFSLLALSSGAISQAVVTQESALTTSPGETVTLTCRSSTGAVTT
VL1.2       (1)  MAWTSLLLSLLALSSGAISQAVVTQESALTTSPGETVTLTCRSSTGAVTT
VL1.7       (1)  MAWTSLLFSLLALSSGAISQAVVTQESALTTSPGETVTLTCRSSTGAVTT
VL1.4       (1)  MAWIPLLFSLLALSSGAISQAVVTQESALTTSPGETVTLTCRSSTGAVTT
VL1.5       (1)  MAWISLLLSLLALSSGAISQAVVTQESALTTSPGETVTLTCRSSTGAVTT
Consensus   (1)  MAWISLLFSLLALSSGAISQAVVTQESALTTSPGETVTLTCRSSTGAVTT 51                                                100
VL1.1      (51)  SNYANWVQEKPDHLFTGLVGGTNNRAPGVPARFSGSLIGDKAALTITGAQ
VL1.6      (51)  SNYANWVQEKPDHLFTGLIGGTSNRAPGVPARFSGSLIGDKAALTITGAQ
VL1.2      (51)  SNYANWVQEKPDHLFTGLIGGTNNRAPGVPARFSGSLIGDKAALTITGAQ
VL1.7      (51)  SNYANWVQEKPDHLFTGLIGGTNNRAPGVPARFSGSLIGDKAALTITGAQ
VL1.4      (51)  SNYANWVQEKPDHLFTGLIGGTNNRAPGVPARFSGSLIGDKAALTITGAQ
VL1.5      (51)  SNYANWVQEKPDHLFTGLIGGTNNRAPGVPARFSGSLIGDKAALTITGAQ
Consensus  (51)  SNYANWVQEKPDHLFTGLIGGTNNRAPGVPARFSGSLIGDKAALTITGAQ 101                                               150
VL1.1     (101)  TEDEAIYFCALWYSNYWVFGGGTKLTVLGQPKSSPSVTLFPPSTEELSL
VL1.6     (101)  TEDEAIYFCALWYSNYWVFGGGTKLTVLGQPKSSPSVTLYPPSTKELSL
VL1.2     (101)  TEDEAIYFCALWYSNYWVFGGGTKLTVLGQPKSSPSVTLCPPSSEKLSL
VL1.7     (101)  TEDEAIYFCALWYSNYWVFGGGTKLTVLGQPKSSPSVTLCPPSTEKLSL
VL1.4     (101)  TEDEAIYFCALWYSNYWVFGGGTKLTVLGQPKSSPSVTLFPPSLEKLSL
VL1.5     (101)  TEDEAIYFCALWYSNYWVFGGGTKLTVLGQPKSSPSVTLFPPSTEELSL
Consensus (101)  TEDEAIYFCALWYSNYWVFGGGTKLTVLGQPKSSPSVTLFPPSTEKLSL VL1.1      (SEQ ID NO: 37)
VL1.6      (SEQ ID NO: 38)
VL1.2      (SEQ ID NO: 39)
VL1.7      (SEQ ID NO: 40)
VL1.4      (SEQ ID NO: 41)
VL1.5      (SEQ ID NO: 42)
Consensus  (SEQ ID NO: 43)
```

Key to amino acid shading:
Black       non-similar residues
Bold        consensus residue derived from a block of residues at
            a given position
Underlined  residues similar in structure to consensus residue or
            each other when no consensus found
Italicised  consensus residue derived from a completely conserved
            residue at a given position
Underlined/ residue weakly similar to consensus residue at given
italicized  position $V_L$ Consensus Amino Acid Sequence:

$V_L$ Consensus Amino Acid Sequence:
(SEQ ID NO: 43)

MAWISLLLSLLALSSGAISQAVVTQESALTTSPGETVTLTCRSSTGAVTT

SNYANWVQEKPDHLFTGLIGGTNNRAPGVPARFSGSLIGDKAALTITGAQ

TEDEAIYFCALWYSNYWVFGGGTKLTVLGQPKSSPSVTLFPPSTEELSL

The variable domain is highlighted in BOLD.

The Complementarity Determining Regions (CDRs) are underlined as determined by the IMGT numbering system (Lefranc, M.-P. et al., Nucleic Acids Research, 27, 209-212 (1999))—see FIG. 30.

Key to Amino Acid Shading, in FIG. 30:

Blue shaded circles are hydrophobic (non-polar) residues in frameworks 1-3 at sites that are hydrophobic in the majority of antibodies.

Yellow shaded circles are proline residues.

Squares are key residues at the start and end of the CDR.

Red amino acids in the framework are structurally conserved amino acids.

VH Sequencing results:
VH1.1 DNA Sequence:
(SEQ ID NO: 44)

ATGAACTTCGGGTTGAGCTTGGTTTTCCTTGTCCTTGTTTTAAAAGGTGCCCAGTGTGAAGTGCA

GCTGGTGGAGTCTGGGGGAGGCTTAGTGAAGCCTGGAGGGTCCCTGAAACTCTCCTGTGCAGC

CTCTGGATTCACTTTCAGTGACTATTACATGTATTGGGTTCGCCAGACTCCGGAAAAGAGGCTG

GAGTGGGTCGCAACCATTAGTGATGGTGGTACTTACACCTACTATCCAGACAGTGTGAAGGGGC

GATTCACCATCTCCAGAGACAATGCCAAGAACAACCTTTACCTGCAAATGAACAGTCTGAAG

-continued

VH1.1 Amino Acid Sequence:
(SEQ ID NO: 33)
MNFGLSLVFLVLVLKGAQCEVQLVESGGGLVKPGGSLKLSCAASGFTFSDYYMYWVRQTPEKRLE

WVATISDGGTYTYYPDSVKGRFTISRDNAKNNLYLQMNSLK

VH3.1 DNA Sequence:
(SEQ ID NO: 45)
ATGGACTTCGGGTTGAGCTGGGTTTTCCTTGTCCTTGTTTTAAAAGGTGTCCAGTGTGAAGTGCA

GCTGGTGGAGTCTGGGGGAGGCTTAGTGAAGCCTGGAGGGTCCCTGAAACTCTCCTGTGCAGC

CTCTGGATTCACTTTCAGTGACTATTACATGTATTGGGTTCGCCAGACTCCGGAAAAGAGGCTG

GAGTGGGTCGCAACCATTAGTGATGGTGGTACTTACACCTACTATCCAGACAGTGTGAAGGGGC

GATTCACCATCTCCAGAGACAATGCCAAGAACAACCTTTACCTGCAAATGAACAGTCTGAAGTCT

GAGGACACAGCCATGTATTACTGTGCAAGAGGATGGGTTTCTACTATGGTTAAACTTCTTTCCTC

CTTTCCTTACTGGGGCCAAGGGACTCTGGTCACTGTCTCTGCAGCCAAAACGACACCCCCATCT

GTCTATCCACTGGCC

VH3.1 Amino Acid Sequence:
(SEQ ID NO: 36)
MDFGLSWVFLVLVLKGVQCEVQLVESGGGLVKPGGSLKLSCAASGFTFSDYYMYWVRQTPEKRLE

WVATISDGGTYTYYPDSVKGRFTISRDNAKNNLYLQMNSLKSEDTAMYYCARGWVSTMVKLLSSFP

YWGQGTLVTVSAAKTTPPSVYPLA

VH3.4 DNA Sequence:
(SEQ ID NO: 46)
ATGGACTTCGGGCTGAGCAGGGTTTTCCTTGTCCTTGTTTTAAAAGGTGTCCAGTGTGAAGTGC

AGCTGGTGGAGTCTGGGGGAGGCTTAGTGAAGCCTGGAGGGTCCCTGAAACTCTCCTGTGCAG

CCTCTGGATTCACTTTCAGTGACTATTACATGTATTGGGTTCGCCAGACTCCGGAAAAGAGGCT

GGAGTGGGTCGCAACCATTAGTGATGGTGGTACTTACACCTACTATCCAGACAGTGTGAAGGG

GCGATTCACCATCTCCAGAGACAATGCCAAGAACAACCTTTACCTGCAAATGAACAGTCTGAAG

TCTGAGGACACAGCCATGTATTACTGTGCAAGAGGATGGGTTTCTACTATGGTTAAACTTCTTTC

CTCCTTTCCTTACTGGGGCCAAGGGACTCTGGTCACTGTCTCTGCAGCCAAAACGACACCCCA

TCTGTCTATCCACTGGCC

VH3.4 Amino Acid Sequence:
(SEQ ID NO: 35)
MDFGLSRVFLVLVLKGVQCEVQLVESGGGLVKPGGSLKLSCAASGFTFSDYYMYWVRQTPEKRLE

WVATISDGGTYTYYPDSVKGRFTISRDNAKNNLYLQMNSLKSEDTAMYYCARGWVSTMVKLLSSFP

YWGQGTLVTVSAAKTTPPSVYPLA

VH3.5 DNA Sequence:
(SEQ ID NO: 47)
ATGGACTTCGGGCTGAGCTGGGTTTTCCTTGTCCTTGTTTTAAAAGGTGTCCAGTGTGAAGTGC

AGCTGGTGGAGTCTGGGGGAGGCTTAGTGAAGCCTGGAGGGTCCCTGAAACTCTCCTGTGCAG

CCTCTGGATTCACTTTCAGTGACTATTACATGTATTGGGTTCGCCAGACTCCGGAAAAGAGGCT

GGAGTGGGTCGCAACCATTAGTGATGGTGGTACTTACACCTACTATCCAGACAGTGTGAAGGG

GCGATTCACCATCTCCAGAGACAATGCCAAGAACAACCTTTACCTGCAAATGAACAGTCTGAAG

TCTGAGGACACAGCCATGTATTACTGTGCAAGAGGATGGGTTTCTACTATGGTTAAACTTCTTTC

CTCCTTTCCTTACTGGGGCCAAGGGACTCTGGTCACTGTCTCTGCAGCCAAAACGACACCCCA

TCTGTCTATCCACTGGCC

```
VH3.5 Amino Acid Sequence:
                                                        (SEQ ID NO: 36)
MDFGLSWVFLVLVLKGVQCEVQLVESGGGLVKPGGSLKLSCAASGFTFSDYYMYWVRQTPEKRLE

WVATISDGGTYTYYPDSVKGRFTISRDNAKNNLYLQMNSLKSEDTAMYYCARGWVSTMVKLLSSFP

YWGQGTLVTVSAAKTTPPSVYPLA

VH3.7 DNA Sequence:
                                                        (SEQ ID NO: 48)
TTTTCCTTGTCCTTGTTTTAAAAGGTGTCCAGTGTGAAGTGCAGCTGGTGGAGTCTGGGGGAGG

CTTAGTGAAGCCTGGAGGGTCCCTGAAACTCTCCTGTGCAGCCTCTGGATTCACTTTCAGTGAC

TATTACATGTATTGGGTTCGCCAGACTCCGGAAAAGAGGCTGGAGTGGGTCGCAACCATTAGTG

ATGGTGGTACTTACACCTACTATCCAGACAGTGTGAAGGGGCGATTCACCATCTCCAGAGACAA

TGCCAAGAACAACCTTTACCTGCAAATGAACAGTCTGAAGTCTGAGGACACAGCCATGTATTACT

GTGCAAGAGGATGGGTTTCTACTATGGTTAAACTTCTTTCCTCCTTTCCTTACTGGGGCCAAGGG

ACTCTGGTCACTGTCTCTGCAGCCAAAACGACACCCCCATCTGTCTATCCACTGGCC

VH3.7 Amino Acid Sequence:
                                                        (SEQ ID NO: 33)
FLVLVLKGVQCEVQLVESGGGLVKPGGSLKLSCAASGFTFSDYYMYWVRQTPEKRLEWVATISDGG

TYTYYPDSVKGRFTISRDNAKNNLYLQMNSLKSEDTAMYYCARGWVSTMVKLLSSFPYWGQGTLVT

VSAAKTTPPSVYPLA

VH3.8 DNA Sequence:
                                                        (SEQ ID NO: 49)
ATGGACTTCGGGCTGAGCTGGGTTTTCCTTGTCCTTGTTTTAAAAGGTGTCCAGTGTGAAGTGC

AGCTGGTGGAGTCTGGGGGAGGCTTAGTGAAGCCTGGAGGGTCCCTGAAACTCTCCTGTGCAG

CCTCTGGATTCACTTTCAGTGACTATTACATGTATTGGGTTCGCCAGACTCCGGAAAAGAGGCT

GGAGTGGGTCGCAACCATTAGTGATGGTGGTACTTACACCTACTATCCAGACAGTGTGAAGGG

GCGATTCACCATCTCCAGAGACAATGCCAAGAACAACCTTTACCTGCAAATGAACAGTCTGAAG

TCTGAGGACACAGCCATGTATTACTGTGCAAGAGGATGGGTTTCTACTATGGTTAAACTTCTTTC

CTCCTTTCCTTACTGGGGCCAAGGGACTCTGGTCACTGTCTCTGCAGCCAAAACGACACCCCCA

TCTGTCTATCCACTGGCC

VH3.8 Amino Acid Sequence:
                                                        (SEQ ID NO: 36)
MDFGLSWVFLVLVLKGVQCEVQLVESGGGLVKPGGSLKLSCAASGFTFSDYYMYWVRQTPEKRLE

WVATISDGGTYTYYPDSVKGRFTISRDNAKNNLYLQMNSLKSEDTAMYYCARGWVSTMVKLLSSFP

YWGQGTLVTVSAAKTTPPSVYPLA

VL Sequencing Results:
VL1.1 DNA Sequence:
                                                        (SEQ ID NO: 50)
ATGGCCTGGATTTCTCTTATATTCTCTCTCCTGGCTCTCAGCTCAGGGGCCATTTCCCAGGCTGT

TGTGACTCAGGAATCTGCACTCACCACATCACCTGGTGAAACAGTCACACTCACTTGTCGCTCA

AGTACTGGGGCTGTTACAACTAGTAACTATGCCAACTGGGTCCAAGAAAAACCAGATCATTTATT

CACTGGTCTAGTAGGTGGTACCAACAACCGAGCTCCAGGTGTTCCTGCCAGATTCTCAGGCTCC

CTGATTGGAGACAAGGCTGCCCTCACCATCACAGGGGCACAGACTGAGGATGAGGCAATATAT

TTCTGTGCTCTATGGTACAGCAATTATTGGGTGTTCGGTGGAGGAACCAAACTGACTGTCCTAG

GCCAGCCCAAGTCTTCGCCATCAGTCACCCTGTTCCCACCCTCCACTGAAGAGCTAAGCTTGGG
```

```
VL1.1 Amino Acid Sequence:
                                                       (SEQ ID NO: 37)
MAWISLIFSLLALSSGAISQAVVTQESALTTSPGETVTLTCRSSTGAVTTSNYANWVQEKPDHLFTGL

VGGTNNRAPGVPARFSGSLIGDKAALTITGAQTEDEAIYFCALWYSNYWVFGGGTKLTVLGQPKSSP

SVTLFPPSTEELSL

VL1.2 DNA Sequence:
                                                       (SEQ ID NO: 51)
ATGGCCTGGACTTCACTCTTACTCTCTCCTGGCTCTCAGCTCAGGGGCCATTTCCCAGGCTG

TTGTGACTCAGGAATCTGCACTCACCACATCACCTGGTGAAACAGTCACACTCACTTGTCGCTC

AAGTACTGGGGCTGTTACAACTAGTAACTATGCCAACTGGGTCCAAGAAAAACCAGATCATTTAT

TCACTGGTCTAATAGGTGGTACCAACAACCGAGCTCCAGGTGTTCCTGCCAGATTCTCAGGCTC

CCTGATTGGAGACAAGGCTGCCCTCACCATCACAGGGGCACAGACTGAGGATGAGGCAATATA

TTTCTGTGCTCTATGGTACAGCAATTATTGGGTGTTCGGTGGAGGAACCAAACTGACTGTCCTA

GGCCAGCCCAAGTCTTCGCCATCAGTCACCCTGTGCCCGCCCTCCTCAGAGAAGCTAAGCTTGGG

VL1.2 Amino Acid Sequence:
                                                       (SEQ ID NO: 39)
MAWTSLLLSLLALSSGAISQAVVTQESALTTSPGETVTLTCRSSTGAVTTSNYANWVQEKPDHLFTG

LIGGTNNRAPGVPARFSGSLIGDKAALTITGAQTEDEAIYFCALWYSNYWVFGGGTKLTVLGQPKSS

PSVTLCPPSSEKLSL

VL1.4 DNA Sequence:
                                                       (SEQ ID NO: 52)
ATGGCCTGGATTCCTCTTTTATTCTCTCTCCTGGCTCTCAGCTCAGGGGCCATTTCCCAGGCTGT

TGTGACTCAGGAATCTGCACTCACCACATCACCTGGTGAAACAGTCACACTCACTTGTCGCTCA

AGTACTGGGGCTGTTACAACTAGTAACTATGCCAACTGGGTCCAAGAAAAACCAGATCATTTATT

CACTGGTCTAATAGGTGGTACCAACAACCGAGCTCCAGGTGTTCCTGCCAGATTCTCAGGCTCC

CTGATTGGAGACAAGGCTGCCCTCACCATCATAGGGGCACAGACTGAGGATGAGGCAATATATT

TCTGTGCTCTATGGTACAGCAATTATTGGGTGTTCGGTGGAGGAACCAAACTGACTGTCCTAGG

CCAGCCCAAGTCTTCGCCATCAGTCACCCTGTTCCCGCCCTCCTTAGAAAAGCTTAGCTTGGG

VL1.4 Amino Acid Sequence:
                                                       (SEQ ID NO: 41)
MAWIPLLFSLLALSSGAISQAVVTQESALTTSPGETVTLTCRSSTGAVTTSNYANWVQEKPDHLFTGL

IGGTNNRAPGVPARFSGSLIGDKAALTIIGAQTEDEAIYFCALWYSNYWVFGGGTKLTVLGQPKSSPS

VTLFPPSLEKLSL

VL1.5 DNA Sequence:
                                                       (SEQ ID NO: 53)
ATGGCCTGGATTTCACTTTTACTCTCTCTCCTGGCTCTCAGCTCAGGGGCCATTTCCCAGGCTG

TTGTGACTCAGGAATCTGCACTCACCACATCACCTGGTGAAACAGTCACACTCACTTGTCGCTC

AAGTACTGGGGCTGTTACAACTAGTAACTATGCCAACTGGGTCCAAGAAAAACCAGATCATTTAT

TCACTGGTCTAATAGGTGGTACCAACAACCGAGCTCCAGGTGTTCCTGCCAGATTCTCAGGCTC

CCTGATTGGAGACAAGGCTGCCCTCACCATCACAGGGGCACAGACTGAGGATGAGGCAATATA

TTTCTGTGCTCTATGGTACAGCAATTATTGGGTGTTCGGTGGAGGAACCAAACTGACTGTCCTA

GGCCAGCCCAAGTCTTCGCCATCAGTCACCCTGTTTCCACCCTCCACAGAAGAGCTAAGCTTGGG

VL1.5 Amino Acid Sequence:
                                                       (SEQ ID NO: 42)
MAWISLLLSLLALSSGAISQAVVTQESALTTSPGETVTLTCRSSTGAVTTSNYANWVQEKPDHLFTGL

IGGTNNRAPGVPARFSGSLIGDKAALTITGAQTEDEAIYFCALWYSNYWVFGGGTKLTVLGQPKSSP

SVTLFPPSTEELSL
```

VL1.6 DNA Sequence:
(SEQ ID NO: 54)
ATGGCCTGGATTTCACTTATCTTCTCTCTCCTGGCTCTCAGCTCAGGGGCCATTTCCCAGGCTG

TTGTGACTCAGGAATCTGCACTCACCACATCACCTGGTGAAACAGTCACACTCACTTGTCGCTC

AAGTACTGGGGCTGTTACAACTAGTAACTATGCCAACTGGGTCCAAGAAAAACCAGATCATTTAT

TCACTGGTCTAATAGGTGGTACCAGCAACCGAGCTCCAGGTGTTCCTGCCAGATTCTCAGGCTC

CCTGATTGGAGACAAGGCTGCCCTCACCATCACAGGGGCACAGACTGAGGATGAGGCAATATA

TTTCTGTGCTCTATGGTACAGCAATTATTGGGTGTTCGGTGGAGGAACCAAACTGACTGTCCTA

GGCCAGCCCAAGTCTTCGCCATCAGTCACCCTGTACCCGCCCTCTACAAAGGAGCTTAGCTTG

GG

VL1.6 Amino Acid Sequence:
(SEQ ID NO: 38)
MAWISLIFSLLALSSGAISQAVVTQESALTTSPGETVTLTCRSSTGAVTTSNYANWVQEKPDHLFTGLI

GGTSNRAPGVPARFSGSLIGDKAALTITGAQTEDEAIYFCALWYSNYWVFGGGTKLTVLGQPKSSPS

VTLYPPSTKELSL

VL1.7 DNA Sequence:
(SEQ ID NO: 55)
ATGGCCTGGACTTCTCTCTTATTCTCTCTCCTGGCTCTCAGCTCAGGGGCCATTTCCCAGGCTG

TTGTGACTCAGGAATCTGCACTCACCACATCACCTGGTGAAACAGTCACACTCACTTGTCGCTC

AAGTACTGGGGCTGTTACAACTAGTAACTATGCCAACTGGGTCCAAGAAAAACCAGATCATTTAT

TCACTGGTCTAATAGGTGGTACCAACAACCGAGCTCCAGGTGCTCCTGCCAGATTCTCAGGCTC

CCTGATTGGAGACAAGGCTGCCCTCACCATCACAGGGGCACAGACTGAGGATGAGGCAATATA

TTTCTGTGCTCTATGGTACAGCAATTATTGGGTGTTCGGTGGAGGAACCAAACTGACTGTCCTA

GGCCAGCCCAAGTCTTCGCCATCAGTCACCCTGTGCCCGCCCTCTACAGAAAAGCTAAGCTTG

GG

VL1.7 Amino Acid Sequence:
(SEQ ID NO: 40)
MAWTSLLFSLLALSSGAISQAVVTQESALTTSPGETVTLTCRSSTGAVTTSNYANWVQEKPDHLFTG

LIGGTNNRAPGAPARFSGSLIGDKAALTITGAQTEDEAIYFCALWYSNYWVFGGGTKLTVLGQPKSS

PSVTLCPPSTEKLSL

Example 7—InflaMab Design—Development of a Bi-Specific Antibody Against Both of IL-1R1 and NLRP3

The variable domain sequences of the monoclonal antibodies IL-1 R1 and NLRP3 were sequenced.

The antibody was constructed using the IL-1 R1 antibody with an IgG2a mouse constant domain sequence. A short linker was added to the C-terminal end of the heavy chain and the NLPR3 variable domains in an ScFv format with the linker (GGGGS)₃ was attached to create the bispecific.

The DNA and amino acid sequences can be found below.

The constructs were cloned into ATUM vector pD2610-v5 and verified by sequencing. FIG. 31 illustrates the bispecific design and the plasmid map of InflaMab.

Designed Bispecific Antibody Sequences

Light Chain DNA Sequence:
(SEQ ID NO: 56)
ATGGTCAGCTCTGCTCAATTTCTCGGACTCCTTCTTCTGTGCTTTCAAGGAACACGCTGCGATAT

TGTGATGACCCAGTCCCCCGCCACCCTGTCCGTGACTCCGGGCGACCGGGTGTCCCTGTCGTG

CCGGGCATCACAGAGCATCTCCGACTACCTGTCGTGGTACCAGCAGAGATCACACGAGAGCCC

TCGCCTGATCATCAAATACGCCAGCCAGTCAATCTCCGGCATCCCCTCGCGGTTCTCCGGGTCC

GGTTCCGGCTCCGACTTCACACTGTCCATTAACTCCGTGGAACCTGAGGACGTGGGAGTGTACT

ACTGTCAACACGGCCATTCGTTCCCGCTGACTTTCGGGTCGGGAACCAAGCTGGAATTGAAGA

GGGCGGACGCGGCCCCTACCGTGTCAATTTTCCCACCGAGCTCCGAACAGCTCACCAGCGGC

-continued

```
GGTGCCTCGGTCGTGTGCTTCCTCAACAACTTCTATCCAAAAGACATTAACGTCAAGTGGAAGA

TCGATGGATCGGAGAGACAGAACGGAGTGCTGAACAGCTGGACTGATCAGGACTCCAAGGATT

CGACCTACTCCATGAGCTCCACTCTGACCCTGACCAAGGACGAATACGAGCGGCACAATTCCTA

CACTTGCGAAGCCACCCACAAGACCTCAACGTCCCCCATCGTGAAGTCCTTCAACCGCAACGA

GTGTTGATAA
```

Light Chain Amino Acid Sequence:
(SEQ ID NO: 57)
```
MVSSAQFLGLLLLCFQGTRCDIVMTQSPATLSVTPGDRVSLSCRASQSISDYLSWYQQRSHESPRLII

KYASQSISGIPSRFSGSGSGSDFTLSINSVEPEDVGVYYCQHGHSFPLTFGSGTKLELKRADAAPTV

SIFPPSSEQLTSGGASVVCFLNNFYPKDINVKWKIDGSERQNGVLNSWTDQDSKDSTYSMSSTLTLT

KDEYERHNSYTCEATHKTSTSPIVKSFNRNEC**
```

Heavy Chain DNA Sequence:
(SEQ ID NO: 58)
```
ATGGGCTGGACCCTCGTGTTCCTGTTCCTGCTGAGCGTGACGGCGGGCGTGCACTCCCAAATC

CAGCTTGTGCAGTCCGGACCCGAGCTCAGGAAGCCGGGCGAAACTGTGCGCATCAGCTGCAA

GGCTTCAGGGTACCCTTTCACCACCGCCGGGCTGCAATGGGTGCAGAAGATGTCCGGGAAGG

GTCTGAAGTGGATCGGATGGATGAACACCCAGTCCGAAGTGCCTAAATACGCCGAAGAATTCAA

GGGCCGCATTGCGTTCAGCCTGGAGACAGCCGCCTCGACCGCGTACCTTCAGATCAACAATCT

CAAGACTGAGGACACTGCCACCTACTTCTGTGCCAAGAGCGTGTACTTCAACTGGAGATACTTC

GACGTGTGGGGCGCCGGAACCACCGTGACCGTGTCCAGCGCCAAGACTACCGCCCCGAGCGT

GTACCCTCTGGCGCCAGTGTGCGGCGACACGACTGGCAGCTCGGTGACCTTGGGCTGCCTCG

TGAAGGGTTACTTCCCCGAGCCCGTGACTCTGACTTGGAACTCGGGCTCACTGTCGTCCGGAG

TGCATACCTTCCCGGCTGTGCTGCAAAGCGACCTCTATACCTTGTCATCGTCCGTGACTGTGAC

CTCCTCCACCTGGCCGTCCCAGACATCACCTGTAATGTCGCCCACCCTGCTTCATCGACTAAG

GTCGACAAGAAGATCGAGCCCAGAGGACCTACCATCAAGCCCTGCCCGCCCTGCAAATGCCCG

GCCCCAAACTTGCTGGGAGGGCCTTCCGTGTTCATCTTCCCTCCGAAAATCAAGGACGTGCTGA

TGATCTCCCTGAGCCCAATTGTCACTTGCGTGGTGGTGGATGTGTCCGAAGATGACCCAGATGT

GCAGATTTCATGGTTCGTGAACAACGTCGAAGTCCATACCGCACAGACCCAGACCCACCGCGA

GGATTACAACTCGACGCTGCGCGTCGTCAGCGCCCTGCCGATTCAGCACCAGGATTGGATGAG

CGGAAAGGAATTCAAGTGCAAAGTCAACAACAAGGACCTTCCGGCGCCGATCGAACGGACCAT

CTCGAAGCCTAAGGGATCAGTGCGGGCGCCTCAGGTCTACGTGCTCCCGCCTCCGGAAGAGG

AAATGACCAAGAAACAAGTCACCCTGACTTGCATGGTCACCGACTTCATGCCTGAGGACATCTA

TGTGGAGTGGACTAACAACGGAAAGACTGAACTGAACTACAAAAACACCGAACCAGTGCTGGAC

TCTGACGGCTCCTACTTCATGTACTCGAAGCTGCGGGTGGAGAAGAAAAACTGGGTGGAACGA

AACTCCTACTCGTGTTCCGTGGTGCACGAGGGTCTGCACAACCACCATACCACCAAGTCCTTCT

CCCGGACCCCCGGAAAGGGATCCGCCGGGGGATCCGGAGGGGACTCCGAAGTGCAACTGGT

GGAGTCGGGTGGCGGACTCGTGAAGCCCGGGGGGTCATTGAAGCTTTCCTGTGCTGCCTCCG

GTTTCACTTTCTCCGACTATTACATGTACTGGGTCAGACAGACCCCCGGAGAAGCGGCTCGAATG

GGTGGCCACCATTTCGGACGGTGGAACCTACACTTACTACCCTGACTCCGTCAAGGGCCGGTT

TACTATCTCCCGCGACAACGCGAAGAACAATCTGTACCTCCAAATGAACTCCCTGAAGTCCGAG

GACACCGCCATGTACTATTGCGCAAGGGGATGGGTCAGCACTATGGTCAAGCTGCTGTCATCCT

TCCCTTACTGGGGACAGGGAACCCTTGTGACTGTGTCAGCCGGTGGCGGGGGTCGGCGGC

GGCGGTTCCGGTGGAGGGGGATCCCAGGCCGTCGTGACCCAAGAGTCGGCTCTGACTACTTC
```

```
ACCCGGAGAAACCGTGACCCTGACATGCCGCTCCTCCACTGGCGCAGTGACCACGAGCAATTA

CGCCAACTGGGTGCAGGAAAAGCCCGATCACCTGTTCACTGGACTCATTGGGGGAACCAACAA

CCGGGCGCCGGGCGTGCCCGCTCGGTTTAGCGGCTCCCTGATTGGAGACAAGGCCGCCCTGA

CTATCACCGGAGCCCAGACCGAAGATGAAGCCATCTACTTTTGCGCACTCTGGTACTCTAACTA

CTGGGTGTTTGGCGGCGGAACCAAGCTGACTGTGCTCGGACAGCCGAAGTGATAAAA

Heavy Chain Amino Acid Sequence:
                                                    (SEQ ID NO: 59)
MGWTLVFLFLLSVTAGVHSQIQLVQSGPELRKPGETVRISCKASGYPFTTAGLQWVQKMSGKGLKW

IGWMNTQSEVPKYAEEFKGRIAFSLETAASTAYLQINNLKTEDTATYFCAKSVYFNWRYFDVWGAGT

TVTVSSAKTTAPSVYPLAPVCGDTTGSSVTLGCLVKGYFPEPVTLTWNSGSLSSGVHTFPAVLQSDL

YTLSSSVTVTSSTWPSQSITCNVAHPASSTKVDKKIEPRGPTIKPCPPCKCPAPNLLGGPSVFIFPPKI

KDVLMISLSPIVTCVVVDVSEDDPDVQISWFVNNVEVHTAQTQTHREDYNSTLRVVSALPIQHQDWM

SGKEFKCKVNNKDLPAPIERTISKPKGSVRAPQVYVLPPPEEEMTKKQVTLTCMVTDFMPEDIYVEW

TNNGKTELNYKNTEPVLDSDGSYFMYSKLRVEKKNWVERNSYSCSVVHEGLHNHHTTKSFSRTPG

KGSAGGSGGDSEVQLVESGGGLVKPGGSLKLSCAASGFTFSDYYMYWVRQTPEKRLEWVATISDG

GTYTYYPDSVKGRFTISRDNAKNNLYLQMNSLKSEDTAMYYCARGWVSTMVKLLSSFPYWGQGTL

VTVSAGGGGSGGGGSGGGGSQAVVTQESALTTSPGETVTLTCRSSTGAVTTSNYANWVQEKPDH

LFTGLIGGTNNRAPGVPARFSGSLIGDKAALTITGAQTEDEAIYFCALWYSNYWVFGGGTKLTVLGQ

PK**
```

Example 8—InflaMab (Bispecific Against IL-1R1 and NLRP3) Transient Expression The aim was to carry out transient transfections of InflaMab vector DNA in ExpiCHO cells. Following culture, expressed InflaMab was purified from the culture supernatant and QC analysis carried out on the purified protein.

InflaMab is a 210 kiloDalton (kDa) bispecific mouse antibody composed of two pairs of light chain and two pairs of heavy chains with ScFv domains fused to the N-terminal, complexed together via disulphide bonds. A mammalian expression vector encoding InflaMab was transfected into ExpiCHO cells. The expressed antibody was subsequently purified from clarified culture supernatant via protein A affinity chromatography. The concentration of purified antibody was measured using a NanoDrop Lite, Thermofisher and purity was evaluated using SDS-PAGE.

Sequence

DNA coding for the amino acid sequences of InflaMab was synthesised and cloned into the mammalian transient expression plasmid pD2610-v5 (Atum).

```
Plasmid InflaMab:
>InflaMab Light chain (Theoretical MW = 26.7 kDa)
                                                    (SEQ ID NO: 57)
MVSSAQFLGLLLLCFQGTRCDIVMTQSPATLSVTPGDRVSLSCRASQSISDYLSWYQQRSHESPRLII

KYASQSISGIPSRFSGSGSGSDFTLSINSVEPEDVGVYYCQHGHSFPLTFGSGTKLELKRADAAPTV

SIFPPSSEQLTSGGASVVCFLNNFYPKDINVKWKIDGSERQNGVLNSWTDQDSKDSTYSMSSTLTLT

KDEYERHNSYTCEATHKTSTSPIVKSFNRNEC

>InflaMab Heavy Chain (Theoretical MW = 79.3 kDa)
                                                    (SEQ ID NO: 59)
MGWTLVFLFLLSVTAGVHSQIQLVQSGPELRKPGETVRISCKASGYPFTTAGLQWVQKMSGKGLKW

IGWMNTQSEVPKYAEEFKGRIAFSLETAASTAYLQINNLKTEDTATYFCAKSVYFNWRYFDVWGAGT

TVTVSSAKTTAPSVYPLAPVCGDTTGSSVTLGCLVKGYFPEPVTLTWNSGSLSSGVHTFPAVLQSDL

YTLSSSVTVTSSTWPSQSITCNVAHPASSTKVDKKIEPRGPTIKPCPPCKCPAPNLLGGPSVFIFPPKI

KDVLMISLSPIVTCVVVDVSEDDPDVQISWFVNNVEVHTAQTQTHREDYNSTLRVVSALPIQHQDWM

SGKEFKCKVNNKDLPAPIERTISKPKGSVRAPQVYVLPPPEEEMTKKQVTLTCMVTDFMPEDIYVEW

TNNGKTELNYKNTEPVLDSDGSYFMYSKLRVEKKNWVERNSYSCSVVHEGLHNHHTTKSFSRTPG
```

```
-continued
KGSAGGSGGDSEVQLVESGGGLVKPGGSLKLSCAASGFTFSDYYMYWVRQTPEKRLEWVATISDG

GTYTYYPDSVKGRFTISRDNAKNNLYLQMNSLKSEDTAMYYCARGWVSTMVKLLSSFPYWGQGTL

VTVSAGGGGSGGGGSGGGGSQAVVTQESALTTSPGETVTLTCRSSTGAVTTSNYANWVQEKPDH

LFTGLIGGTNNRAPGVPARFSGSLIGDKAALTITGAQTEDEAIYFCALWYSNYWVFGGGTKLTVLGQ

PK
```

Transient Transfection of CHO Cells

Suspension adapted ExpiCHO cells (Thermo Fisher, UK) were routinely cultured at $1.0-3.0\times10^5$ cells/ml every 2-3 days in 500 ml vented Erlenmeyer flasks (Corning, Netherlands) agitated at 135 rpm at 37° C. 8% $CO_2$. Plasmid DNA for transfection was isolated using a Purelink Hipure plasmid filter maxiprep kit (Thermo Fisher, UK) as per the manufacturer instructions. DNA was quantified using a Nano Drop lite spectrophometer as per the manufacturer instructions.

Twenty-four hours prior to transfection, ExpiCHO cells were seeded at a concentration of $4.0\times10^6$ cells/ml in ExpiCHO expression medium and grown overnight at 135 rpm, 37° C. 8% $CO_2$. On the day of transfection, 250 ml ExpiCHO cells were diluted to a final density of $6.0\times10^6$ cells/ml in ExpiCHO expression medium. 1.0 µg/ml of plasmid DNA and 0.32% (v/v) Expifectamine CHO reagent (Thermo Fisher) were diluted separately in 4% (v/v) OptiPro SFM (Thermo Fisher). The Expifectamine CHO/Optipro complex was added to the Plasmid DNA/Optipro complex dropwise. The transfection mixture was immediately added to the ExpiCHO cells. Transfected cells were incubated overnight at 135 rpm, 37° C., 8% $CO_2$.

Twenty hours post transfection, cultures were supplemented with 0.6% (v/v) Expi CHO enhancer (Thermo Fisher, UK) and 24% ExpiCHO feed (Thermo Fisher, UK). The viability of the cells were closely monitored and cultures were harvested on day 8 by centrifugation at 4000 rpm for 40 minutes at room temperature.

Purification of InflaMab

Purifications were performed using AKTA (GE Healthcare) chromatography equipment. Prior to use, all AKTA equipment was thoroughly sanitized using 1 M NaOH. Following centrifugation, filtered (0.22 µm) cell culture supernatant was applied to an AKTA system fitted with a 1 ml HiTrap Protein A column (equilibrated with wash buffer). Following loading, the column was washed with 20 column volumes of wash buffer. Bound antibody was step eluted with 10 column volumes of elution buffer. All eluted fractions were neutralised with Tris pH 9.0 buffer. Eluted fractions corresponding to elution peak were selected for overnight dialysis into PBS. The purity of the antibody was >95%, as judged by SDS-polyacrylamide midi gels.

SDS-PAGE Analysis—See FIG. 32

Sodium Dodecyl Sulphate Polyacrylamide Electrophoresis (SDS PAGE) was carried out on purified antibody using standard methods.

Molecular weight marker shown in kilodaltons. Lanes, in FIG. 32, are as follows:

| Lane Number | Sample | Batch | Amount (µg) | Conditions |
|---|---|---|---|---|
| 1 | PageRuler Plus (Thermo Fisher) | NA | NA | Reducing |
| 2 | InflaMab | 1 | 5 | Reducing |
| 3 | Blank | NA | NA | Reducing |
| 4 | InflaMab | 1 | 5 | Non-reducing |

InflaMab is ≥95% pure as judged by analysis of SDS-polyacrylamide gels. Under reducing conditions, both heavy and the light chains of the antibody are visible and are observed at the expected molecular weight of approximately 80 and 27 kDa, respectively. Under non-reducing conditions, a single major band and several minor bands are observed. The additional bands (impurities) are likely the result of non-glycosylated IgG and IgG degradation products (e.g. a single [partial] light chain, a combination of two heavy and one light chain, two heavy chains, two heavy and one light chain).

Evaluation of Purified InflaMab

Purified InflaMab was quantified using a Nanodrop Lite spectrophotometer and the extinction coefficient 330,685 $M^{-1}$ $cm^{-1}$ (or 1.0 mg/ml=A280 of 1.7 [assuming a MW=184,276 Da]), as per the manufacturer instructions. A total of 17.5 mg of InflaMab was purified from 0.3 litres of transfected cell culture supernatant.

TABLE 3

Concentration and yield of Antibody InflaMab from a 250 ml transfection.

| Sample | Batch | Vol. of culture Super. (L) | Concentration (mg/ml) | Volume (ml) | Total (mg) | Yield (mg/L) | Endotoxin (EU/mg) |
|---|---|---|---|---|---|---|---|
| InflaMab | 1 | 0.3 | 3.15 | 5.57 | 17.55 | 58.49 | ND |

Summary: InflaMab
Material: Purified Antibody
Origin: Produced in a Chinese Hamster (*Cricetulus griseus*) Ovary cell line (no hamster or animal component added)

| Results | |
| --- | --- |
| Purity: | ≥95% pure (as determined by SDS-polyacrylamide gels [FIG.1]) |
| Endotoxin (EU/mg): | Not determined |
| Concentration (mg/ml): | 3.15 (as determined by measurement of absorbance at 280 nm) |
| Mycoplasma: | Not determined |
| Package contents and storage recommendations | |
| Volume (ml): | 5.57 |
| Total (mg): | 17.55 |
| Container: | 2 ml tube × 3 |
| Volume per container: | 2.0 ml × 2; 1.57 ml × 1 |
| Net weight: | Not determined |
| Formulation: | Provided as a 0.2 µm sterile-filtered solution in PBS. |
| Shipped: | Ice packs (+4° C.) |
| Storage: | 4° C. refrigerated |

Non-hazardous, non-infectious. For research use only.

Figure 33A:
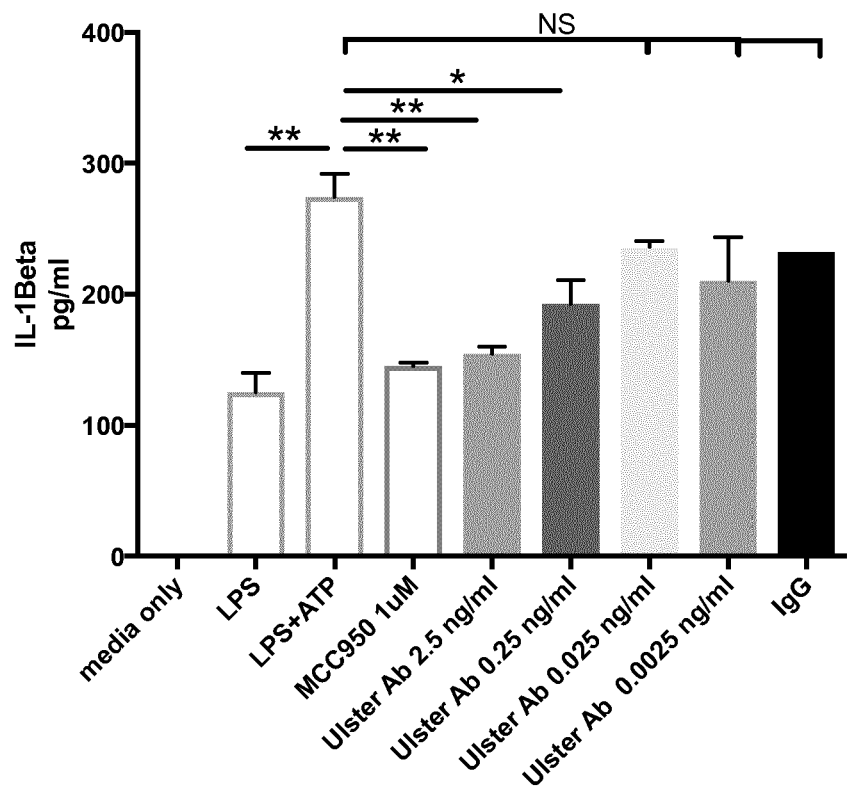
Figure 33B:
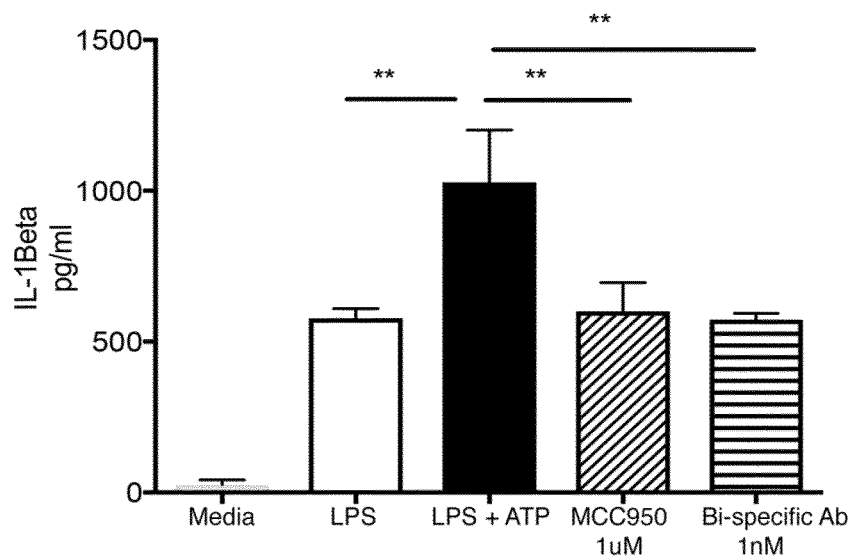

Inflamab prevents IL-1β release—see FIGS. 33a and b. THP1 cells, for FIGS. 33a and b, were cultured in 96-well plates at 100,000 cells/200 µl complete media. PMA (100 µg/ml for 72 hours) was used to differentiate THP-1 cells into macrophages. Following 24 hours of rest, differentiated THP1 cells were stimulated with LPS (1 µg/ml) for 3 hours, treated with MCC950 (1 µM) or the IL-1R1/NLRP3 Ab in a dose dependent fashion from 0.0025 ng/ml to 2.5 ng/ml for FIG. 33a or with IL-1R1/NLRP3 Ab (1 nM) for FIG. 33b or with IgG control antibody for 30 minutes, followed by ATP (5 mM) for 1 hour. IL-1 release was measured in the supernatant by ELISA.

Inflamab prevents caspase-1 activation in THP1 cells—see FIG. 34. THP1 cells, for FIG. 34, were cultured in 96-well plates at 100,000 cells/200 ul complete media. PMA (100 µg/ml for 72 hours) was used to differentiated THP-1 cells into macrophages. Following 24 hours of rest, differentiated THP1 cells were stimulated with LPS (1 ug/ml) for 3 hours, treated with the IL-1R1/NLRP3 Ab (1 ug/ml) for 30 minutes, followed by ATP (5 mM) for 1 hour. Caspase-1 activation was assessed by staining cells with a non-cytotoxic Fluorescent Labelled Inhibitor of Caspase-1 (FAM-FLICA) and DAPI (nuclear stain). Cells were treated with LPS alone (negative control), LPS+ATP (positive control), mouse IgG2a (1 ug/ml, Ab control), or IL-1 r/NLRP3 bi-specific Ab (1 ug/ml, experimental). Representative confocal images are shown for each group. Green=active caspae-1 and blue=Dapi/nuclear stain.

Internalization of Inflamab—see FIG. 35. THP1 cells, for FIG. 35, were cultured in 96-well plates at 100,000 cells/200 ul complete media. Differentiation of THP1 cells was induced by PMA (100 ug/ml for 72 hours). Following 24 hours of rest, differentiated THP1 cells were stimulated with LPS (1 ug/ml) for 3 hours, treated with a pHrodo red labelled IL-1 r/NLRP3 Ab (1 ug/ml) for 30 minutes, followed by ATP (5 mM) for 1 hour. The internalization of the Ab was tracked using a pHrodo red labelled bi-specific Ab that only fluoresces when internalized. (A) A representative confocal image shows the internalization of the pHrodo red labelled bi-specific Ab in a differentiated THP1 cell. (B) A representative confocal image shows significant reduction of caspase-1 activation (green) in THP1 cells that have internalized the bi-specific Ab (red, white arrow) as compared to THP1 cells that did not internalize the Ab (green only).

Example 9—Targeting NLRP3 for Glaucoma

Background and Significance

Glaucoma is the leading cause of irreversible blindness worldwide, characterized by the progressive loss of retinal ganglion cells (RGCs). A recent study estimates that approximately 60 million people worldwide currently suffer from glaucoma and with the rapidly growing aging population this number is predicted to exceed 100 million by 2040 [1]. Unfortunately, there is no cure for glaucoma and intraocular pressure (IOP) reduction remains the only treatment strategy for all types of glaucoma [2]. However, while elevated IOP is a major risk factor for the development of glaucoma, lowering IOP alone does not prevent disease progression and many patients still experience significant vision loss even after IOP has been successfully lowered [3]. Moreover, the increasing incidence of normal tension glaucoma [4, 5] and the absence of neurodegeneration in some patients with elevated IOP [6] indicate that IOP-independent mechanisms also contribute to the development and progression of glaucoma and highlight the need for developing IOP-independent neuroprotective therapies to prevent disease progression and preserve vision.

Glaucoma is a complex multifactorial disease and while the exact mechanisms that mediate axon degeneration and death of RGCs are not well understood, there is growing evidence that axon damage in the optic nerve head (ONH) precedes death of the RGCs [7, 8]. Moreover, the axon damage in the ONH has been linked to glial activation and inflammation [9, 10]. In human and experimental models of glaucoma, activated astrocytes [10, 11] and activated microglia [9, 12] are detected in ONH and coincides with increased expression of proinflammatory cytokines such as IL-1β and TNFα and neurotoxic mediators such as Nitric Oxide (NO), Reactive Oxygen Species (ROS), and Glutamate [12-14]. However, how elevated IOP triggers glial activation and how the inflammatory cascade is amplified and sustained is not well understood.

The NLRP3 inflammasome is an intracellular multi-protein complex that triggers inflammation in response to signals generated by infectious organisms, as well as endogenous signals associated with cell stress and tissue damage [15]. Dysregulation of the NLRP3 inflammasome has been implicated in several neurodegenerative diseases, including Alzheimer's disease and multiple sclerosis [16] but, most recently, activation of the NLRP3 inflammasome has been associated with the death of RGCs following retinal ischemia reperfusion injury and optic nerve crush [17, 18].

Results

Focusing specifically on the ONH region, where glial activation and inflammation has been linked to early axon damage, it has been demonstrated that NLRP3 is constitutively expressed in the ONH of mouse and human [FIG. 36] and astrocyte-specific expression was confirmed by immunofluorescence showing co-localization of NLRP3 with the astrocyte-specific marker GFAP in the human ONH [FIG. 37]. Using a microbead-induced mouse model of glaucoma in conjunction with a fluorescent reporter mouse to track inflammasome activation in vivo [19, 20], it has been demonstrated that NLRP3 inflammasome activation occurs early in the ONH following elevated IOP and coincides with induction of pro-inflammatory mediators in the ONH [FIG.

38]. Using knockout mice that lacked the ASC adaptor protein (ASC KO), an essential component of the NLRP3 inflammasome, it has been demonstrated that early induction of inflammatory mediators and accumulation of Iba1+ immune cells in the ONH was dependent upon inflammasome activation [FIG. 39]. Moreover, using mice that specifically lacked NLRP3 (NLRP3 KO) it was demonstrated that NLRP3 specifically mediated axon degeneration and death of RGCs in the microbead-induced mouse model of glaucoma [20] [FIG. 40]. However, the most clinically relevant study revealed that systemic treatment of mice with a commercially available small molecule inhibitor of NLRP3 (MCC950) [21] prevented the death of RGCs in the microbead-induced mouse model of glaucoma [FIG. 41]. This study provides proof-of-concept that pharmacologically targeting NLRP3 can serve as a neuroprotective therapy in glaucoma. However, due to a very short half-life, MCC950 had to be administered systemically every other day for the length of the study and as a potential treatment for glaucoma, systemically blocking the NLRP3 inflammasome in an aging population is not ideal, since the inflammasome plays an integral role in host defense against infection [15, 22]. In glaucoma, a disease that is limited to the RGCs and their axons, local delivery of the inhibitor into the vitreous would be ideal, but would require an inhibitor with a longer half-life in order to limit the number of intravitreal injections. Biologics are known to have longer half-lives than small molecules [23] and there is strong precedence of using local administration of biologics in ophthalmology to treat eye diseases such as age-related macular degeneration.

In vitro studies clearly demonstrate the ability of Inflamab (NLRP3/IL1 R1) to inhibit inflammasome activation (FIG. 33a to FIG. 35), and in vivo studies are now currently underway to assess the neuroprotective effect of InflaMab (NLRP3/IL1 R1 bispecific antibody) when administered intravitreally in a microbead-induced mouse model of glaucoma. In the current study, WT C57BL/6J mice are receiving a single intravitreal injection of Inflamab (final vitreous concentration of 2.5, 25, or 250 ng/ml) on Day 0, immediately preceding the injection of microbeads and mice receiving saline only (no beads) are serving as a non-glaucoma control. RGC function is currently being measured by pERG using a fully integrated ERG system for rodents (Celeris). Changes in pERG amplitude is being measured in mice that received microbeads only and compared to mice that received microbeads plus Inflamab (final vitreous concentration of 2.5, 25, and 250 ng/ml) or saline only (no beads) [FIG. 42]. In these studies, preliminary pERG results reveal a recovery of RGC function in the microbead-injected mice treated with Inflamab at a final vitreous concentration of 250 ng/ml as compared to mice receiving microbeads only or microbeads plus Inflamab at 2.5 or 25 ng/ml. Visual acuity using an optomotor reflex-based spatial frequency threshold test, as well as RGC and axon quantification, is performed to further corroborate the neuroprotective effect of Inflamab and including additional control groups (microbead-injected mice treated with the appropriate IgG control antibody).

NLRP3 is constitutively expressed in the mouse and human optic nerve head—see FIG. 36. (A) Protein lysates were prepared from the ONH tissue of WT C57BL/6J mice and subjected to immunoblotting for NLRP3 (red) with actin (green) as a loading control. Conjunctiva (conj) from C57BL/6J WT mice was used as a positive control and ONH and conjunctival tissues from NLRP3 KO mice were used as negative controls. Western blot analysis demonstrates that NLRP3 is constitutively expressed in the non-glaucomatous mouse ONH. (B) Immunohistochemistry in sections of nonglaucomatous human optic nerve shows constitutive expression of NLRP3 (red) in the lamina cribosa region of the optic nerve head, with no constitutive expression in the myelinated portion of the optic nerve.

NLRP3 is constitutively expressed in optic nerve head astrocytes of normal (non-glaucomatous) human eyes—see FIG. 37. Immunofluorescence in sections of human optic nerve shows co-localization of NLRP3 (red) with the astrocyte-specific marker GFAP (Green) in the unmeylinated lamina cribosa region of the optic nerve head. Dapi (blue) was used to identify all nucleated cells. Images are representative of staining performed on optic nerve sections obtained from three individual (non-glaucomatous) human optic nerves.

NLRP 3 inflammasome assembly in the ONH coincides with induction of inflammatory mediators at 7 days post microbead injection—see FIG. 38. ASC-speck formation was monitored in vivo using a fluorescent reporter mouse (ASC citrine/Cre+). (A) At 7 days post microbead injection or saline as a control, frozen eye sections were stained for GFAP (astrocytes, pink), MBP (myelin,red), and DAPI (blue). (B) The total number of ASC-citrine specks (green) was counted in the ONH region (top of the ONH to the myelinization zone (dotted line) and neural retina using Image J (N=5 sections per eye). A significant increase in the number of ASC-citrine specks was observed in the ONH, but not the retina, at 7 days post microbead as compared to saline. ***P<0.001, N=4 per group. (C) Staining with NLRP3 demonstrates constitutive expression of NLRP3 (red) and ASC (green) in the ONH of the saline injected control eye, but the ASC and NLRP3 do not co-localize (merged image). By contrast, at 7 days post microbead injection, the ASC-citrine specks co-localized with NLRP3 (yellow staining in merged image), indicating inflammasome assembly and activation of NLRP3. (D) Quantitative PCR on ONH and retinal tissue from 7 days post microbead injection revealed a significant increase in mRNA levels of GFAP, IL-1β, IL-18, and TNFα in the ONH but not retina when compared to uninjected contralateral eyes (fold of control). N=5 mice/group (qPCR), *P<0.05, P>0.001, *P<0.001.

Macrophage infiltration and inflammatory gene expression in WT and ASC KO mice following elevated IOP—see FIG. 39. (A) Frozen sections (3 sections per eye) were taken from WT and ASC KO eyes at 0, 7, and 14 days after microbead injection and the total number of Iba1+ cells (macrophage/microglia) was counted in the ONH region (top of the ONH to the myelinisation zone). (B) Results show a significant increase in the number of Iba1+ cells at D7 and D14 post microbead injection in WT but not ASC KO ONH. (C) Quantitative PCR on ONH tissue from 7 and 14 days post microbead injection revealed a significant increase in mRNA levels of IL-1β and IL-18 in WT as compared to uninjected contralateral eyes (fold of control). This increase in inflammatory gene expression was completely abrogated in ASC KO mice. N=5 mice/group (Immunofluorescence) and N=6-8 mice/group (qPCR), *P<0.05, P>0.001, *P<0.001.

RGC and axon analysis in WT, ASC KO, and NLRP3 KO mice—see FIG. 40. C57BL/6J WT, ASC KO, and NLRP3 KO mice received an anterior chamber injection of sterile polystyrene microbeads (7.2×106.15 μm) or saline as a control. Uninjected contralateral eyes were used as negative controls and IOP was followed every 3 days for 4 weeks using a rebound tonometer (TonoLab). (A) IOP analysis reveals a significant increase in IOP in microbead injected WT, ASC KO, and NLRP3 KO mice as compared to saline and uninjected contralateral controls, with no significant difference in the time course or magnitude of the microbead-induced IOP between WT, ASC KO, and NLRP3 KO mice. (B) At 4 weeks post microbead injection RGC density was quantitated in retinal flatmounts stained with p-III-tubulin (RGC specific marker) and data are presented as % RGC survival compared to uninjected contralateral eyes. (C) Axon density was quantitated in optic nerves stained with PPD and data presented as % axon survival compared to uninjected contralateral eyes a. N=8-10/group, ****P<0.0001).

RGC analysis in WT mice treated with the NLRP3 inhibitor MCC950—see FIG. 41. To determine if treatment with MCC950 (small molecule NLRP3 inhibitor) can prevent RGC death in a microbead-induced mouse model of glaucoma, WT C57BL/6J mice received ip injections of MCC950 (10 mg/kg, starting on Day 0) every other day for 4 weeks. Uninjected contralateral eyes and mice receiving vehicle only served as negative controls. (A) IOP analysis reveals a significant increase in IOP in microbead injected WT mice treated with vehicle or MCC950 as compared to no beads control, with no significant difference in the time course or magnitude of the microbead-induced IOP between vehicle and MCC950 treated mice. (B) Representative confocal images of retinal flatmounts at 4 weeks post microbead injection stained with the RGC-specific marker Brn3a (red) and the nuclear marker Dapi (blue). (C) At 4 weeks post microbead injection RGC density was quantitated and showed a significant decrease in RGC density in microbead-injected WT mice that received vehicle only as compared to uninjected (no beads) contralateral eyes. By contrast, mice treated with MCC950 showed significant RGC protection with RGC densities equal to that of uninjected (no beads) controls. N=5 per group, ***P<0.001).

RGC function in WT mice treated with the NLRP3 inhibitor InflaMab—see FIG. 42. To determine if local treatment with InflaMab (NLRP3/IL1 R1 bispecific antibody) can protect RGCs in a microbead-induced mouse model of glaucoma, WT C57BL/6J mice received a single intravitreal injection of Inflamab (final vitreous concentration of 2.5, 25, or 250 ng/ml) on Day 0, immediately preceding the injection of microbeads. Mice receiving saline only (no beads) served as a normal (no glaucoma) control. RGC function was measured by pERG using a fully integrated ERG system for rodents (Celeris) and changes in pERG amplitude was measured in mice that received microbeads only and compared to mice that received microbeads plus Inflamab (2.5, 25, and 250 ng/ml) or saline only (no beads). N=4-5 per group. These studies are currently in progress. The preliminary pERG results presented herein reveal a recovery of RGC function in the microbead-injected mice treated with Inflamab at a final vitreous concentration of 250 ng/ml as compared to mice receiving microbeads only or microbeads plus Inflamab at 2.5 or 25 ng/ml. Visual acuity using an optomotor reflex-based spatial frequency threshold test, as well as RGC and axon quantification will also be performed to further corroborate the neuroprotective effect of Inflamab and additional control groups (microbead-injected mice treated with IgG control) will also be added.

REFERENCES

1. Tham Y C, X Li, T Y wong, H A Quigley, C Y Cheng. Global prevalence of glaucoma and projections of glaucoma burden through 2040. Ophthalmol. 2014; 121911):2081-2090.
2. Casson R J, G Chidlow, et al. Definition of glaucoma; clinical and experimental concepts. Clin Exp Ophthalmol. 2012; 40(4):341.
3. Leske M C, A Heijl, M Hussein et al., Factors for glaucoma progression and the effect of treatment: the early manifest glaucoma trial. Arch Ophthalmol. 2003; 121:48-56.
4. Mudumbai R. C. 2013. Clinical update on normal tension glaucoma. Sem. Ophthalmol. 28(3):173-179.
5. Song B. J., J. Caprioli. 2014. New directions in the treatment of normal tension glaucoma. Indian J. Ophthalmol. 62(5):529-537.
6. Leibowitz H M, D E Krueger, L R Maunder, et al. The Framingham Eye Study monograph: an ophthalmological and epidemiological study of cataract, glaucoma, diabetic retinopathy, macular degeneration, and visual acuity in a general population of 2631 adults, 1973-1975. Surv. Ophthalmol. 1980; 24suppl:335-610.
7. Howell G R, R T Libby, T C Jakobs, R S Smith, F C Phalan, et al. Axons of retinal ganglion cells are insulted in the optic nerve early in DBA/2J glaucoma. J Cell Biol. 2007; 179:1523-1537.
8. Buckingham B P, D M Inman, W Lambert, E Oglesby, D J Calkins et al. Progressive ganglion cell degeneration precedes neuronal loss in a mouse model of glaucoma. J Neurosci 2008; 28:2735-2744.
9. Bordone M P, M F Gonzalez Fleitas, L A Pasquini, A Bosco et al. Involvement of microglia in early axoglial alterations of the optic nerve induced by experimental glaucoma. J Neurochem 2017; 142:323-337.
10. Sun D, J Qu, T C Jakobs. Reversible reactivity by optic nerve astrocytes. Glia. 2013; 61(8):1218-1235.
11. Hernandez M R, O A Agapova, P Yang, M Salvador-Silva, C S Ricard, S Aoi. Differential gene expression in astrocytes from human normal and glaucomatous optic nerve head analyzed by cDNA microaray. Glia 2002; 38:45-64.
12. Yuan L, A H Neufeld. Activated microglia in the human glaucomatous optic nerve head. J Neurosci Res. 2001; 64:523-532.
13. G. Tezel. 2006. Oxidative stress in glaucomatous neurodegeneration: mechanisms and consequences. Pro Retin Eye Res 25490.
14. Tezel, G, and M B Wax. 2003. Glial modulation of retinal ganglion cell death in glaucoma. J Glaucoma 12: 63-68.
15. Mariathasan S, D M Monack. Inflammasome adaptors and sensors:intracellular regulators of infection and inflammation. Nat Rev Immunol. 2007; 7:31-40.
16. Freeman L C, J P Ting. The pathogenic role of the inflammasome in neurodegenerative diseases. J Neuroinflam 2018; 15(1):164.
17. Chi W, F Li, H Chen, Y Wang, Y Zhu et al. Caspase-8 promotes NLRP1/NLRP3 inflammasome activation and IL-1β production in acute glaucoma. Proc Natl Acad Sci USA. 2014; 111(30):11181-6.
18. Puyang Z, L Feng, H Chen, P Liang, J B Troy, X Liu. Retinal Ganglion Cell Loss is Delayed Following Optic Nerve Crush in NLRP3 Knockout Mice. Sci Rep 2016; 6:20998.
19. Tzeng T C, S Schattgen, B Monks, et al., A Fluorescent Reporter Mouse for Inflammasome Assembly Demonstrates an Important Role for Cell-Bound and Free ASC Specks during In Vivo Infection. Cell Re. 2016; 16(2): 571-82
20. Gregory-Ksander, M S, F Fei, A Krishnan, T Tzeng, et al. Destructive neuroinflammation triggered by activation of the NLRP3 inflammasome in the glaucomatous optic nerve head. Invest Ophthalmol Vis Sci. 2017; 58(8):2021.
21. Coll R C, AAB Robertson, J J Chae, S C Higgins, et al., A small molecule inhibitor of the NLRP3 inflammasome is a potential therapeutic for inflammatory diseases. Nat Med. 2015; 21(3):248-255.
22. McGilligan V E, M S Gregory—Ksander, L Dayu, J E Moore et al. *Staphylococcus aureus* Activates the NLRP3 Inflammasome in Human and Rat Conjunctival Goblet Cells. PLoS One, 2013; ; 8(9):e74010.
23. Hong Wan. An overall comparison of small molecules and large biologics in ADME testing. ADMET & DMPK 4(1) (2016) 1-22.

The invention is not limited to the embodiments described herein but can be amended or modified without departing from the scope of the present invention.

The invention claimed is:

1. A method for the treatment and/or prophylaxis of an inflammatory eye disease, the method comprising:
providing a therapeutically effective amount of an NLRP3 inflammasome modulator which is capable of binding to both of IL-1R1 and NLRP3 and which suppresses activation and/or signaling of the NLRP3 inflammasome;
administering the therapeutically effective amount of said modulator to a subject in need of such treatment,
wherein the NLRP3 inflammasome modulator comprises a bispecific antibody having a first antibody moiety and a second antibody moiety,
the first antibody moiety comprising three heavy chain complementary determining regions (CDRs) and three light chain CDRs, wherein the heavy chain CDRs of the first antibody moiety comprise GYPFTTAG (SEQ ID NO: 60), MNTQSEVP (SEQ ID NO: 61), and AKSVYFNWRYFDV (SEQ ID NO: 62), wherein the light chain CDRs of the first antibody moiety comprise: QSISDY (SEQ ID NO: 63), YAS, and QHGHSFPLT (SEQ ID NO: 64); and
the second antibody moiety comprising three heavy chain complementary determining regions (CDRs) and three light chain CDRs, wherein the heavy chain CDRs of the second antibody moiety comprise GFTFSDYY (SEQ ID NO: 65), ISDGGTYT (SEQ ID NO: 66), and ARGWVSTMVKLLSSFPY (SEQ ID NO: 67), wherein the light chain CDRs of the second antibody moiety comprise TGAVTTSNY (SEQ ID NO: 68), GTN, and ALWYSNYWV (SEQ ID NO: 69).

2. The method of claim 1, wherein the first and/or second antibody moiety of the bispecific antibody is selected from the group consisting of: a polyclonal antibody, a monoclonal antibody, a humanized antibody, a chimeric antibody, a combination thereof, and fragments of each thereof.

3. The method of claim 1, wherein the first and/or the second antibody moiety is a monoclonal antibody.

4. The method of claim 1, wherein the first and/or second antibody moiety of the bispecific antibody comprises an antibody fragment, wherein the antibody fragment is one or more of Fab, Fv, Fab', (Fab')2, scFv, bis-scFv, minibody, Fab2, and Fab3.

5. The method of claim 1, wherein the first and/or second antibody moiety of the bispecific antibody is a recombinant humanized antibody or antibody fragment.

6. A method to reduce or prevent or treat at least one symptom of an inflammatory eye disease in a subject comprising selectively inhibiting and/or reducing activation of a NLRP3 inflammasome pathway by the use of an NLRP3 inflammasome modulator which is capable of binding to both of IL-1R1 and NLRP3;
wherein the NLRP3 inflammasome modulator comprises a bispecific antibody having a first antibody moiety and a second antibody moiety,
the first antibody moiety comprising three heavy chain complementary determining regions (CDRs) and three light chain CDRs, wherein the heavy chain CDRs of the first antibody moiety comprise GYPFTTAG (SEQ ID NO: 60), MNTQSEVP (SEQ ID NO: 61), and AKSVYFNWRYFDV (SEQ ID NO: 62), wherein the light chain CDRs of the first antibody moiety comprise: QSISDY (SEQ ID NO: 63), YAS, and QHGHSFPLT (SEQ ID NO: 64); and
the second antibody moiety comprising three heavy chain complementary determining regions (CDRs) and three light chain CDRs, wherein the heavy chain CDRs of the second antibody moiety comprise GFTFSDYY (SEQ ID NO: 65), ISDGGTYT (SEQ ID NO: 66), and ARGWVSTMVKLLSSFPY (SEQ ID NO: 67), wherein the light chain CDRs of the second antibody moiety comprise TGAVTTSNY (SEQ ID NO: 68), GTN, and ALWYSNYWV (SEQ ID NO: 69).

7. The method of claim 6, wherein the inflammatory eye disease is glaucoma.

8. The method of claim 6, wherein the inflammatory eye disease is age related macular degeneration, diabetic retinopathy, or glaucoma.

9. The method of claim 6, wherein the bispecific antibody is also capable of binding to the PYD domain of NLRP3.

10. The method of claim 1 or 6, wherein the bispecific antibody is a recombinant humanized bi-antibody capable of binding to both of: IL-1R1 and NLRP3.

11. The method of claim 10, wherein the bispecific antibody comprises the amino acid sequence:
MVSSAQFLGLLLLCFQGTRCDI-VMTQSPATLSVTPGDRVSLSCRASQSIS-DYLSWYQQRS HESPRLIIKYASQSIS-GIPSRFSGSGSGSDFTLSINSVEPEDVGVY YCQHGHSFPLTFGSGTK
LELKRADAAPTVSIFPPSSEQLTSG-GASVVCFLNNFYPKDINVKWKIDGSER-

QNGVLNS WTDQDSKDSTYSMSSTLTLTKDEYERHNSYTCEATTHKTSTSPIVKSFNRNEC (SEQ ID NO: 57).

12. The method of claim 10, wherein the bispecific antibody comprises the amino acid sequence:

(SEQ ID NO: 59)
MGWTLVFLFLLSVTAGVHSQIQLVQSGPELRKPGETVRISCKASGYPFTT
AGLQWVQKMSGKGLKWIGWMNTQSEVPKYAEEFKGRIAFSLETAASTAYL
QINNLKTEDTATYFCAKSVYFNWRYFDVWGAGTTVTVSSAKTTAPSVYPL
APVCGDTTGSSVTLGCLVKGYFPEPVTLTWNSGSLSSGVHTFPAVLQSDL
YTLSSSVTVTSSTWPSQSITCNVAHPASSTKVDKKIEPRGPTIKPCPPCK
CPAPNLLGGPSVFIFPPKIKDVLMISLSPIVTCVVVDVSEDDPDVQISWF
VNNVEVHTAQTQTHREDYNSTLRVVSALPIQHQDWMSGKEFKCKVNNKDL
PAPIERTISKPKGSVRAPQVYVLPPPEEEMTKKQVTLTCMVTDFMPEDIY
VEWTNNGKTELNYKNTEPVLDSDGSYFMYSKLRVEKKNWVERNSYSCSVV
HEGLHNHHTTKSFSRTPGKGSAGGSGGDSEVQLVESGGGLVKPGGSLKLS
CAASGFTFSDYYMYWVRQTPEKRLEWVATISDGGTYTYYPDSVKGRFTIS
RDNAKNNLYLQMNSLKSEDTAMYYCARGWVSTMVKLLSSFPYWGQGTLVT
VSAGGGGSGGGGSGGGGSQAVVTQESALTTSPGETVTLTCRSSTGAVTTS
NYANWVQEKPDHLFTGLIGGTNNRAPGVPARFSGSLIGDKAALTITGAQT
EDEAIYFCALWYSNYWVFGGGTKLTVLGQPK.

\* \* \* \* \*

UNITED STATES PATENT AND TRADEMARK OFFICE
CERTIFICATE OF CORRECTION

| | | |
|---|---|---|
| PATENT NO. | : 12,227,579 B2 | Page 1 of 1 |
| APPLICATION NO. | : 17/275995 | |
| DATED | : February 18, 2025 | |
| INVENTOR(S) | : Victoria McGilligan | |

It is certified that error appears in the above-identified patent and that said Letters Patent is hereby corrected as shown below:

In the Claims

In Claim 11, at Column 123, Line 2, "ERHNSYTCEATTHKTSTSPIVKSFNRNEC" should be -- ERHNSYTCEATHKTSTSPIVKSFNRNEC -- therefor.

Signed and Sealed this
Fifteenth Day of April, 2025

Coke Morgan Stewart
*Acting Director of the United States Patent and Trademark Office*